(12) United States Patent
Chadeayne

(10) Patent No.: US 12,391,645 B2
(45) Date of Patent: Aug. 19, 2025

(54) N-ISOPROPYL TRYPTAMINES AND METHOD OF MAKING MONOALKYLATED AND DIALKYLATED TRYPTAMINE ANALOGS

(71) Applicant: CAAMTECH, INC., Issaquah, WA (US)

(72) Inventor: Andrew R. Chadeayne, Issaquah, WA (US)

(73) Assignee: CAAMTECH, INC., Issaquah, WA (US)

( * ) Notice: Subject to any disclaimer, the term of this patent is extended or adjusted under 35 U.S.C. 154(b) by 0 days.

(21) Appl. No.: 18/865,727

(22) PCT Filed: May 22, 2023

(86) PCT No.: PCT/US2023/067304
§ 371 (c)(1),
(2) Date: Nov. 14, 2024

(87) PCT Pub. No.: WO2023/225679
PCT Pub. Date: Nov. 23, 2023

(65) Prior Publication Data
US 2025/0197352 A1      Jun. 19, 2025

Related U.S. Application Data

(60) Provisional application No. 63/385,263, filed on Nov. 29, 2022, provisional application No. 63/385,312, filed on Nov. 29, 2022, provisional application No. 63/385,289, filed on Nov. 29, 2022, provisional application No. 63/385,320, filed on Nov. 29, 2022, provisional application No. 63/385,267, filed on Nov. 29, 2022, provisional application No. 63/344,145, filed on May 20, 2022.

(51) Int. Cl.
C07D 209/16      (2006.01)
(52) U.S. Cl.
CPC .................. C07D 209/16 (2013.01)
(58) Field of Classification Search
CPC .................................................. C07D 209/16
See application file for complete search history.

(56) References Cited

U.S. PATENT DOCUMENTS

| | | |
|---|---|---|
| 2018/0221396 A1 | 8/2018 | Chadeayne |
| 2019/0142851 A1 | 5/2019 | Chadeayne |
| 2021/0169850 A1 | 6/2021 | Weinstock-Rosin et al. |

FOREIGN PATENT DOCUMENTS

| | | |
|---|---|---|
| WO | 2021/226041 A1 | 11/2021 |
| WO | 2021/236759 A2 | 11/2021 |
| WO | 2022/150675 A1 | 7/2022 |

OTHER PUBLICATIONS

Pillaiyar, et al. (2018), "General Synthesis of Unsymmetrical 3,3'-(Aza)diindolylmethane Derivatives", Journal of Organic Chemistry, 83(17), 9902-9913.
International Search Report and Written Opinion in International Application No. PCT/US2023/067304 dated Nov. 3, 2023.
Dolomanov, O. V., Bourhis, L. J., Gildea, R. J., Howard, J. A. K. & Puschmann, H. (2009). J. Appl. Cryst. 42, 339-341.
Sheldrick, G. M. (2015). Acta Cryst. C71, 3-8.
Xu et al. (1999), "N-Methyl-5-tert-butyltryptamine: A Novel, Highly Potent 5-HT1D Receptor Agonist", Journal of Medicinal Chemistry, 42(3), 526-531.

*Primary Examiner* — Shawquia Jackson
(74) *Attorney, Agent, or Firm* — RAPHAEL BELLUM PLLC

(57) ABSTRACT

The disclosure relates to [2-(5-chloro-1H-indol-3-yl)ethyl](propan-2-yl)azanium iodide (5-chloro-N isopropyltryptammonium iodide or 5-Cl-NiPT iodide), crystalline 5-Cl-NiPT iodide, [2-(5-methoxy-1H-indol-3-yl)ethyl](propan-2-yl) azanium iodide (5-methoxy-N-isopropyltryptammonium iodide or 5-MeO-NiPT iodide), crystalline 5-MeO-NiPT iodide, [2-(5-methyl-1H-indol-3-yl)ethyl](propan-2-yl)azanium iodide (5-methyl-N-isopropyltryptammonium iodide or 5-Me-NiPT iodide), crystalline 5-Me-NiPT iodide, [2-(2-methyl-1H-indol-3-yl)ethyl](propan-2-yl)azanium iodide (2-methyl-N-isopropyltryptammonium iodide or 2-Me-NiPT iodide), crystalline 2-Me-NiPT iodide, [2-(7-methyl 1H-indol-3-yl)ethyl](propan-2-yl)azanium iodide (7-methyl-N-isopropyltryptammonium iodide or 7-Me-NiPT iodide), crystalline 7-Me-NiPT iodide, [2-(5-fluoro-1H-indol-3-yl)ethyl](propan-2-yl)azanium iodide (5-fluoro-N-isopropyltryptammonium iodide or 5-F-NiPT iodide), crystalline 5-F-NiPT iodide, and specific crystalline forms thereof, including crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, and crystalline form 1 of 5-F-NiPT iodide, to compositions containing the same, and to methods of treatment using them. This disclosure relates to monoalkylated and dialkyled tryptamine analogs, and to methods of treatment/therapeutic uses thereof. This disclosure relates to an improved method of making monoalkylated and dialkylated tryptamine analogs.

2 Claims, 14 Drawing Sheets

N-ISOPROPYL TRYPTAMINES AND METHOD OF MAKING MONOALKYLATED AND DIALKYLATED TRYPTAMINE ANALOGS

CROSS-REFERENCE TO RELATED APPLICATION

This application claims priority to U.S. Provisional Application No. 63/344,145, filed on May 20, 2022; U.S. Provisional Application No. 63/385,263, filed on Nov. 29, 2022; U.S. Provisional Application No. 63/385,312, filed on Nov. 29, 2022; U.S. Provisional Application No. 63/385,267, filed on Nov. 29, 2022; U.S. Provisional Application No. 63/385,320, filed on Nov. 29, 2022; and U.S. Provisional Application No. 63/385,289, filed on Nov. 29, 2022; the disclosures of which are all incorporated herein by reference.

TECHNICAL FIELD

This disclosure relates to [2-(5-chloro-1H-indol-3-yl)ethyl](propan-2-yl)azanium iodide (5-chloro-N-isopropyltryptammonium iodide or 5-Cl-NiPT iodide), crystalline 5-Cl-NiPT iodide, and specific crystalline forms thereof, including crystalline form 1 of 5-Cl-NiPT iodide; to pharmaceutical compositions containing 5-Cl-NiPT iodide or crystalline 5-Cl-NiPT iodide, including crystalline form 1 of 5-Cl-NiPT iodide; and to methods of treatment/therapeutic uses of 5-Cl-NiPT iodide or crystalline 5-Cl-NiPT iodide, including crystalline form 1 of 5-Cl-NiPT iodide.

This disclosure further relates to [2-(5-methoxy-1H-indol-3-yl)ethyl](propan-2-yl)azanium iodide (5-methoxy-N-isopropyltryptammonium iodide or 5-MeO-NiPT iodide), crystalline 5-MeO-NiPT iodide, and specific crystalline forms thereof, including crystalline form 1 of 5-MeO-NiPT iodide; to pharmaceutical compositions containing 5-MeO-NiPT iodide or crystalline 5-MeO-NiPT iodide, including crystalline form 1 of 5-MeO-NiPT iodide; and to methods of treatment/therapeutic uses of 5-MeO-NiPT iodide or crystalline 5-MeO-NiPT iodide, including crystalline form 1 of 5-MeO-NiPT iodide.

This disclosure further relates to [2-(5-methyl-1H-indol-3-yl)ethyl](propan-2-yl)azanium iodide (5-methyl-N-isopropyltryptammonium iodide or 5-Me-NiPT iodide), crystalline 5-Me-NiPT iodide, and specific crystalline forms thereof, including crystalline form 1 of 5-Me-NiPT iodide; to pharmaceutical compositions containing 5-Me-NiPT iodide or crystalline 5-Me-NiPT iodide, including crystalline form 1 of 5-Me-NiPT iodide; and to methods of treatment/therapeutic uses of 5-Me-NiPT iodide or crystalline 5-Me-NiPT iodide, including crystalline form 1 of 5-Me-NiPT iodide.

This disclosure further relates to [2-(2-methyl-1H-indol-3-yl)ethyl](propan-2-yl)azanium iodide (2-methyl-N-isopropyltryptammonium iodide or 2-Me-NiPT iodide), crystalline 2-Me-NiPT iodide, and specific crystalline forms thereof, including crystalline form 1 of 2-Me-NiPT iodide; to pharmaceutical compositions containing 2-Me-NiPT iodide or crystalline 2-Me-NiPT iodide, including crystalline form 1 of 2-Me-NiPT iodide; and to methods of treatment/therapeutic uses of 2-Me-NiPT iodide or crystalline 2-Me-NiPT iodide, including crystalline form 1 of 2-Me-NiPT iodide.

This disclosure further relates to [2-(7-methyl-1H-indol-3-yl)ethyl](propan-2-yl)azanium iodide (7-methyl-N-isopropyltryptammonium iodide or 7-Me-NiPT iodide), crystalline 7-Me-NiPT iodide, and specific crystalline forms thereof, including crystalline form 1 of 7-Me-NiPT iodide; to pharmaceutical compositions containing 7-Me-NiPT iodide or crystalline 7-Me-NiPT iodide, including crystalline form 1 of 7-Me-NiPT iodide; and to methods of treatment/therapeutic uses of 7-Me-NiPT iodide or crystalline 7-Me-NiPT iodide, including crystalline form 1 of 7-Me-NiPT iodide.

[2-(5-fluoro-1H-indol-3-yl)ethyl](propan-2-yl)azanium iodide (5-fluoro-N-isopropyltryptammonium iodide or 5-F-NiPT iodide), crystalline 5-F-NiPT iodide, and specific crystalline forms thereof, including crystalline form 1 of 5-F-NiPT iodide; to pharmaceutical compositions containing 5-F-NiPT iodide or crystalline 5-F-NiPT iodide, including crystalline form 1 of 5-F-NiPT iodide; and to methods of treatment/therapeutic uses of 5-F-NiPT iodide or crystalline 5-F-NiPT iodide, including crystalline form 1 of 5-F-NiPT iodide.

This disclosure further relates to monoalkylated and dialkyled tryptamine analogs, and to methods of treatment/therapeutic uses thereof.

This disclosure further relates to an improved method of making monoalkylated and dialkylated tryptamine analogs.

BACKGROUND OF THE INVENTION

Obtaining specific salts or crystalline forms of an active pharmaceutical ingredient (API) is extremely useful in drug development. It permits better characterization of the drug candidate's chemical and physical properties. Crystalline forms often have better chemical and physical properties than the API in its amorphous state. Such crystalline forms may possess more favorable pharmaceutical and pharmacological properties or be easier to process. Additionally, preparing a crystalline API and solving its crystal structure provides the gold standard for chemical characterization and determining the molecular formula (and molecular weight) of the API. Accordingly, preparing a crystalline form with an accompanying crystal structure thereof prevents potential ambiguities and/or inaccuracies in the API's molecular weight. This is important because the API's molecular weight is used to calculate the concentration of compositions comprising that API. Thus, inaccuracies in molecular weight may lead to errors in the calculations pertaining to dosing, potency, toxicity, etc. in all downstream in vitro and in vivo assays that correlated the concentration of the API with a measured property. Accordingly, there remains a need to obtain and characterize crystalline forms of APIs, such as tryptamines and other psychedelic drug compounds.

Serotonin (3-(2-aminoethyl)-1H-indol-5-ol) is an important neurotransmitter. As shown below, serotonin is a primary amine.

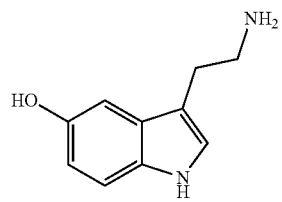 [SMILES: NCCc1c[nH]c2ccc(O)cc12]

Serotonin analogs (tryptamines) are useful for modulating a serotonin system, e.g., as a serotonergic drug. Like serotonin, tryptamine, as shown below, is a primary amine.

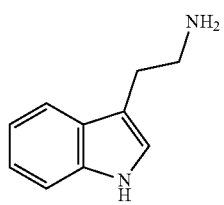 [SMILES: NCCc1c[nH]c2ccccc12]

Alkylated tryptamines have different properties compared to serotonin. Tryptamines can either be primary amines (no additional alkyl groups), monoalkylated (secondary amine), dialkylated (tertiary amine), or trialkylated (quaternary tryptammonium). When administered to mammals (e.g., mice, rates, humans, etc.) the degree of alkylation (i.e., the number of alkyl groups on the amine) affects the pharmacology of the tryptamines. In addition to the degree of alkylation, the nature of each alkyl group itself affects the pharmacology. As a result, many scientists sought ways to develop tryptamine compounds having various combinations of alkyl groups on the amine nitrogen.

It is well established that alkylating primary and secondary amines presents particular synthetic challenges, e.g., controlling the degree of alkylation at the nucleophilic amine. Upon alkylating a primary amine, the resulting secondary amine product is more basic and more nucleophilic. Accordingly, the secondary amine product undergoes alkylation faster than the original starting material, i.e., the primary amine. This makes it difficult or impossible to stop the reaction after a single alkylation regardless of the amount of alkylating agent used.

For example, Xu et al. reported that attempts to synthesize the mono n-propyl compound, compound 12, only resulted in a 3% yield because it goes to the di-n-propyl compound too fast, even at room temperature. Similarly, Xu reported that attempts to make a dimethyl compound, compound 11, by using 2 equivalents of a methylating agent, resulted only in a 10% yield.

As a result of the longstanding problem with using alkyl halides to synthesize secondary and tertiary amines, synthetic chemists use other synthetic methods, e.g., reductive amination rather than nucleophilic substitution of an alkyl halide by an amine.

SUMMARY OF THE INVENTION

This disclosure relates to [2-(5-chloro-1H-indol-3-yl)ethyl](propan-2-yl)azanium iodide (5-chloro-N-isopropyltryptammonium iodide or 5-Cl-NiPT iodide), crystalline 5-Cl-NiPT iodide, and specific crystalline forms thereof. In one embodiment, this disclosure pertains to particular crystalline forms of 5-Cl-NiPT iodide, including crystalline form 1 of 5-Cl-NiPT iodide. In one embodiment, crystalline form 1 of 5-Cl-NiPT iodide is characterized by at least one of: a orthorhombic, $P2_12_12_1$ space group at a temperature of about 297(2) K; unit cell dimensions a=5.9905(3) Å, b=11.2975(5) Å, c=22.7295(12) Å, $\alpha$=90°, $\beta$=90°, and $\gamma$=90°; an X-ray powder diffraction (XRPD) pattern substantially similar to FIG. 13; and an X-ray powder diffraction pattern characterized by at least two peaks selected from 8.7, 18.9, and 20.5° 2θ±0.2° 2θ.

This disclosure further relates to [2-(5-methoxy-1H-indol-3-yl)ethyl](propan-2-yl)azanium iodide (5-methoxy-N-isopropyltryptammonium iodide or 5-MeO-NiPT iodide), crystalline 5-MeO-NiPT iodide, and specific crystalline forms thereof. In one embodiment, this disclosure pertains to particular crystalline forms of 5-MeO-NiPT iodide, including crystalline form 1 of 5-MeO-NiPT iodide. In one embodiment, crystalline form 1 of 5-MeO-NiPT iodide is characterized by at least one of: an orthorhombic, $P2_12_12_1$ space group at a temperature of about 300(2) K; unit cell dimensions a=5.9940(5) Å, b=11.2071(9) Å, c=23.736(2) Å, $\alpha$=90°, $\beta$=90°, and $\gamma$=90°; an X-ray powder diffraction (XRPD) pattern substantially similar to FIG. 14; and an X-ray powder diffraction pattern characterized by at least two peaks selected from 7.4, 8.7, 10.8, and 13.70 2θ±0.2° 2θ.

This disclosure further relates to [2-(5-methyl-1H-indol-3-yl)ethyl](propan-2-yl)azanium iodide (5-methyl-N-isopropyltryptammonium iodide or 5-Me-NiPT iodide), crystalline 5-Me-NiPT iodide, and specific crystalline forms thereof. In one embodiment, this disclosure pertains to particular crystalline forms of 5-Me-NiPT iodide, including crystalline form 1 of 5-Me-NiPT iodide. In one embodiment, crystalline form 1 of 5-Me-NiPT iodide is characterized by at least one of: an orthorhombic, $P2_12_12_1$ space group at a temperature of about 297(2) K; unit cell dimensions a=6.0607(3) Å, b=11.2510(6) Å, c=22.8679(14) Å, $\alpha$=90°, $\beta$=90°, and $\gamma$=90°; an X-ray powder diffraction (XRPD) pattern substantially similar to FIG. 15; and an X-ray powder diffraction pattern characterized by at least two peaks selected from 7.7, 8.8, and 20.3° 2θ±0.2° 2θ.

This disclosure further relates to [2-(2-methyl-1H-indol-3-yl)ethyl](propan-2-yl)azanium iodide (2-methyl-N-isopropyltryptammonium iodide or 2-Me-NiPT iodide), crystalline 2-Me-NiPT iodide, and specific crystalline forms thereof. In one embodiment, this disclosure pertains to particular crystalline forms of 2-Me-NiPT iodide, including crystalline form 1 of 2-Me-NiPT iodide. In one embodiment, crystalline form 1 of 2-Me-NiPT iodide is characterized by at least one of: an orthorhombic, $P2_12_12_1$ space group at a temperature of about 273(2) K; unit cell dimensions a=7.5933(5) Å, b=10.7783(5) Å, c=19.1520(12) Å, $\alpha$=90°, $\beta$=90°, and $\gamma$=90°; an X-ray powder diffraction (XRPD) pattern substantially similar to FIG. 16; and an X-ray powder diffraction pattern characterized by at least two peaks selected from 9.2, 16.4, and 18.1° 2θ±0.2° 2θ.

This disclosure further relates to [2-(7-methyl-1H-indol-3-yl)ethyl](propan-2-yl)azanium iodide (7-methyl-N-isopropyltryptammonium iodide or 7-Me-NiPT iodide), crystalline 7-Me-NiPT iodide, and specific crystalline forms thereof. In one embodiment, this disclosure pertains to particular crystalline forms of 7-Me-NiPT iodide, including crystalline form 1 of 7-Me-NiPT iodide. In one embodiment, crystalline form 1 of 7-Me-NiPT iodide is characterized by at least one of: a monoclinic, $P2_1/n$ space group at a temperature of about 300(2) K; unit cell dimensions a=13.3208(11) Å, b=8.6748(5) Å, c=15.0094(12) Å, $\alpha$=90°, $\beta$=115.070(3°), and $\gamma$=90°; an X-ray powder diffraction (XRPD) pattern substantially similar to FIG. 17; and an X-ray powder diffraction pattern characterized by at least two peaks selected from 7.4, 14.9, and 16.8° 2θ±0.2° 2θ.

This disclosure further relates to [2-(5-fluoro-1H-indol-3-yl)ethyl](propan-2-yl)azanium iodide (5-fluoro-N-isopropyltryptammonium iodide or 5-F-NiPT iodide), crystalline 5-F-NiPT iodide, and specific crystalline forms thereof. In one embodiment, this disclosure pertains to particular crystalline forms of 5-F-NiPT iodide, including crystalline form 1 of 5-F-NiPT iodide. In one embodiment, crystalline form 1 of 5-F-NiPT iodide is characterized by at least one of: an orthorhombic, $P2_12_12_1$ space group at a temperature of about 300(2) K; unit cell dimensions a=5.9493(4) Å, b=11.4462(5) Å, c=21.7601(12) Å, $\alpha$=90°, $\beta$=90°, and $\gamma$=90°; an X-ray powder diffraction (XRPD) pattern substantially similar to FIG. 18; and an X-ray powder diffraction pattern characterized by at least two peaks selected from 8.1, 19.3, and 20.8° 2θ±0.2 2θ.

This disclosure further relates to mono alkyl tryptamine compounds of formula (I):

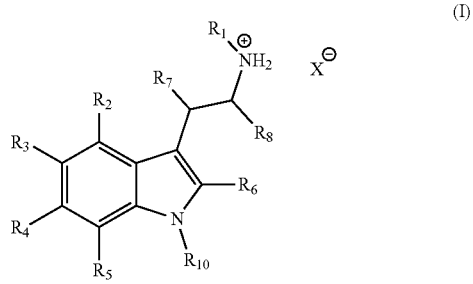

(I)

wherein:
R$_1$ is a secondary alkyl;
R$_2$, R$_3$, R$_4$, R$_5$, R$_6$, R$_7$, R$_8$, and R$_{10}$ are independently selected from hydrogen, optionally substituted C$_1$-C$_6$ alkyl, optionally substituted C$_1$-C$_6$ alkenyl, optionally substituted C$_1$-C$_6$ heteroalkyl, optionally substituted heteroaryl, optionally substituted aryl, halogen, hydroxy, —OR$_9$, —OC(O)R$_9$, —OC(O)OR$_9$, and —OSO$_2$R$_9$;
R$_9$ is independently selected from hydrogen, optionally substituted C$_1$-C$_6$ alkyl, optionally substituted C$_1$-C$_6$ alkenyl, and optionally substituted aryl; and
X$^-$ is a pharmaceutically acceptable halide anion.

This disclosure relates to an improved method of making a monoalkylated (secondary amine) tryptamine analog comprising treating a primary amine (e.g., a tryptamine) with an alkylating agent (e.g., a secondary alkyl halide). In one embodiment, the monoalkylated tryptamine is generated in greater than 50% yield.

The disclosure further relates to a method of making a mono alkyl tryptamine compound of formula (I),

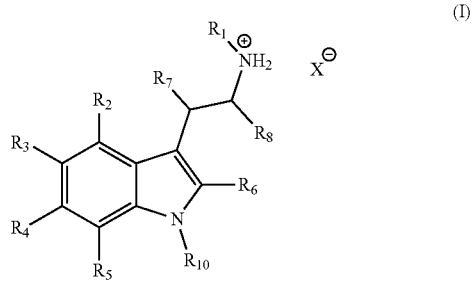

(I)

wherein:
R$_1$ is a secondary alkyl;
R$_2$, R$_3$, R$_4$, R$_5$, R$_6$, R$_7$, R$_8$, and R$_{10}$ are independently selected from hydrogen, optionally substituted C$_1$-C$_6$ alkyl, optionally substituted C$_2$-C$_6$ alkenyl, optionally substituted C$_1$-C$_6$ heteroalkyl, optionally substituted heteroaryl, optionally substituted aryl, halogen, hydroxy, —OR$_9$, —OC(O)R$_9$, —OC(O)OR$_9$, and —OSO$_2$R$_9$;
R$_9$ is independently selected from hydrogen, optionally substituted C$_1$-C$_6$ alkyl, optionally substituted C$_2$-C$_6$ alkenyl, and optionally substituted aryl; and X$^-$ is a pharmaceutically acceptable halide anion;
comprising the step of:
reacting a substituted or unsubstituted tryptamine of formula (II)

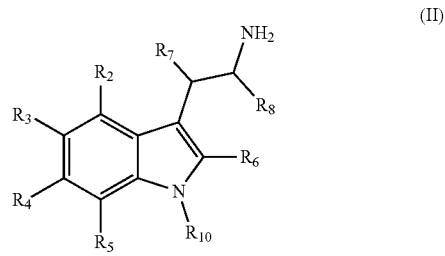

(II)

with an excess of a secondary alkyl halide, R$_1$X;
wherein:
R$_1$ and X of the secondary alkyl halide are identical to how R$_1$ and X are defined in formula (I); and
R$_2$, R$_3$, R$_4$, R$_5$, R$_6$, R$_7$, R$_8$, and R$_{10}$ in formula (II) are identical to how R$_2$, R$_3$, R$_4$, R$_5$, R$_6$, R$_7$, R$_8$ and R$_{10}$ are defined in formula (I). For example, if R$_2$ is hydrogen for formula (I), then R$_2$ for formula (II) is hydrogen also.

This disclosure further relates to dialkyl tryptamine compounds of formula (III):

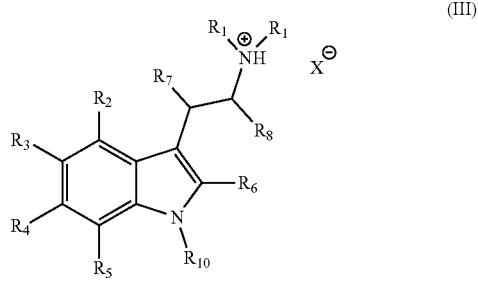

(III)

wherein:
R$_1$ is for each occurrence a secondary alkyl;
R$_2$, R$_3$, R$_4$, R$_5$, R$_6$, R$_7$, R$_8$, and R$_{10}$ are independently selected from hydrogen, optionally substituted C$_1$-C$_6$ alkyl, optionally substituted C$_1$-C$_6$ alkenyl, optionally substituted C$_1$-C$_6$ heteroalkyl, optionally substituted heteroaryl, optionally substituted aryl, halogen, hydroxy, —OR$_9$, —OC(O)R$_9$, —OC(O)OR$_9$, and —OSO$_2$R$_9$;
R$_9$ is independently selected from hydrogen, optionally substituted C$_1$-C$_6$ alkyl, optionally substituted C$_1$-C$_6$ alkenyl, and optionally substituted aryl; and
X$^-$ is a pharmaceutically acceptable halide anion.

This disclosure further relates to an improved method of making a dialkylated (tertiary amine) tryptamine analog comprising treating a primary amine (e.g., a tryptamine) with an alkylating agent (e.g., a secondary alkyl halide). In one embodiment, the dialkylated tryptamine is generated in greater than 50% yield.

The disclosure further relates to a method of making a dialkyl tryptamine compound of formula (III),

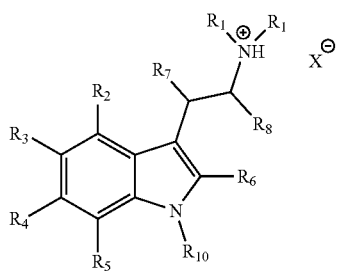

(III)

wherein:
$R_1$ is for each occurrence a secondary alkyl;
$R_2$, $R_3$, $R_4$, $R_5$, $R_6$, $R_7$, $R_8$, and $R_{10}$ are independently selected from hydrogen, optionally substituted $C_1$-$C_6$ alkyl, optionally substituted $C_2$-$C_6$ alkenyl, optionally substituted $C_1$-$C_6$ heteroalkyl, optionally substituted heteroaryl, optionally substituted aryl, halogen, hydroxy, —$OR_9$, —$OC(O)R_9$, —$OC(O)OR_9$, and —$OSO_2R_9$;
$R_9$ is independently selected from hydrogen, optionally substituted $C_1$-$C_6$ alkyl, optionally substituted $C_2$-$C_6$ alkenyl, and optionally substituted aryl; and
$X^-$ is a pharmaceutically acceptable halide anion;
comprising the step of:
reacting a substituted or unsubstituted tryptamine of formula (IV)

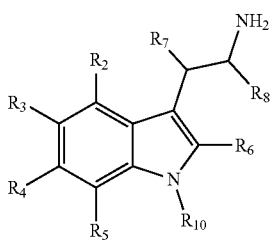

(IV)

with an excess of a secondary alkyl halide, $R_1X$;
wherein:
$R_1$ and X of the secondary alkyl halide are identical to how $R_1$ and X are defined in formula (III); and
$R_2$, $R_3$, $R_4$, $R_5$, $R_6$, $R_7$, $R_8$, and $R_{10}$ in formula (IV) are identical to how $R_2$, $R_3$, $R_4$, $R_5$, $R_6$, $R_7$, $R_8$, and $R_{10}$ are defined in formula (III). For example, if $R_2$ is hydrogen for formula (III), then $R_2$ for formula (IV) is hydrogen also.

The disclosure further relates to a composition comprising 5-Cl-NiPT iodide, crystalline 5-Cl-NiPT iodide, or specific crystalline forms thereof, such as crystalline form 1 of 5-Cl-NiPT iodide, and at least one excipient.

The disclosure further relates to a composition comprising 5-MeO-NiPT iodide, crystalline 5-MeO-NiPT iodide, or specific crystalline forms thereof, such as crystalline form 1 of 5-MeO-NiPT iodide, and at least one excipient.

The disclosure further relates to a composition comprising 5-Me-NiPT iodide, crystalline 5-Me-NiPT iodide, or specific crystalline forms thereof, such as crystalline form 1 of 5-Me-NiPT iodide, and at least one excipient.

The disclosure further relates to a composition comprising 2-Me-NiPT iodide, crystalline 2-Me-NiPT iodide, or specific crystalline forms thereof, such as crystalline form 1 of 2-Me-NiPT iodide, and at least one excipient.

The disclosure further relates to a composition comprising 7-Me-NiPT iodide, crystalline 7-Me-NiPT iodide, or specific crystalline forms thereof, such as crystalline form 1 of 7-Me-NiPT iodide, and at least one excipient.

The disclosure further relates to a composition comprising 5-F-NiPT iodide, crystalline 5-F-NiPT iodide, or specific crystalline forms thereof, such as crystalline form 1 of 5-F-NiPT iodide, and at least one excipient.

The disclosure further relates to a composition comprising a compound of formula (I) or formula (III) according to this disclosure, and at least one excipient.

The disclosure also provides a composition comprising 5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, or specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, and crystalline form 1 of 5-F-NiPT iodide, as a first component and a second component selected from at least one of (a) a serotonergic drug, (b) a purified psilocybin derivative, (c) a purified cannabinoid, (d) a purified terpene, (e) an adrenergic drug, (f) a dopaminergic drug, (g) a monoamine oxidase inhibitor, (h) a purified erinacine, and (i) a purified hericenone; and at least one excipient.

The disclosure further relates to a composition comprising a compound of formula (I) or formula (III) according to this disclosure, as a first component and a second component selected from at least one of (a) a serotonergic drug, (b) a purified psilocybin derivative, (c) a purified cannabinoid, (d) a purified terpene, (e) an adrenergic drug, (f) a dopaminergic drug, (g) a monoamine oxidase inhibitor, (h) a purified erinacine, and (i) a purified hericenone; and at least one excipient.

The disclosure also relates to a method of preventing or treating a psychological disorder comprising the step of administering to a subject in need thereof a therapeutically effective amount of 5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, or specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, and crystalline form 1 of 5-F-NiPT iodide, or a composition according to this disclosure.

The disclosure also relates to a method of preventing or treating a psychological disorder comprising the step of administering to a subject in need thereof a therapeutically effective amount of a compound of formula (I) or formula (III) according to this disclosure.

The disclosure further relates to a method of preventing or treating inflammation and/or pain, preventing or treating a neurological disorder, modulating activity of a mitogen-activated protein kinase (MAPK), modulating neurogenesis, or modulating neurite outgrowth comprising the step of administering to a subject in need thereof a therapeutically effective amount of a compound of 5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, or specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, and crystalline form 1 of 5-F-NiPT iodide, and to administering a pharmaceutical composition or a composition according to the invention.

The disclosure further relates to a method of preventing or treating inflammation and/or pain, preventing or treating a neurological disorder, modulating activity of a mitogen-activated protein kinase (MAPK), modulating neurogenesis, or modulating neurite outgrowth comprising the step of administering to a subject in need thereof a therapeutically effective amount of a compound of formula (I) or formula (III) according to this disclosure.

As used herein, the term "a subject in need thereof" refers to a person requiring a composition to treat a particular disease or condition (e.g., inflammation, pain, a psychological disorder, modulating activity at a receptor, etc.). In one embodiment, the "subject in need thereof" may be identified by analyzing, diagnosing, and/or determining whether the person (or subject) requires the composition for treatment of a particular disease or condition. In one embodiment, identifying a person in need of treatment comprises diagnosing a person with a medical condition, e.g., a neurological disorder, a chemical imbalance, a hereditary condition, etc. In one embodiment, identifying a person in need of treatment comprises performing a psychiatric evaluation. In one embodiment, identifying a person in need of treatment comprises performing a blood test. In one embodiment, identifying a person in need of treatment comprises determining whether a person has a compulsive disorder. In one embodiment, identifying a person in need of treatment comprises self-identifying as having a compulsive disorder.

DETAILED DESCRIPTION

Compounds

Figure 1:
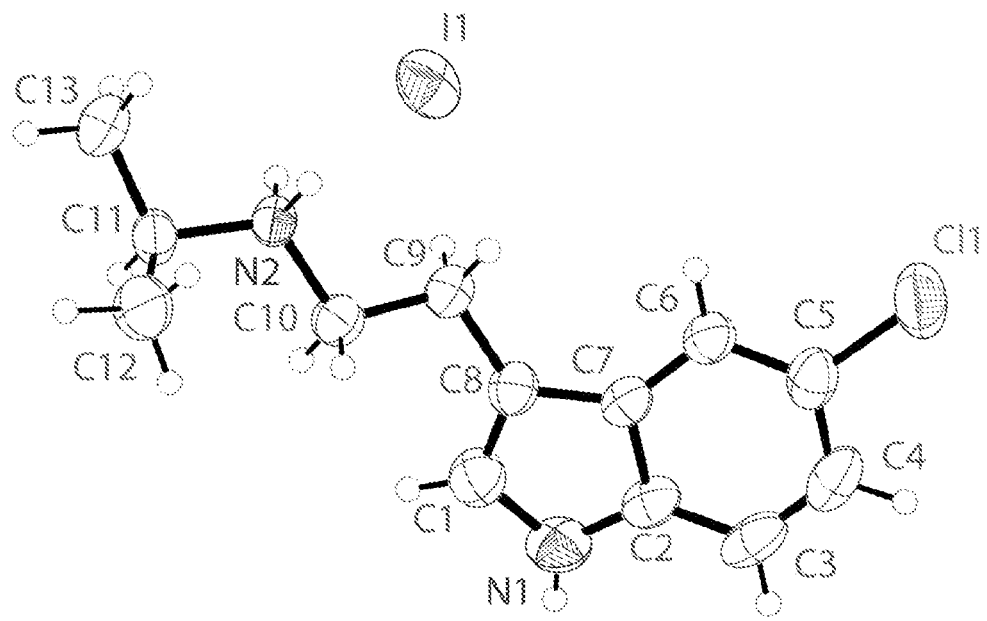
FIG. 1 shows the molecular structure of crystalline form 1 of 5-chloro-N-isopropyltryptammonium iodide.

This disclosure relates to [2-(5-chloro-1H-indol-3-yl)ethyl](propan-2-yl)azanium iodide (5-chloro-N-isopropyltryptammonium iodide or 5-Cl-NiPT iodide), crystalline 5-Cl-NiPT iodide, [2-(5-methoxy-1H-indol-3-yl)ethyl](propan-2-yl)azanium iodide (5-methoxy-N-isopropyltryptammonium iodide or 5-MeO-NiPT iodide), crystalline 5-MeO-NiPT iodide, [2-(5-methyl-1H-indol-3-yl)ethyl](propan-2-yl)azanium iodide (5-methyl-N-isopropyltryptammonium iodide or 5-Me-NiPT iodide), crystalline 5-Me-NiPT iodide, [2-(2-methyl-1H-indol-3-yl)ethyl](propan-2-yl)azanium iodide (2-methyl-N-isopropyltryptammonium iodide or 2-Me-NiPT iodide), crystalline 2-Me-NiPT iodide, [2-(7-methyl-1H-indol-3-yl)ethyl](propan-2-yl)azanium iodide (7-methyl-N-isopropyltryptammonium iodide or 7-Me-NiPT iodide), crystalline 7-Me-NiPT iodide, [2-(5-fluoro-1H-indol-3-yl)ethyl](propan-2-yl)azanium iodide (5-fluoro-N-isopropyltryptammonium iodide or 5-F-NiPT iodide), crystalline 5-F-NiPT iodide, and specific crystalline forms thereof, including crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, and crystalline form 1 of 5-F-NiPT iodide; to pharmaceutical compositions containing 5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, or specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, and crystalline form 1 of 5-F-NiPT iodide, according to the disclosure. The therapeutic uses of 5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, or specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, and crystalline form 1 of 5-F-NiPT iodide, according to the disclosure are described below as well as compositions containing it. 5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, or specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, and crystalline form 1 of 5-F-NiPT iodide, and some exemplary methods used to characterize it are described below.

5-Cl-NiPT iodide has the following chemical formula:

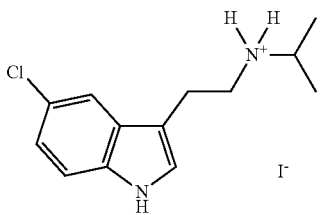 [SMILES: CC(C)[NH2+]CCc1c[nH]c2ccc(Cl)cc12 ; [I-]]

5-MeO-NiPT iodide has the following chemical formula:

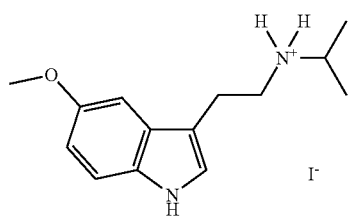 [SMILES: COc1ccc2[nH]cc(CC[NH2+]C(C)C)c2c1 ; [I-]]

5-Me-NiPT iodide has the following chemical formula:

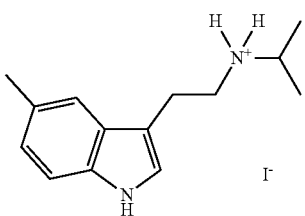 [SMILES: Cc1ccc2[nH]cc(CC[NH2+]C(C)C)c2c1 ; [I-]]

2-Me-NiPT iodide has the following chemical formula:

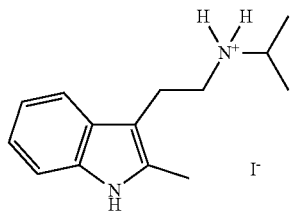 [SMILES: Cc1[nH]c2ccccc2c1CC[NH2+]C(C)C ; [I-]]

7-Me-NiPT iodide has the following chemical formula:

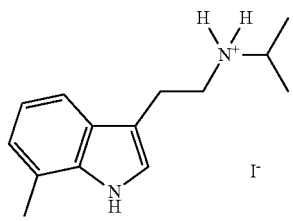 [SMILES: Cc1cccc2c(CC[NH2+]C(C)C)c[nH]c12 ; [I-]]

5-F-NiPT iodide has the following chemical formula:

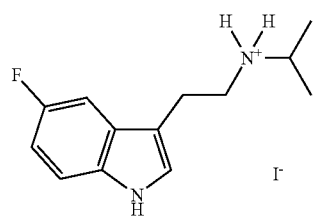 [SMILES: CC(C)[NH2+]CCc1c[nH]c2ccc(F)cc12 ; [I-]]

5-MeO-NiPT iodide, 5-Me-NiPT iodide, 2-Me-NiPT iodide, 7-Me-NiPT iodide, and 5-F-NiPT iodide are compounds of formula (I) and may be prepared by the methods of this disclosure.

This disclosure further relates to a mono alkyl tryptamine compound of formula (I):

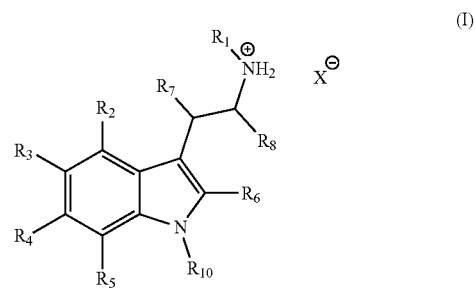

wherein:
$R_1$ is a secondary alkyl;
$R_2$, $R_3$, $R_4$, $R_5$, $R_6$, $R_7$, $R_8$, and $R_{10}$ are independently selected from hydrogen, optionally substituted $C_1$-$C_6$ alkyl, optionally substituted $C_2$-$C_6$ alkenyl, optionally substituted $C_1$-$C_6$ heteroalkyl, optionally substituted heteroaryl, optionally substituted aryl, halogen, hydroxy, —$OR_9$, —$OC(O)R_9$, —$OC(O)OR_9$, and —$OSO_2R_9$;

$R_9$ is independently selected from hydrogen, optionally substituted $C_1$-$C_6$ alkyl, optionally substituted $C_2$-$C_6$ alkenyl, and optionally substituted aryl; and $X^-$ is a pharmaceutically acceptable halide anion.

In formula (I), $R_1$ is a secondary alkyl, wherein a secondary carbon of alkyl group is attached to the amine nitrogen of the mono alkyl tryptamine. $R_1$ may be a straight chain or branched secondary $C_3$-$C_{10}$ alkyl or a substituted or unsubstituted secondary $C_3$-$C_6$ cycloalkyl. $R_1$ may be a straight chain or branched secondary $C_3$-$C_{10}$ alkyl, for example a straight chain secondary $C_3$-$C_{10}$ alkyl, or a substituted or unsubstituted secondary $C_3$-$C_6$ cycloalkyl, for example cyclopropyl, cyclobutyl, cyclopentyl, etc. In some embodiments, $R_1$ may be a straight chain or branched secondary $C_3$-$C_6$ alkyl, for example a straight chain secondary $C_3$-$C_6$ alkyl. $R_1$ may be selected from isopropyl, 2-butyl, 2-pentyl, 3-pentyl, 2-hexyl, 3-hexyl, 2-heptyl, 3-heptyl, 4-heptyl, 2-octyl, 3-octyl, 4-octyl, 2-nonanyl, 3-nonanyl, 4-nonanyl, 5-nonanyl, 2-decanyl, 3-decanyl, 4-decanyl, 5-decanyl, 1-cyclopropyl, 1-cyclobutyl, 2-cyclobutyl, 1-cyclopentyl, 2-cyclopentyl, 3-cyclopentyl, 1-cyclohexyl, 2-cyclohexyl, or 3-cyclohexyl. In other embodiments of the disclosure, $R_1$ is isopropyl.

In formula (I), $R_2$, $R_3$, $R_4$, $R_5$, $R_6$, $R_7$, $R_8$, and $R_{10}$ are independently selected from hydrogen, optionally substituted $C_1$-$C_6$ alkyl, optionally substituted $C_2$-$C_6$ alkenyl, optionally substituted $C_1$-$C_6$ heteroalkyl, optionally substituted heteroaryl, optionally substituted aryl, halogen, hydroxy, —$OR_9$, —$OC(O)R_9$, —$OC(O)OR_9$, and —$OSO_2R_9$. $R_2$, $R_3$, $R_4$, $R_5$, $R_6$, $R_7$, $R_8$, and $R_{10}$ may each independently be hydrogen. $R_2$, $R_3$, $R_4$, $R_5$, $R_6$, $R_7$, $R_8$, and $R_{10}$ may each independently be an optionally substituted straight chain or branched $C_1$-$C_6$ alkyl, for example a straight chain $C_1$-$C_6$ alkyl, or an optionally substituted straight chain or branched $C_2$-$C_6$ alkenyl, for example allyl, 2-butenyl, etc. In some embodiments $R_2$, $R_3$, $R_4$, $R_5$, $R_6$, $R_7$, $R_8$, and $R_{10}$ may each independently be a straight chain or branched $C_1$-$C_4$ alkyl, for example a straight chain $C_1$-$C_4$ alkyl, or a $C_2$-$C_4$ alkenyl. $R_2$, $R_3$, $R_4$, $R_5$, $R_6$, $R_7$, $R_8$, and $R_{10}$ may each independently be an optionally substituted $C_1$-$C_6$-heteroalkyl, including but not limited to alkoxy, alkylthio, and alkylamino. $R_2$, $R_3$, $R_4$, $R_5$, $R_6$, $R_7$, $R_8$, and $R_{10}$ may each independently be an optionally substituted heteroaryl, including, but not limited to, furano, pyridinyl, pyrimidinyl, etc. $R_2$, $R_3$, $R_4$, $R_5$, $R_6$, $R_7$, $R_8$, and $R_{10}$ may each independently be an optionally substituted aryl. An aryl is a 6- to 14-membered aromatic ring, preferably a 6- to 10-membered aromatic ring and includes polycyclic ring systems in which two or more carbon atoms are common to adjoining rings where at least one ring is aromatic. Examples of aryl groups include, but are not limited to phenyl, naphthyl, anthracenyl, and phenantherenyl. An aryl group may be substituted with one or more $C_1$-$C_4$ alkyl or perfluoroalkyl groups, $C_1$-$C_4$ hydroxyalkyl groups, hydroxyl groups, nitro groups or halo groups (e.g., F, Cl, I, or Br). An aryl group may be ortho-, meta-, and/or para-substituted, preferably para-substituted. $R_2$, $R_3$, $R_4$, $R_5$, $R_6$, $R_7$, $R_8$, and $R_{10}$ may each independently be a halogen. Exemplary halogens include fluorine (F), chlorine (Cl), bromine (Br), and iodine (I). $R_2$, $R_3$, $R_4$, $R_5$, $R_6$, $R_7$, $R_8$, and $R_{10}$ may each independently be hydroxy. $R_2$, $R_3$, $R_4$, $R_5$, $R_6$, $R_7$, $R_8$, and $R_{10}$ may each independently be —$OR_9$, —$OC(O)R_9$, —$OC(O)OR_9$, or —$OSO_2R_9$, wherein $R_9$ is independently selected from hydrogen, optionally substituted $C_1$-$C_6$ alkyl, optionally substituted $C_2$-$C_6$ alkenyl, and optionally substituted aryl.

In formula (I), $R_9$ is independently selected from hydrogen, optionally substituted $C_1$-$C_6$ alkyl, optionally substituted $C_2$-$C_6$ alkenyl, and optionally substituted aryl. $R_9$ may be hydrogen. $R_9$ may be an optionally substituted straight chain or branched $C_1$-$C_6$ alkyl, for example a straight chain $C_1$-$C_6$ alkyl, or an optionally substituted straight chain or branched $C_2$-$C_6$ alkenyl, for example allyl, 2-butenyl, etc. In some embodiments $R_9$ may be a straight chain or branched $C_1$-$C_4$ alkyl, for example a straight chain $C_1$-$C_4$ alkyl, or a $C_2$-$C_4$ alkenyl. $R_9$ may be an optionally substituted aryl. An aryl is a 6- to 14-membered aromatic ring, preferably a 6- to 10-membered aromatic ring and includes polycyclic ring systems in which two or more carbon atoms are common to adjoining rings where at least one ring is aromatic. Examples of aryl groups include, but are not limited to phenyl, naphthyl, anthracenyl, and phenantherenyl. An aryl group may be substituted with one or more $C_1$-$C_4$ alkyl or perfluoralkyl groups, $C_1$-$C_4$ hydroxyalkyl groups, hydroxyl groups, nitro groups or halo groups (e.g., F, Cl, I, or Br). An aryl group may be ortho-, meta-, and/or para-substituted, preferably para-substituted.

The pharmaceutically acceptable halide anion, $X^-$, may be chloride ($Cl^-$), bromide ($Br^-$), or iodide ($I^-$).

In one embodiment, $R_1$ is isopropyl.

In one embodiment, the compound of formula (I) is 5-Cl-NiPT iodide.

In one embodiment, the compound of formula (I) is 5-MeO-NiPT iodide.

In one embodiment, the compound of formula (I) is 5-Me-NiPT iodide.

In one embodiment, the compound of formula (I) is 2-Me-NiPT iodide.

In one embodiment, the compound of formula (I) is 7-Me-NiPT iodide.

In one embodiment, the compound of formula (I) is 5-F-NiPT iodide.

In one embodiment, the compound of formula (I) is 5-Br-NiPT iodide.

In one embodiment, the compound of formula (I) is 6-F-NiPT iodide.

In a preferred embodiment, $R_1$ is a straight chain or branched secondary $C_7$-$C_{10}$ alkyl; $R_2$ and $R_3$ are independently selected from optionally substituted $C_1$-$C_6$ alkyl, optionally substituted $C_2$-$C_6$ alkenyl, optionally substituted $C_1$-$C_6$ heteroalkyl, optionally substituted heteroaryl, optionally substituted aryl, halogen, —$OR_9$, —$OC(O)R_9$, —$OC(O)OR_9$, and —$OSO_2R_9$, wherein $R_9$ is hydrogen or optionally substituted $C_2$-$C_6$ alkenyl but —$OR_9$ is not hydroxy; $R_5$, $R_6$, and $R_8$ are independently selected from optionally substituted $C_2$-$C_6$ alkenyl, optionally substituted $C_1$-$C_6$ heteroalkyl, optionally substituted heteroaryl, optionally substituted aryl, halogen, hydroxy, —$OR_9$, —$OC(O)R_9$, —$OC(O)OR_9$, and —$OSO_2R_9$, wherein $R_9$ is independently selected from hydrogen, optionally substituted $C_1$-$C_6$ alkyl, optionally substituted $C_2$-$C_6$ alkenyl, and optionally substituted aryl; and $R_4$, $R_7$, and $R_{10}$ are independently selected from hydrogen, optionally substituted $C_1$-$C_6$ alkyl, optionally substituted $C_2$-$C_6$ alkenyl, optionally substituted $C_1$-$C_6$ heteroalkyl, optionally substituted heteroaryl, optionally substituted aryl, halogen, hydroxy, —$OR_9$, —$OC(O)R_9$, —$OC(O)OR_9$, and —$OSO_2R_9$, wherein $R_9$ is independently selected from hydrogen, optionally substituted $C_1$-$C_6$ alkyl, optionally substituted $C_2$-$C_6$ alkenyl, and optionally substituted aryl.

In one embodiment, $R_1$ may be a straight chain or branched secondary $C_7$ alkyl or $R_1$ may be a straight chain or branched secondary $C_8$ alkyl or $R_1$ may be a straight chain or branched secondary $C_9$ alkyl or $R_1$ may be a straight chain or branched secondary $C_{10}$ alkyl.

In one embodiment, $R_2$ may be optionally substituted $C_1$-$C_6$ alkyl or $R_2$ may be optionally substituted $C_2$-$C_6$ alkenyl or $R_2$ may be optionally substituted $C_1$-$C_6$ heteroalkyl or $R_2$ may be optionally substituted heteroaryl or $R_2$ may be optionally substituted aryl or $R_2$ may be halogen or $R_2$ may be —$OR_9$, wherein $R_9$ is optionally substituted $C_2$-$C_6$ alkenyl, or $R_2$ may be —$OC(O)R_9$, wherein $R_9$ is hydrogen or optionally substituted $C_2$-$C_6$ alkenyl, or $R_2$ may be —$OC(O)OR_9$, wherein $R_9$ is hydrogen or optionally substituted $C_2$-$C_6$ alkenyl, or $R_2$ may be —$OSO_2R_9$, wherein $R_9$ is hydrogen or optionally substituted $C_2$-$C_6$ alkenyl.

In one embodiment, $R_3$ may be optionally substituted $C_1$-$C_6$ alkyl or $R_3$ may be optionally substituted $C_2$-$C_6$ alkenyl or $R_3$ may be optionally substituted $C_1$-$C_6$ heteroalkyl or $R_3$ may be optionally substituted heteroaryl or $R_3$ may be optionally substituted aryl or $R_3$ may be halogen or $R_3$ may be —$OR_9$, wherein $R_9$ is optionally substituted $C_2$-$C_6$ alkenyl, or $R_3$ may be —$OC(O)R_9$, wherein $R_9$ is hydrogen or optionally substituted $C_2$-$C_6$ alkenyl, or $R_3$ may be —$OC(O)OR_9$, wherein $R_9$ is hydrogen or optionally substituted $C_2$-$C_6$ alkenyl, or $R_3$ may be —$OSO_2R_9$, wherein $R_3$ is hydrogen or optionally substituted $C_2$-$C_6$ alkenyl.

In one embodiment, $R_5$ may be optionally substituted $C_2$-$C_6$ alkenyl or $R_5$ may be optionally substituted $C_1$-$C_6$ heteroalkyl or $R_5$ may be optionally substituted heteroaryl or $R_5$ may be optionally substituted aryl or $R_5$ may be halogen or $R_5$ may be hydroxy or $R_5$ may be —$OR_9$, wherein $R_9$ is independently selected from hydrogen, optionally substituted $C_1$-$C_6$ alkyl, optionally substituted $C_2$-$C_6$ alkenyl, and optionally substituted aryl, or $R_5$ may be —$OC(O)R_9$, wherein $R_9$ is independently selected from hydrogen, optionally substituted $C_1$-$C_6$ alkyl, optionally substituted $C_2$-$C_6$ alkenyl, and optionally substituted aryl, or $R_5$ may be —$OC(O)OR_9$, wherein $R_9$ is independently selected from hydrogen, optionally substituted $C_1$-$C_6$ alkyl, optionally substituted $C_2$-$C_6$ alkenyl, and optionally substituted aryl, or $R_5$ may be —$OSO_2R_9$, wherein $R_9$ is independently selected from hydrogen, optionally substituted $C_1$-$C_6$ alkyl, optionally substituted $C_2$-$C_6$ alkenyl, and optionally substituted aryl.

In one embodiment, $R_6$ may be optionally substituted $C_2$-$C_6$ alkenyl or $R_6$ may be optionally substituted $C_1$-$C_6$ heteroalkyl or $R_6$ may be optionally substituted heteroaryl or $R_6$ may be optionally substituted aryl or $R_6$ may be halogen or $R_6$ may be hydroxy or $R_6$ may be —$OR_9$, wherein $R_9$ is independently selected from hydrogen, optionally substituted $C_1$-$C_6$ alkyl, optionally substituted $C_2$-$C_6$ alkenyl, and optionally substituted aryl, or $R_6$ may be —$OC(O)R_9$, wherein $R_9$ is independently selected from hydrogen, optionally substituted $C_1$-$C_6$ alkyl, optionally substituted $C_2$-$C_6$ alkenyl, and optionally substituted aryl, or $R_6$ may be —$OC(O)OR_9$, wherein $R_9$ is independently selected from hydrogen, optionally substituted $C_1$-$C_6$ alkyl, optionally substituted $C_2$-$C_6$ alkenyl, and optionally substituted aryl, or $R_6$ may be —$OSO_2R_9$, wherein $R_9$ is independently selected from hydrogen, optionally substituted $C_1$-$C_6$ alkyl, optionally substituted $C_2$-$C_6$ alkenyl, and optionally substituted aryl.

In one embodiment, $R_8$ may be optionally substituted $C_2$-$C_6$ alkenyl or $R_8$ may be optionally substituted $C_1$-$C_6$ heteroalkyl or $R_8$ may be optionally substituted heteroaryl or $R_8$ may be optionally substituted aryl or $R_8$ may be halogen or $R_8$ may be hydroxy or $R_8$ may be —$OR_9$, wherein $R_9$ is independently selected from hydrogen, optionally substituted $C_1$-$C_6$ alkyl, optionally substituted $C_2$-$C_6$ alkenyl, and optionally substituted aryl, or $R_8$ may be —$OC(O)R_9$, wherein $R_9$ is independently selected from hydrogen, optionally substituted $C_1$-$C_6$ alkyl, optionally substituted $C_2$-$C_6$ alkenyl, and optionally substituted aryl, or $R_a$ may be —$OC(O)OR_9$, wherein $R_9$ is independently selected from hydrogen, optionally substituted $C_1$-$C_6$ alkyl, optionally substituted $C_2$-$C_6$ alkenyl, and optionally substituted aryl, or $R_8$ may be —$OSO_2R_9$, wherein $R_9$ is independently selected from hydrogen, optionally substituted $C_1$-$C_6$ alkyl, optionally substituted $C_2$-$C_6$ alkenyl, and optionally substituted aryl.

In one embodiment, $R_4$ may be hydrogen or $R_4$ may be optionally substituted $C_1$-$C_6$ alkyl or $R_4$ may be optionally substituted $C_2$-$C_6$ alkenyl or $R_4$ may be optionally substituted $C_1$-$C_6$ heteroalkyl or $R_4$ may be optionally substituted heteroaryl or $R_4$ may be optionally substituted aryl or $R_4$ may be halogen or $R_4$ may be hydroxy or $R_4$ may be —$OR_9$, wherein $R_9$ is independently selected from hydrogen, optionally substituted $C_1$-$C_6$ alkyl, optionally substituted $C_2$-$C_6$ alkenyl, and optionally substituted aryl, or $R_4$ may be —$OC(O)R_9$, wherein $R_9$ is independently selected from hydrogen, optionally substituted $C_1$-$C_6$ alkyl, optionally substituted $C_1$-$C_6$ alkenyl, and optionally substituted aryl, or $R_4$ may be —$OC(O)OR_9$, wherein $R_9$ is independently selected from hydrogen, optionally substituted $C_1$-$C_6$ alkyl, optionally substituted $C_2$-$C_6$ alkenyl, and optionally substituted aryl, or $R_4$ may be —$OSO_2R_9$, wherein $R_9$ is independently selected from hydrogen, optionally substituted $C_1$-$C_6$ alkyl, optionally substituted $C_2$-$C_6$ alkenyl, and optionally substituted aryl.

In one embodiment, $R_7$ may be hydrogen or $R_7$ may be optionally substituted $C_1$-$C_6$ alkyl or $R_7$ may be optionally substituted $C_2$-$C_6$ alkenyl or $R_7$ may be optionally substituted $C_1$-$C_6$ heteroalkyl or $R_7$ may be optionally substituted heteroaryl or $R_7$ may be optionally substituted aryl or $R_7$ may be halogen or $R_7$ may be hydroxy or $R_7$ may be —$OR_9$, wherein $R_9$ is independently selected from hydrogen, optionally substituted $C_1$-$C_6$ alkyl, optionally substituted $C_2$-$C_6$ alkenyl, and optionally substituted aryl, or $R_7$ may be —$OC(O)R_9$, wherein $R_9$ is independently selected from hydrogen, optionally substituted $C_1$-$C_6$ alkyl, optionally substituted $C_2$-$C_6$ alkenyl, and optionally substituted aryl, or $R_7$ may be —$OC(O)OR_9$, wherein $R_9$ is independently selected from hydrogen, optionally substituted $C_1$-$C_6$ alkyl, optionally substituted $C_2$-$C_6$ alkenyl, and optionally substituted aryl, or $R_7$ may be —$OSO_2R_9$, wherein $R_9$ is independently selected from hydrogen, optionally substituted $C_1$-$C_6$ alkyl, optionally substituted $C_2$-$C_6$ alkenyl, and optionally substituted aryl.

In one embodiment, $R_{10}$ may be hydrogen or $R_{10}$ may be optionally substituted $C_1$-$C_6$ alkyl or $R_{10}$ may be optionally substituted $C_2$-$C_6$ alkenyl or $R_{10}$ may be optionally substituted $C_1$-$C_6$ heteroalkyl or $R_{10}$ may be optionally substituted heteroaryl or $R_{10}$ may be optionally substituted aryl or $R_{10}$ may be halogen or $R_{10}$ may be hydroxy or $R_{10}$ may be —$OR_9$, wherein $R_9$ is independently selected from hydrogen, optionally substituted $C_1$-$C_6$ alkyl, optionally substituted $C_2$-$C_6$ alkenyl, and optionally substituted aryl, or $R_{10}$ may be —$OC(O)R_9$, wherein $R_9$ is independently selected from hydrogen, optionally substituted $C_1$-$C_6$ alkyl, optionally substituted $C_2$-$C_6$ alkenyl, and optionally substituted aryl, or $R_{10}$ may be —$OC(O)OR_9$, wherein $R_9$ is independently selected from hydrogen, optionally substituted $C_1$-$C_6$ alkyl, optionally substituted $C_1$-$C_6$ alkenyl, and optionally substituted aryl, or $R_{10}$ may be —$OSO_2R_9$, wherein $R_9$ is independently selected from hydrogen, optionally substituted $C_1$-$C_6$ alkyl, optionally substituted $C_2$-$C_6$ alkenyl, and optionally substituted aryl.

This disclosure further relates to a dialkyl tryptamine compound of formula (III):

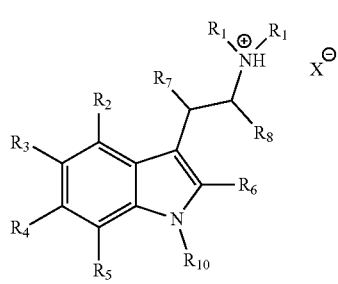

(III)

wherein:
R$_1$ is for each occurrence a secondary alkyl;
R$_2$, R$_3$, R$_4$, R$_5$, R$_6$, R$_7$, R$_8$, and R$_{10}$ are independently selected from hydrogen, optionally substituted C$_1$-C$_6$ alkyl, optionally substituted C$_2$-C$_6$ alkenyl, optionally substituted C$_1$-C$_6$ heteroalkyl, optionally substituted heteroaryl, optionally substituted aryl, halogen, hydroxy, —OR$_9$, —OC(O)R$_9$, —OC(O)OR$_9$, and —OSO$_2$R$_9$;
R$_9$ is independently selected from hydrogen, optionally substituted C$_1$-C$_6$ alkyl, optionally substituted C$_2$-C$_6$ alkenyl, and optionally substituted aryl; and
X$^-$ is a pharmaceutically acceptable halide anion.

In formula (III), R$_1$ is for each occurrence a secondary alkyl, wherein a secondary carbon of each of the alkyl groups is attached to the amine nitrogen of the dialkyl tryptamine. R$_1$ may be a straight chain or branched secondary C$_3$-C$_{10}$ alkyl or a substituted or unsubstituted secondary C$_3$-C$_6$ cycloalkyl. R$_1$ may be a straight chain or branched secondary C$_3$-C$_{10}$ alkyl, for example a straight chain secondary C$_3$-C$_{10}$ alkyl, or a substituted or unsubstituted secondary C$_3$-C$_6$ cycloalkyl, for example cyclopropyl, cyclobutyl, cyclopentyl, etc. In some embodiments, R$_1$ may be a straight chain or branched secondary C$_3$-C$_6$ alkyl, for example a straight chain secondary C$_3$-C$_6$ alkyl. R$_1$ may be selected from isopropyl, 2-butyl, 2-pentyl, 3-pentyl, 2-hexyl, 3-hexyl, 2-heptyl, 3-heptyl, 4-heptyl, 2-octyl, 3-octyl, 4-octyl, 2-nonanyl, 3-nonanyl, 4-nonanyl, 5-nonanyl, 2-decanyl, 3-decanyl, 4-decanyl, 5-decanyl, 1-cyclopropyl, 1-cyclobutyl, 2-cyclobutyl, 1-cyclopentyl, 2-cyclopentyl, 3-cyclopentyl, 1-cyclohexyl, 2-cyclohexyl, or 3-cyclohexyl. In other embodiments of the disclosure, R$_1$ is isopropyl.

In formula (III), R$_2$, R$_3$, R$_4$, R$_5$, R$_6$, R$_7$, R$_8$, and R$_{10}$ are independently selected from hydrogen, optionally substituted C$_1$-C$_6$ alkyl, optionally substituted C$_2$-C$_6$ alkenyl, optionally substituted C$_1$-C$_6$ heteroalkyl, optionally substituted heteroaryl, optionally substituted aryl, halogen, hydroxy, —OR$_9$, —OC(O)R$_9$, —OC(O)OR$_9$, and —OSO$_2$R$_9$. R$_2$, R$_3$, R$_4$, R$_5$, R$_6$, R$_7$, R$_8$, and R$_{10}$ may each independently be hydrogen. R$_2$, R$_3$, R$_4$, R$_5$, R$_6$, R$_7$, R$_8$, and R$_{10}$ may each independently be an optionally substituted straight chain or branched C$_1$-C$_6$ alkyl, for example a straight chain C$_1$-C$_6$ alkyl, or an optionally substituted straight chain or branched C$_2$-C$_6$ alkenyl, for example allyl, 2-butenyl, etc. In some embodiments R$_2$, R$_3$, R$_4$, R$_5$, R$_6$, R$_7$, R$_8$, and R$_{10}$ may each independently be a straight chain or branched C$_1$-C$_4$ alkyl, for example a straight chain C$_1$-C$_4$ alkyl, or a C$_2$-C$_4$ alkenyl. R$_2$, R$_3$, R$_4$, R$_5$, R$_6$, R$_7$, R$_8$, and R$_{10}$ may each independently be an optionally substituted C$_1$-C$_6$-heteroalkyl, including but not limited to alkoxy, alkylthio, and alkylamino. R$_2$, R$_3$, R$_4$, R$_5$, R$_6$, R$_7$, R$_8$, and R$_{10}$ may each independently be an optionally substituted heteroaryl, including, but not limited to, furano, pyridinyl, pyrimidinyl, etc. R$_2$, R$_3$, R$_4$, R$_5$, R$_6$, R$_7$, R$_8$, and R$_{10}$ may each independently be an optionally substituted aryl. An aryl is a 6- to 14-membered aromatic ring, preferably a 6- to 10-membered aromatic ring and includes polycyclic ring systems in which two or more carbon atoms are common to adjoining rings where at least one ring is aromatic. Examples of aryl groups include, but are not limited to phenyl, naphthyl, anthracenyl, and phenantherenyl. An aryl group may be substituted with one or more C$_1$-C$_4$ alkyl or perfluoralkyl groups, C$_1$-C$_4$ hydroxyalkyl groups, hydroxyl groups, nitro groups or halo groups (e.g., F, Cl, I, or Br). An aryl group may be ortho-, meta-, and/or para-substituted, preferably para-substituted. R$_2$, R$_3$, R$_4$, R$_5$, R$_6$, R$_7$, R$_8$, and R$_{10}$ may each independently be a halogen. Exemplary halogens include fluorine (F), chlorine (Cl), bromine (Br), and iodine (I). R$_2$, R$_3$, R$_4$, R$_5$, R$_6$, R$_7$, R$_8$, and R$_{10}$ may each independently be hydroxy. R$_2$, R$_3$, R$_4$, R$_5$, R$_6$, R$_7$, R$_8$, and R$_{10}$ may each independently be —OR$_9$, —OC(O)R$_9$, —OC(O)OR$_9$, or —OSO$_2$R$_9$, wherein R$_9$ is independently selected from hydrogen, optionally substituted C$_1$-C$_6$ alkyl, optionally substituted C$_2$-C$_6$ alkenyl, and optionally substituted aryl.

In formula (III), R$_9$ is independently selected from hydrogen, optionally substituted C$_1$-C$_6$ alkyl, optionally substituted C$_2$-C$_6$ alkenyl, and optionally substituted aryl. R$_9$ may be hydrogen. R$_9$ may be an optionally substituted straight chain or branched C$_1$-C$_6$ alkyl, for example a straight chain C$_1$-C$_6$ alkyl, or an optionally substituted straight chain or branched C$_2$-C$_6$ alkenyl, for example allyl, 2-butenyl, etc. In some embodiments R$_9$ may be a straight chain or branched C$_1$-C$_4$ alkyl, for example a straight chain C$_1$-C$_4$ alkyl, or a C$_2$-C$_4$ alkenyl. R$_9$ may be an optionally substituted aryl. An aryl is a 6- to 14-membered aromatic ring, preferably a 6- to 10-membered aromatic ring and includes polycyclic ring systems in which two or more carbon atoms are common to adjoining rings where at least one ring is aromatic. Examples of aryl groups include, but are not limited to phenyl, naphthyl, anthracenyl, and phenantherenyl. An aryl group may be substituted with one or more C$_1$-C$_4$ alkyl or perfluoralkyl groups, C$_1$-C$_4$ hydroxyalkyl groups, hydroxyl groups, nitro groups or halo groups (e.g., F, Cl, I, or Br). An aryl group may be ortho-, meta-, and/or para-substituted, preferably para-substituted.

The pharmaceutically acceptable halide anion, X$^-$, may be chloride (Cl$^-$), bromide (Br$^-$), or iodide (I$^-$).

In one embodiment, R$_1$ is isopropyl.

In a preferred embodiment, R$_1$ is for each occurrence a straight chain or branched secondary C$_7$-C$_{10}$ alkyl; R$_2$ and R$_3$ are independently selected from optionally substituted C$_1$-C$_6$ alkyl, optionally substituted C$_2$-C$_6$ alkenyl, optionally substituted C$_1$-C$_6$ heteroalkyl, optionally substituted heteroaryl, optionally substituted aryl, halogen, hydroxy, —OR$_9$, —OC(O)R$_9$, —OC(O)OR$_9$, and —OSO$_2$R$_9$, wherein R$_9$ is hydrogen or optionally substituted C$_2$-C$_6$ alkenyl; R$_5$, R$_6$, and R$_8$ are independently selected from optionally substituted C$_2$-C$_6$ alkenyl, optionally substituted C$_1$-C$_6$ heteroalkyl, optionally substituted heteroaryl, optionally substituted aryl, halogen, hydroxy, —OR$_9$, —OC(O)R$_9$, —OC(O)OR$_9$, and —OSO$_2$R$_9$, wherein R$_9$ is independently selected from hydrogen, optionally substituted C$_1$-C$_6$ alkyl, optionally substituted C$_2$-C$_6$ alkenyl, and optionally substituted aryl; and R$_4$, R$_7$, and R$_{10}$ are independently selected from hydrogen, optionally substituted C$_1$-C$_6$ alkyl, optionally substituted C$_2$-C$_6$ alkenyl, optionally substituted C$_1$-C$_6$ heteroalkyl, optionally substituted heteroaryl, optionally substituted aryl, halogen, hydroxy, —$OR_9$, —$OC(O)R_9$, —$OC(O)OR_9$, and —$OSO_2R_9$, wherein $R_9$ is independently selected from hydrogen, optionally substituted $C_1$-$C_6$ alkyl, optionally substituted $C_2$-$C_6$ alkenyl, and optionally substituted aryl.

In one embodiment, $R_1$ for each occurrence may be a straight chain or branched secondary $C_7$ alkyl or $R_1$ for each occurrence may be a straight chain or branched secondary $C_8$ alkyl or $R_1$ for each occurrence may be a straight chain or branched secondary $C_9$ alkyl or $R_1$ for each occurrence may be a straight chain or branched secondary $C_{10}$ alkyl.

In one embodiment, $R_2$ may be optionally substituted $C_1$-$C_6$ alkyl or $R_2$ may be optionally substituted $C_2$-$C_6$ alkenyl or $R_2$ may be optionally substituted $C_1$-$C_6$ heteroalkyl or $R_2$ may be optionally substituted heteroaryl or $R_2$ may be optionally substituted aryl or $R_2$ may be halogen or $R_2$ may be hydroxy or $R_2$ may be —$OR_9$, wherein $R_9$ is hydrogen or optionally substituted $C_2$-$C_6$ alkenyl or $R_2$ may be —$OC(O)R_9$, wherein $R_9$ is hydrogen or optionally substituted $C_2$-$C_6$ alkenyl, or $R_2$ may be —$OC(O)OR_9$, wherein $R_9$ is hydrogen or optionally substituted $C_2$-$C_6$ alkenyl, or $R_2$ may be and —$OSO_2R_9$, wherein $R_9$ is hydrogen or optionally substituted $C_2$-$C_6$ alkenyl.

In one embodiment, $R_3$ may be optionally substituted $C_1$-$C_6$ alkyl or $R_3$ may be optionally substituted $C_2$-$C_6$ alkenyl or $R_3$ may be optionally substituted $C_1$-$C_6$ heteroalkyl or $R_3$ may be optionally substituted heteroaryl or $R_3$ may be optionally substituted aryl or $R_3$ may be hydroxy or $R_3$ may be halogen or $R_3$ may be —$OR_9$, wherein $R_9$ is hydrogen or optionally substituted $C_2$-$C_6$ alkenyl, or $R_3$ may be —$OC(O)R_9$, wherein $R_9$ is hydrogen or optionally substituted $C_2$-$C_6$ alkenyl, or $R_3$ may be —$OC(O)OR_9$, wherein $R_9$ is hydrogen or optionally substituted $C_2$-$C_6$ alkenyl, or $R_3$ may be and —$OSO_2R_9$, wherein $R_3$ is hydrogen or optionally substituted $C_2$-$C_6$ alkenyl.

In one embodiment, $R_5$ may be optionally substituted $C_2$-$C_6$ alkenyl or $R_5$ may be optionally substituted $C_1$-$C_6$ heteroalkyl or $R_5$ may be optionally substituted heteroaryl or $R_5$ may be optionally substituted aryl or $R_5$ may be halogen or $R_5$ may be hydroxy or $R_5$ may be —$OR_9$, wherein $R_9$ is independently selected from hydrogen, optionally substituted $C_1$-$C_6$ alkyl, optionally substituted $C_2$-$C_6$ alkenyl, and optionally substituted aryl, or $R_5$ may be —$OC(O)R_9$, wherein $R_9$ is independently selected from hydrogen, optionally substituted $C_1$-$C_6$ alkyl, optionally substituted $C_2$-$C_6$ alkenyl, and optionally substituted aryl, or $R_5$ may be —$OC(O)OR_9$, wherein $R_9$ is independently selected from hydrogen, optionally substituted $C_1$-$C_6$ alkyl, optionally substituted $C_2$-$C_6$ alkenyl, and optionally substituted aryl, or $R_5$ may be —$OSO_2R_9$, wherein $R_9$ is independently selected from hydrogen, optionally substituted $C_1$-$C_6$ alkyl, optionally substituted $C_2$-$C_6$ alkenyl, and optionally substituted aryl.

In one embodiment, $R_6$ may be optionally substituted $C_2$-$C_6$ alkenyl or $R_6$ may be optionally substituted $C_1$-$C_6$ heteroalkyl or $R_6$ may be optionally substituted heteroaryl or $R_6$ may be optionally substituted aryl or $R_6$ may be halogen or $R_6$ may be hydroxy or $R_6$ may be —$OR_9$, wherein $R_9$ is independently selected from hydrogen, optionally substituted $C_1$-$C_6$ alkyl, optionally substituted $C_2$-$C_6$ alkenyl, and optionally substituted aryl, or $R_6$ may be —$OC(O)R_9$, wherein $R_9$ is independently selected from hydrogen, optionally substituted $C_1$-$C_6$ alkyl, optionally substituted $C_2$-$C_6$ alkenyl, and optionally substituted aryl, or $R_6$ may be —$OC(O)OR_9$, wherein $R_9$ is independently selected from hydrogen, optionally substituted $C_1$-$C_6$ alkyl, optionally substituted $C_2$-$C_6$ alkenyl, and optionally substituted aryl, or $R_6$ may be —$OSO_2R_9$, wherein $R_9$ is independently selected from hydrogen, optionally substituted $C_1$-$C_6$ alkyl, optionally substituted $C_2$-$C_6$ alkenyl, and optionally substituted aryl.

In one embodiment, $R_8$ may be optionally substituted $C_2$-$C_6$ alkenyl or $R_8$ may be optionally substituted $C_1$-$C_6$ heteroalkyl or $R_8$ may be optionally substituted heteroaryl or $R_8$ may be optionally substituted aryl or $R_8$ may be halogen or $R_8$ may be hydroxy or $R_8$ may be —$OR_9$, wherein $R_9$ is independently selected from hydrogen, optionally substituted $C_1$-$C_6$ alkyl, optionally substituted $C_2$-$C_6$ alkenyl, and optionally substituted aryl, or $R_8$ may be —$OC(O)R_9$, wherein $R_9$ is independently selected from hydrogen, optionally substituted $C_1$-$C_6$ alkyl, optionally substituted $C_2$-$C_6$ alkenyl, and optionally substituted aryl, or $R_8$ may be —$OC(O)OR_9$, wherein $R_9$ is independently selected from hydrogen, optionally substituted $C_1$-$C_6$ alkyl, optionally substituted $C_2$-$C_6$ alkenyl, and optionally substituted aryl, or $R_8$ may be —$OSO_2R_9$, wherein $R_9$ is independently selected from hydrogen, optionally substituted $C_1$-$C_6$ alkyl, optionally substituted $C_2$-$C_6$ alkenyl, and optionally substituted aryl.

In one embodiment, $R_4$ may be hydrogen or $R_4$ may be optionally substituted $C_1$-$C_6$ alkyl or $R_4$ may be optionally substituted $C_2$-$C_6$ alkenyl or $R_4$ may be optionally substituted $C_1$-$C_6$ heteroalkyl or $R_4$ may be optionally substituted heteroaryl or $R_4$ may be optionally substituted aryl or $R_4$ may be halogen or $R_4$ may be hydroxy or $R_4$ may be —$OR_9$, wherein $R_9$ is independently selected from hydrogen, optionally substituted $C_1$-$C_6$ alkyl, optionally substituted $C_2$-$C_6$ alkenyl, and optionally substituted aryl, or $R_4$ may be —$OC(O)R_9$, wherein $R_9$ is independently selected from hydrogen, optionally substituted $C_1$-$C_6$ alkyl, optionally substituted $C_2$-$C_6$ alkenyl, and optionally substituted aryl, or $R_4$ may be —$OC(O)OR_9$, wherein $R_9$ is independently selected from hydrogen, optionally substituted $C_1$-$C_6$ alkyl, optionally substituted $C_2$-$C_6$ alkenyl, and optionally substituted aryl, or $R_4$ may be —$OSO_2R_9$, wherein $R_9$ is independently selected from hydrogen, optionally substituted $C_1$-$C_6$ alkyl, optionally substituted $C_2$-$C_6$ alkenyl, and optionally substituted aryl.

In one embodiment, $R_7$ may be hydrogen or $R_7$ may be optionally substituted $C_1$-$C_6$ alkyl or $R_7$ may be optionally substituted $C_2$-$C_6$ alkenyl or $R_7$ may be optionally substituted $C_1$-$C_6$ heteroalkyl or $R_7$ may be optionally substituted heteroaryl or $R_7$ may be optionally substituted aryl or $R_7$ may be halogen or $R_7$ may be hydroxy or $R_7$ may be —$OR_9$, wherein $R_9$ is independently selected from hydrogen, optionally substituted $C_1$-$C_6$ alkyl, optionally substituted $C_2$-$C_6$ alkenyl, and optionally substituted aryl, or $R_7$ may be —$OC(O)R_9$, wherein $R_9$ is independently selected from hydrogen, optionally substituted $C_1$-$C_6$ alkyl, optionally substituted $C_2$-$C_6$ alkenyl, and optionally substituted aryl, or $R_7$ may be —$OC(O)OR_9$, wherein $R_9$ is independently selected from hydrogen, optionally substituted $C_1$-$C_6$ alkyl, optionally substituted $C_2$-$C_6$ alkenyl, and optionally substituted aryl, or $R_7$ may be —$OSO_2R_9$, wherein $R_9$ is independently selected from hydrogen, optionally substituted $C_1$-$C_6$ alkyl, optionally substituted $C_2$-$C_6$ alkenyl, and optionally substituted aryl.

In one embodiment, $R_{10}$ may be hydrogen or $R_{10}$ may be optionally substituted $C_1$-$C_6$ alkyl or $R_{10}$ may be optionally substituted $C_2$-$C_6$ alkenyl or $R_{10}$ may be optionally substituted $C_1$-$C_6$ heteroalkyl or $R_{10}$ may be optionally substituted heteroaryl or $R_{10}$ may be optionally substituted aryl or $R_{10}$ may be halogen or $R_{10}$ may be hydroxy or $R_{10}$ may be —$OR_9$, wherein $R_9$ is independently selected from hydrogen, optionally substituted $C_1$-$C_6$ alkyl, optionally substituted $C_2$-$C_6$ alkenyl, and optionally substituted aryl, or $R_{10}$ may be —OC(O)$R_9$, wherein $R_9$ is independently selected from hydrogen, optionally substituted $C_1$-$C_6$ alkyl, optionally substituted $C_2$-$C_6$ alkenyl, and optionally substituted aryl, or $R_{10}$ may be —OC(O)O$R_9$, wherein $R_9$ is independently selected from hydrogen, optionally substituted $C_1$-$C_6$ alkyl, optionally substituted $C_2$-$C_6$ alkenyl, and optionally substituted aryl, or $R_{10}$ may be —OSO$_2$$R_9$, wherein $R_9$ is independently selected from hydrogen, optionally substituted $C_1$-$C_6$ alkyl, optionally substituted $C_2$-$C_6$ alkenyl, and optionally substituted aryl.

Method of Making Compounds of this Disclosure

This disclosure relates to a method of making a secondary amine (e.g., a mono alkyl tryptamine) comprising reacting a primary amine (e.g., tryptamine) with excess of an alkylating agent (e.g., a secondary alkyl halide). In one embodiment, the monoalkylated tryptamine is generated in greater than 50% yield.

This disclosure further relates to a method of making a tertiary amine (e.g., a dialkyl tryptamine) comprising treating a primary amine (e.g., a tryptamine) with an alkylating agent (e.g., a secondary alkyl halide). In one embodiment, the dialkylated tryptamine is generated in greater than 50% yield.

In one embodiment of the disclosure, the secondary amine is a mono alkyl tryptamine. The alkyl group attached to the amine nitrogen of the mono alkyl tryptamine may be a secondary alkyl, wherein a secondary carbon of alkyl group is attached to the amine nitrogen of the mono alkyl tryptamine, such as a straight chain or branched secondary $C_3$-$C_{10}$ alkyl or a substituted or unsubstituted secondary $C_3$-$C_6$ cycloalkyl. The alkyl group attached to the amine nitrogen of the mono alkyl tryptamine may be a straight chain or branched secondary $C_3$-$C_{10}$ alkyl, for example a straight chain secondary $C_3$-$C_{10}$ alkyl, or a substituted or unsubstituted secondary $C_3$-$C_6$ cycloalkyl, for example cyclopropyl, cyclobutyl, cyclopentyl, etc. In some embodiments, the alkyl group attached to the amine nitrogen of the mono alkyl tryptamine may be a straight chain or branched secondary $C_3$-$C_6$ alkyl, for example a straight chain secondary $C_3$-$C_6$ alkyl. The secondary alkyl group attached to the amine nitrogen of the mono alkyl tryptamine may be selected from isopropyl, 2-butyl, 2-pentyl, 3-pentyl, 2-hexyl, 3-hexyl, 2-heptyl, 3-heptyl, 4-heptyl, 2-octyl, 3-octyl, 4-octyl, 2-nonanyl, 3-nonanyl, 4-nonanyl, 5-nonanyl, 2-decanyl, 3-decanyl, 4-decanyl, 5-decanyl, 1-cyclopropyl, 1-cyclobutyl, 2-cyclobutyl, 1-cyclopentyl, 2-cyclopentyl, 3-cyclopentyl, 1-cyclohexyl, 2-cyclohexyl, or 3-cyclohexyl. In other embodiments of the disclosure, the mono alkyl tryptamine is a substituted or unsubstituted N-isopropyltryptamine.

In one embodiment of the disclosure, the tertiary amine is a dialkyl tryptamine. The two alkyl groups attached to the amine nitrogen of the dialkyl tryptamine may be secondary alkyls, wherein a secondary carbon of each of the alkyl groups is attached to the amine nitrogen of the dialkyl tryptamine, such as straight chain or branched secondary $C_3$-$C_{10}$ alkyls or a substituted or unsubstituted secondary $C_3$-$C_6$ cycloalkyl, wherein the two alkyl groups attached to the amine nitrogen of the dialkyl tryptamine are the same. The two alkyl groups attached to the amine nitrogen of the dialkyl tryptamine may be straight chain or branched secondary $C_3$-$C_{10}$ alkyls, for example straight chain secondary $C_3$-$C_{10}$ alkyls, or a substituted or unsubstituted secondary $C_3$-$C_6$ cycloalkyl, for example cyclopropyl, cyclobutyl, cyclopentyl, etc. In some embodiments, the two alkyl groups attached to the amine nitrogen of the mono alkyl tryptamine may be straight chain or branched secondary $C_3$-$C_6$ alkyls, for example straight chain secondary $C_3$-$C_6$ alkyls. The two secondary alkyl groups attached to the amine nitrogen of the dialkyl tryptamine may be selected from isopropyl, 2-butyl, 2-pentyl, 3-pentyl, 2-hexyl, 3-hexyl, 2-heptyl, 3-heptyl, 4-heptyl, 2-octyl, 3-octyl, 4-octyl, 2-nonanyl, 3-nonanyl, 4-nonanyl, 5-nonanyl, 2-decanyl, 3-decanyl, 4-decanyl, 5-decanyl, 1-cyclopropyl, 1-cyclobutyl, 2-cyclobutyl, 1-cyclopentyl, 2-cyclopentyl, 3-cyclopentyl, 1-cyclohexyl, 2-cyclohexyl, or 3-cyclohexyl. In other embodiments of the disclosure, the dialkyl tryptamine is a substituted or unsubstituted N,N-di-n-isopropyltryptamine.

In one embodiment of the disclosure, the primary amine is a tryptamine analog. In one embodiment of the disclosure, the primary amine is a substituted or unsubstituted tryptamine.

In one embodiment of the disclosure, the alkylating agent is a secondary alkyl halide, wherein the halide is attached to a secondary carbon of the alkyl group. The secondary alkyl halide may be a straight chain or branched secondary $C_3$-$C_{10}$ alkyl halide or a substituted or unsubstituted secondary $C_3$-$C_6$ cycloalkyl halide. In one embodiment of the disclosure, the secondary alkyl of the secondary alkyl halide is the same as the alkyl group attached to the amine nitrogen of the mono alkyl tryptamine. In other embodiments of the disclosure, the secondary alkyl of the secondary alkyl halide is the same as the two alkyl groups attached to the amine nitrogen of the dialkyl tryptamine. The secondary alkyl halide may be a straight chain or branched secondary $C_3$-$C_{10}$ alkyl halide, for example a straight chain secondary $C_3$-$C_{10}$ alkyl halide, or a substituted or unsubstituted secondary $C_3$-$C_6$ cycloalkyl halide, for example cyclopropyl halide, cyclobutyl halide, cyclopentyl halide, etc. In some embodiments, the secondary alkyl halide may be a straight chain or branched secondary $C_3$-$C_6$ alkyl halide, for example a straight chain secondary $C_3$-$C_6$ alkyl halide. The secondary alkyl halide may be selected from an isopropyl halide, a 2-halide-butane, a 2-halide-pentane, a 3-halide-pentane, a 2-halide-hexane, a 3-halide-hexane, a 2-halide-heptane, a 3-halide-heptane, a 4-halide-heptane, a 2-halide-octane, a 3-halide-octane, a 4-halide-octane, a 2-halide-nonane, a 3-halide-nonane, a 4-halide-nonane, a 5-halide-nonane, a 2-halide-decane, a 3-halide-decane, a 4-halide-decane, a 5-halide-decane, a 1-halide-cyclopropane, a 1-halide-cyclobutane, a 2-halide-cyclobutane, a 1-halide-cyclopentane, a 2-halide-cyclopentane, a 3-halide-cyclopentane, a 1-halide-cyclohexane, a 2-halide-cyclohexane, or a 3-halide-cyclohexane. Exemplary halides include chloride (Cl⁻), bromide (Br⁻), and iodide (I⁻). In some embodiments of the disclosure, the secondary alkyl halide is an isopropyl iodide, 2-iodo-butane, 2-iodo-pentane, 3-iodo-pentane, 2-iodo-hexane, 3-iodo-hexane, 2-iodo-heptane, 3-iodo-heptane, 4-iodo-heptane, 2-iodo-octane, 3-iodo-octane, 4-iodo-octane, 2-iodo-nonane, 3-iodo-nonane, 4-iodo-nonane, 5-iodo-nonane, 2-iodo-decane, 3-iodo-decane, 4-iodo-decane, 5-iodo-decane, 1-iodo-cyclopropane, 1-iodo-cyclobutane, 2-iodo-cyclobutane, 1-iodo-cyclopentane, 2-iodo-cyclopentane, 3-iodo-cyclopentane, 1-iodo-cyclohexane, 2-iodo-cyclohexane, or 3-iodo-cyclohexane. In other embodiments of the disclosure, the secondary alkyl halide is isopropyl iodide.

In one embodiment, the secondary alkyl halide may be represented by a compound of formula (V):

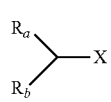

(V)

wherein:
X is selected from the group consisting of chloride (Cl⁻), bromide (Br⁻), and iodide (I⁻);
one of $R_a$ and $R_b$ is a straight chain or branched $C_1$-$C_5$ alkyl and the other of $R_a$ and $R_b$ is a straight chain or branched $C_1$-$C_5$ alkyl; or $R_a$ and $R_b$ together form a substituted or unsubstituted $C_3$-$C_6$ cycloalkyl.

In one embodiment of the disclosure, to make a mono alkyl tryptamine of the disclosure, the primary amine is treated with an excess of a secondary alkyl halide and the solution is refluxed for about 12-24 hours. In one embodiment of the disclosure, the primary amine is treated with an excess of a secondary alkyl halide at a temperature sufficient to affect one alkylation, which can be monitored spectroscopically, e.g., by NMR. In some embodiments, excess is 5 equivalents, 6 equivalents, 7 equivalents, 8 equivalents, 9 equivalents, 10 equivalents, 11 equivalents, 12 equivalents, 13 equivalents, 14 equivalents, 15 equivalents, 16 equivalents, 17 equivalents, 18 equivalents, 19 equivalents, 20 equivalents, 21 equivalents, 22 equivalents, 23 equivalents, 24 equivalents, or 25 equivalents. In some embodiments of the disclosure, the primary amine is treated with an alkylating agent and the solution is refluxed for about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours. In one embodiment of the disclosure, the solution is refluxed in isopropanol.

In other embodiments of the disclosure, to make a dialkyl tryptamine of the disclosure, the primary amine is treated with an excess of a secondary alkyl halide and the solution is refluxed for about 36-72 hours. In one embodiment of the disclosure, the primary amine is treated with an excess of a secondary alkyl halide at a temperature sufficient to affect two alkylations, which can be monitored spectroscopically, e.g., by NMR. In some embodiments, excess is 5 equivalents, 6 equivalents, 7 equivalents, 8 equivalents, 9 equivalents, 10 equivalents, 11 equivalents, 12 equivalents, 13 equivalents, 14 equivalents, 15 equivalents, 16 equivalents, 17 equivalents, 18 equivalents, 19 equivalents, 20 equivalents, 21 equivalents, 22 equivalents, 23 equivalents, 24 equivalents, or 25 equivalents. In some embodiments of the disclosure, the primary amine is treated with an alkylating agent and the solution is refluxed for about 36 hours, about 37 hours, about 38 hours, about 39 hours, about 40 hours, about 41 hours, about 42 hours, about 43 hours, about 44 hours, about 45 hours, about 46 hours, about 47 hours, about 48 hours, about 49 hours, about 50 hours, about 51 hours, about 52 hours, about 53 hours, about 54 hours, about 55 hours, about 56 hours, about 57 hours, about 58 hours, about 59 hours, about 60 hours, about 61 hours, about 62 hours, about 63 hours, about 64 hours, about 65 hours, about 66 hours, about 67 hours, about 68 hours, about 69 hours, about 70 hours, about 71 hours, or about 72 hours. In one embodiment of the disclosure, the solution is refluxed in isopropanol.

This disclosure further relates to a method of making a mono alkyl tryptamine compound of formula (I),

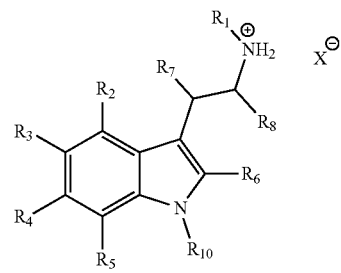

(I)

wherein:
$R_1$ is a secondary alkyl;
$R_2$, $R_3$, $R_4$, $R_5$, $R_6$, $R_7$, $R_8$, and $R_{10}$ are independently selected from hydrogen, optionally substituted $C_1$-$C_6$ alkyl, optionally substituted $C_2$-$C_6$ alkenyl, optionally substituted $C_1$-$C_6$ heteroalkyl, optionally substituted heteroaryl, optionally substituted aryl, halogen, hydroxy, —$OR_9$, —$OC(O)R_9$, —$OC(O)OR_9$, and —$OSO_2R_9$;
$R_9$ is independently selected from hydrogen, optionally substituted $C_1$-$C_6$ alkyl, optionally substituted $C_2$-$C_6$ alkenyl, and optionally substituted aryl; and
$X^-$ is a pharmaceutically acceptable halide anion;
comprising the step of:
reacting a substituted or unsubstituted tryptamine of formula (II)

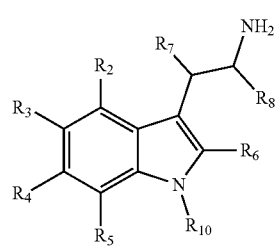

(II)

with an excess of a secondary alkyl halide, $R_1X$;
wherein:
$R_1$ and X of the secondary alkyl halide are identical to how $R_1$ and X are defined in formula (I); and
$R_2$, $R_3$, $R_4$, $R_5$, $R_6$, $R_7$, $R_8$, and $R_{10}$ in formula (II) are identical to how $R_2$, $R_3$, $R_4$, $R_5$, $R_6$, $R_7$, $R_8$, and $R_{10}$ are defined in formula (I). For example, if $R_2$ is hydrogen for formula (I), then $R_2$ for formula (II) is hydrogen also.

In formula (I), $R_1$ is a secondary alkyl, wherein a secondary carbon of alkyl group is attached to the amine nitrogen of the mono alkyl tryptamine. R may be a straight chain or branched secondary $C_3$-$C_{10}$ alkyl or a substituted or unsubstituted secondary $C_3$-$C_6$ cycloalkyl. $R_1$ may be a straight chain or branched secondary $C_3$-$C_{10}$ alkyl, for example a straight chain secondary $C_3$-$C_{10}$ alkyl, or a substituted or unsubstituted secondary $C_3$-$C_6$ cycloalkyl, for example cyclopropyl, cyclobutyl, cyclopentyl, etc. In some embodiments, $R_1$ may be a straight chain or branched secondary $C_3$-$C_6$ alkyl, for example a straight chain secondary $C_3$-$C_6$ alkyl. $R_1$ may be selected from isopropyl, 2-butyl, 2-pentyl, 3-pentyl, 2-hexyl, 3-hexyl, 2-heptyl, 3-heptyl, 4-heptyl, 2-octyl, 3-octyl, 4-octyl, 2-nonanyl, 3-nonanyl, 4-nonanyl, 5-nonanyl, 2-decanyl, 3-decanyl, 4-decanyl, 5-decanyl, 1-cyclopropyl, 1-cyclobutyl, 2-cyclobutyl, 1-cyclopentyl, 2-cyclopentyl, 3-cyclopentyl, 1-cyclohexyl, 2-cyclohexyl, or 3-cyclohexyl. In other embodiments of the disclosure, $R_1$ is isopropyl.

In formula (I), $R_2$, $R_3$, $R_4$, $R_5$, $R_6$, $R_7$, $R_8$, and $R_{10}$ are independently selected from hydrogen, optionally substituted $C_1$-$C_6$ alkyl, optionally substituted $C_2$-$C_6$ alkenyl, optionally substituted $C_1$-$C_6$ heteroalkyl, optionally substituted heteroaryl, optionally substituted aryl, halogen, hydroxy, —$OR_9$, —$OC(O)R_9$, —$OC(O)OR_9$, and —$OSO_2R_9$. $R_2$, $R_3$, $R_4$, $R_5$, $R_6$, $R_7$, $R_8$, and $R_{10}$ may each independently be hydrogen. $R_2$, $R_3$, $R_4$, $R_5$, $R_6$, $R_7$, $R_8$, and $R_{10}$ may each independently be an optionally substituted straight chain or branched $C_1$-$C_6$ alkyl, for example a straight chain $C_1$-$C_6$ alkyl, or an optionally substituted straight chain or branched $C_2$-$C_6$ alkenyl, for example allyl, 2-butenyl, etc. In some embodiments $R_2$, $R_3$, $R_4$, $R_5$, $R_6$, $R_7$, $R_8$, and $R_{10}$ may each independently be a straight chain or branched $C_1$-$C_4$ alkyl, for example a straight chain $C_1$-$C_4$ alkyl, or a $C_2$-$C_4$ alkenyl. $R_2$, $R_3$, $R_4$, $R_5$, $R_6$, $R_7$, $R_8$, and $R_{10}$ may each independently be an optionally substituted $C_1$-$C_6$-heteroalkyl, including but not limited to alkoxy, alkylthio, and alkylamino. $R_2$, $R_3$, $R_4$, $R_5$, $R_6$, $R_7$, $R_8$, and $R_{10}$ may each independently be an optionally substituted heteroaryl, including, but not limited to, furano, pyridinyl, pyrimidinyl, etc. $R_2$, $R_3$, $R_4$, $R_5$, $R_6$, $R_7$, $R_8$, and $R_{10}$ may each independently be an optionally substituted aryl. An aryl is a 6- to 14-membered aromatic ring, preferably a 6- to 10-membered aromatic ring and includes polycyclic ring systems in which two or more carbon atoms are common to adjoining rings where at least one ring is aromatic. Examples of aryl groups include, but are not limited to phenyl, naphthyl, anthracenyl, and phenantherenyl. An aryl group may be substituted with one or more $C_1$-$C_4$ alkyl or perfluoralkyl groups, $C_1$-$C_4$ hydroxyalkyl groups, hydroxyl groups, nitro groups or halo groups (e.g., F, Cl, I, or Br). An aryl group may be ortho-, meta-, and/or para-substituted, preferably para-substituted. $R_2$, $R_3$, $R_4$, $R_5$, $R_6$, $R_7$, $R_8$, and $R_{10}$ may each independently be a halogen. Exemplary halogens include fluorine (F), chlorine (Cl), bromine (Br), and iodine (I). $R_2$, $R_3$, $R_4$, $R_5$, $R_6$, $R_7$, $R_8$, and $R_{10}$ may each independently be hydroxy. $R_2$, $R_3$, $R_4$, $R_5$, $R_6$, $R_7$, $R_8$, and $R_{10}$ may each independently be —$OR_9$, —$OC(O)R_9$, —$OC(O)OR_9$, or —$OSO_2R_9$, wherein $R_9$ is independently selected from hydrogen, optionally substituted $C_1$-$C_6$ alkyl, optionally substituted $C_2$-$C_6$ alkenyl, and optionally substituted aryl.

In formula (I), $R_9$ is independently selected from hydrogen, optionally substituted $C_1$-$C_6$ alkyl, optionally substituted $C_2$-$C_6$ alkenyl, and optionally substituted aryl. $R_9$ may be hydrogen. $R_9$ may be an optionally substituted straight chain or branched $C_1$-$C_6$ alkyl, for example a straight chain $C_1$-$C_6$ alkyl, or an optionally substituted straight chain or branched $C_2$-$C_6$ alkenyl, for example allyl, 2-butenyl, etc. In some embodiments $R_9$ may be a straight chain or branched $C_1$-$C_4$ alkyl, for example a straight chain $C_1$-$C_4$ alkyl, or a $C_2$-$C_4$ alkenyl. $R_9$ may be an optionally substituted aryl. An aryl is a 6- to 14-membered aromatic ring, preferably a 6- to 10-membered aromatic ring and includes polycyclic ring systems in which two or more carbon atoms are common to adjoining rings where at least one ring is aromatic. Examples of aryl groups include, but are not limited to phenyl, naphthyl, anthracenyl, and phenantherenyl. An aryl group may be substituted with one or more $C_1$-$C_4$ alkyl or perfluoralkyl groups, $C_1$-$C_4$ hydroxyalkyl groups, hydroxyl groups, nitro groups or halo groups (e.g., F, Cl, I, or Br). An aryl group may be ortho-, meta-, and/or para-substituted, preferably para-substituted.

The pharmaceutically acceptable halide anion, $X^-$, may be chloride ($Cl^-$), bromide ($Br^-$), or iodide ($I^-$).

$R_1$ and X of the secondary alkyl halide are identical to how $R_1$ and X are defined in formula (I). For example, if the secondary alkyl halide is isopropyl iodide, then $R_1$ in formula (I) is isopropyl and X in formula (I) is iodide ($I^-$).

In formula (II), $R_2$, $R_3$, $R_4$, $R_5$, $R_6$, $R_7$, $R_8$, and $R_{10}$ are identical to how $R_2$, $R_3$, $R_4$, $R_5$, $R_6$, $R_7$, $R_8$, and $R_{10}$ are defined in formula (I). For example, if $R_2$ is hydrogen for formula (I), then $R_2$ for formula (II) is hydrogen also.

Exemplary compounds of formula (I) are those wherein $R_1$ is isopropyl.

In one embodiment of the disclosure, a substituted or unsubstituted tryptamine of formula (II) is reacted with an excess of a secondary alkyl halide, $R_1X$, wherein the secondary alkyl of the secondary alkyl halide is the same as $R_1$ of formula (I) and wherein the halide is attached to a secondary carbon of alkyl group. The secondary alkyl halide may be a straight chain or branched secondary $C_3$-$C_{10}$ alkyl halide or a substituted or unsubstituted secondary $C_3$-$C_6$ cycloalkyl halide. The secondary alkyl halide may be a straight chain or branched secondary $C_3$-$C_{10}$ alkyl halide, for example a straight chain secondary $C_3$-$C_{10}$ alkyl halide, or a substituted or unsubstituted secondary $C_3$-$C_6$ cycloalkyl halide, for example cyclopropyl halide, cyclobutyl halide, cyclopentyl halide, etc. In some embodiments, the secondary alkyl halide may be a straight chain or branched secondary $C_3$-$C_6$ alkyl halide, for example a straight chain secondary $C_3$-$C_6$ alkyl halide. The secondary alkyl halide may be selected from an isopropyl halide, a 2-halide-butane, a 2-halide-pentane, a 3-halide-pentane, a 2-halide-hexane, a 3-halide-hexane, a 2-halide-heptane, a 3-halide-heptane, a 4-halide-heptane, a 2-halide-octane, a 3-halide-octane, a 4-halide-octane, a 2-halide-nonane, a 3-halide-nonane, a 4-halide-nonane, a 5-halide-nonane, a 2-halide-decane, a 3-halide-decane, a 4-halide-decane, a 5-halide-decane, a 1-halide-cyclopropane, a 1-halide-cyclobutane, a 2-halide-cyclobutane, a 1-halide-cyclopentane, a 2-halide-cyclopentane, a 3-halide-cyclopentane, a 1-halide-cyclohexane, a 2-halide-cyclohexane, or a 3-halide-cyclohexane. Exemplary halides include chloride ($Cl^-$), bromide ($Br^-$), and iodide ($I^-$). In some embodiments of the disclosure, the secondary alkyl halide is an isopropyl iodide, 2-iodo-butane, 2-iodo-pentane, 3-iodo-pentane, 2-iodo-hexane, 3-iodo-hexane, 2-iodo-heptane, 3-iodo-heptane, 4-iodo-heptane, 2-iodo-octane, 3-iodo-octane, 4-iodo-octane, 2-iodo-nonane, 3-iodo-nonane, 4-iodo-nonane, 5-iodo-nonane, 2-iodo-decane, 3-iodo-decane, 4-iodo-decane, 5-iodo-decane, 1-iodo-cyclopropane, 1-iodo-cyclobutane, 2-iodo-cyclobutane, 1-iodo-cyclopentane, 2-iodo-cyclopentane, 3-iodo-cyclopentane, 1-iodo-cyclohexane, 2-iodo-cyclohexane, or 3-iodo-cyclohexane. In other embodiments of the disclosure, the secondary alkyl halide is isopropyl iodide.

In one embodiment of the disclosure, to make a mono alkyl tryptamine of formula (I), a substituted or unsubstituted tryptamine of formula (II) is treated with an excess of a secondary alkyl halide and the solution is refluxed for about 12-24 hours. In one embodiment of the disclosure, the substituted or unsubstituted tryptamine of formula (II) is treated with an excess of a secondary alkyl halide at a temperature sufficient to affect one alkylation, which can be monitored spectroscopically, e.g., by NMR. In some embodiments, excess is 5 equivalents, 6 equivalents, 7 equivalents, 8 equivalents, 9 equivalents, 10 equivalents, 11 equivalents, 12 equivalents, 13 equivalents, 14 equivalents, 15 equivalents, 16 equivalents, 17 equivalents, 18 equivalents, 19 equivalents, 20 equivalents, 21 equivalents, 22 equivalents, 23 equivalents, 24 equivalents, or 25 equivalents. In some embodiments of the disclosure, the substituted or unsubstituted tryptamine of formula (II) is treated with an alkylating agent and the solution is refluxed for about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours. In one embodiment of the disclosure, the solution is refluxed in isopropanol.

Compounds of formula (I) may be prepared by the following reaction mechanism.

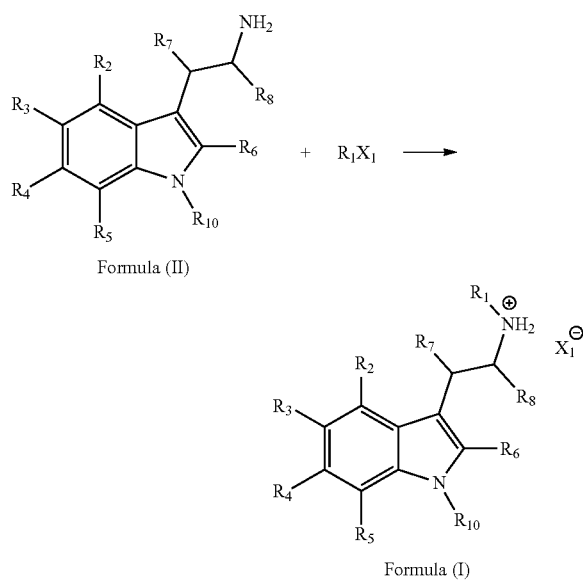

Formula (II)

Formula (I)

wherein:
$R_1$ is a secondary alkyl;
$X_1$ is a halide,
wherein $R_1X_1$ is a secondary alkyl halide;
$R_2$, $R_3$, $R_4$, $R_5$, $R_6$, $R_7$, $R_8$, and $R_{10}$ are independently selected from hydrogen, optionally substituted $C_1$-$C_6$ alkyl, optionally substituted $C_1$-$C_6$ alkenyl, optionally substituted $C_1$-$C_6$ heteroalkyl, optionally substituted heteroaryl, optionally substituted aryl, halogen, hydroxy, —$OR_9$, —$OC(O)R_9$, —$OC(O)OR_9$, and —$OSO_2R_9$; and
$R_9$ is independently selected from hydrogen, optionally substituted $C_1$-$C_6$ alkyl, optionally substituted $C_1$-$C_6$ alkenyl, and optionally substituted aryl.

In formula (I), $R_1$ is a secondary alkyl, wherein a secondary carbon of alkyl group is attached to the amine nitrogen of the mono alkyl tryptamine. $R_1$ may be a straight chain or branched secondary $C_3$-$C_{10}$ alkyl or a substituted or unsubstituted secondary $C_3$-$C_6$ cycloalkyl. $R_1$ may be a straight chain or branched secondary $C_3$-$C_{10}$ alkyl, for example a straight chain secondary $C_3$-$C_{10}$ alkyl, or a substituted or unsubstituted secondary $C_3$-$C_6$ cycloalkyl, for example cyclopropyl, cyclobutyl, cyclopentyl, etc. In some embodiments, $R_1$ may be a straight chain or branched secondary $C_3$-$C_6$ alkyl, for example a straight chain secondary $C_3$-$C_6$ alkyl. $R_1$ may be selected from isopropyl, 2-butyl, 2-pentyl, 3-pentyl, 2-hexyl, 3-hexyl, 2-heptyl, 3-heptyl, 4-heptyl, 2-octyl, 3-octyl, 4-octyl, 2-nonanyl, 3-nonanyl, 4-nonanyl, 5-nonanyl, 2-decanyl, 3-decanyl, 4-decanyl, 5-decanyl, 1-cyclopropyl, 1-cyclobutyl, 2-cyclobutyl, 1-cyclopentyl, 2-cyclopentyl, 3-cyclopentyl, 1-cyclohexyl, 2-cyclohexyl, or 3-cyclohexyl. In other embodiments of the disclosure, $R_1$ is isopropyl.

$X_1$ is a halide selected from the group consisting of chloride (Cl⁻), bromide (Br⁻), and iodide (I⁻). In some embodiments, $X_1$ is iodide.

In formulas (I) and (II), $R_2$, $R_3$, $R_4$, $R_5$, $R_6$, $R_7$, $R_8$, and $R_{10}$ are independently selected from hydrogen, optionally substituted $C_1$-$C_6$ alkyl, optionally substituted $C_2$-$C_6$ alkenyl, optionally substituted $C_1$-$C_6$ heteroalkyl, optionally substituted heteroaryl, optionally substituted aryl, halogen, hydroxy, —$OR_9$, —$OC(O)R_9$, —$OC(O)OR_9$, and —$OSO_2R_9$. $R_2$, $R_3$, $R_4$, $R_5$, $R_6$, $R_7$, $R_8$, and $R_{10}$ may each independently be hydrogen. $R_2$, $R_3$, $R_4$, $R_5$, $R_6$, $R_7$, $R_8$, and $R_{10}$ may each independently be an optionally substituted straight chain or branched $C_1$-$C_6$ alkyl, for example a straight chain $C_1$-$C_6$ alkyl, or an optionally substituted straight chain or branched $C_2$-$C_6$ alkenyl, for example allyl, 2-butenyl, etc. In some embodiments $R_2$, $R_3$, $R_4$, $R_5$, $R_6$, $R_7$, $R_8$, and $R_{10}$ may each independently be a straight chain or branched $C_1$-$C_4$ alkyl, for example a straight chain $C_1$-$C_4$ alkyl, or a $C_2$-$C_4$ alkenyl. $R_2$, $R_3$, $R_4$, $R_5$, $R_6$, $R_7$, $R_8$, and $R_{10}$ may each independently be an optionally substituted $C_1$-$C_6$-heteroalkyl, including but not limited to alkoxy, alkylthio, and alkylamino. $R_2$, $R_3$, $R_4$, $R_5$, $R_6$, $R_7$, $R_8$, and $R_{10}$ may each independently be an optionally substituted heteroaryl, including, but not limited to, furano, pyridinyl, pyrimidinyl, etc. $R_2$, $R_3$, $R_4$, $R_5$, $R_6$, $R_7$, $R_8$, and $R_{10}$ may each independently be an optionally substituted aryl. An aryl is a 6- to 14-membered aromatic ring, preferably a 6- to 10-membered aromatic ring and includes polycyclic ring systems in which two or more carbon atoms are common to adjoining rings where at least one ring is aromatic. Examples of aryl groups include, but are not limited to phenyl, naphthyl, anthracenyl, and phenantherenyl. An aryl group may be substituted with one or more $C_1$-$C_4$ alkyl or perfluoralkyl groups, $C_1$-$C_4$ hydroxyalkyl groups, hydroxyl groups, nitro groups or halo groups (e.g., F, Cl, I, or Br). An aryl group may be ortho-, meta-, and/or para-substituted, preferably para-substituted. $R_2$, $R_3$, $R_4$, $R_5$, $R_6$, $R_7$, $R_8$, and $R_{10}$ may each independently be a halogen. Exemplary halogens include fluorine (F), chlorine (Cl), bromine (Br), and iodine (I). $R_2$, $R_3$, $R_4$, $R_5$, $R_6$, $R_7$, $R_8$, and $R_{10}$ may each independently be hydroxy. $R_2$, $R_3$, $R_4$, $R_5$, $R_6$, $R_7$, $R_8$, and $R_{10}$ may each independently be —$OR_9$, —$OC(O)R_9$, —$OC(O)OR_9$, or —$OSO_2R_9$, wherein $R_9$ is independently selected from hydrogen, optionally substituted $C_1$-$C_6$ alkyl, optionally substituted $C_2$-$C_6$ alkenyl, and optionally substituted aryl. $R_2$, $R_3$, $R_4$, $R_5$, $R_6$, $R_7$, $R_8$, and $R_{10}$ in formula (II) are identical to how $R_2$, $R_3$, $R_4$, $R_5$, $R_6$, $R_7$, $R_8$, and $R_{10}$ are defined in formula (I). For example, if $R_2$ is hydrogen for formula (I), then $R_2$ for formula (II) is hydrogen also.

In formulas (I) and (II), $R_9$ is independently selected from hydrogen, optionally substituted $C_1$-$C_6$ alkyl, optionally substituted $C_2$-$C_6$ alkenyl, and optionally substituted aryl. $R_9$ may be hydrogen. $R_9$ may be an optionally substituted straight chain or branched $C_1$-$C_6$ alkyl, for example a straight chain $C_1$-$C_6$ alkyl, or an optionally substituted straight chain or branched $C_2$-$C_6$ alkenyl, for example allyl, 2-butenyl, etc. In some embodiments $R_9$ may be a straight chain or branched $C_1$-$C_4$ alkyl, for example a straight chain $C_1$-$C_4$ alkyl, or a $C_2$-$C_4$ alkenyl. $R_9$ may be an optionally substituted aryl. An aryl is a 6- to 14-membered aromatic ring, preferably a 6- to 10-membered aromatic ring and includes polycyclic ring systems in which two or more carbon atoms are common to adjoining rings where at least one ring is aromatic. Examples of aryl groups include, but are not limited to phenyl, naphthyl, anthracenyl, and phenantherenyl. An aryl group may be substituted with one or more $C_1$-$C_4$ alkyl or perfluoralkyl groups, $C_1$-$C_4$ hydroxyalkyl groups, hydroxyl groups, nitro groups or halo groups (e.g., F, Cl, I, or Br). An aryl group may be ortho-, meta-, and/or para-substituted, preferably para-substituted.

The disclosure further relates to a method of making a dialkyl tryptamine compound of formula (III),

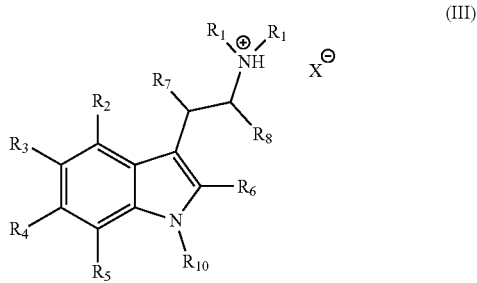

wherein:
$R_1$ is for each occurrence a secondary alkyl;
$R_2$, $R_3$, $R_4$, $R_5$, $R_6$, $R_7$, $R_8$, and $R_{10}$ are independently selected from hydrogen, optionally substituted $C_1$-$C_6$ alkyl, optionally substituted $C_1$-$C_6$ alkenyl, optionally substituted $C_1$-$C_6$ heteroalkyl, optionally substituted heteroaryl, optionally substituted aryl, halogen, hydroxy, —$OR_9$, —$OC(O)R_9$, —$OC(O)OR_9$, and —$OSO_2R_9$;
$R_9$ is independently selected from hydrogen, optionally substituted $C_1$-$C_6$ alkyl, optionally substituted $C_2$-$C_6$ alkenyl, and optionally substituted aryl; and
$X^-$ is a pharmaceutically acceptable halide anion;
comprising the step of:
reacting a substituted or unsubstituted tryptamine of formula (IV)

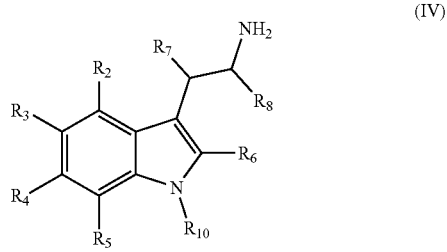

with an excess of a secondary alkyl halide, $R_1X$;
wherein:
$R_1$ and X of the secondary alkyl halide are identical to how $R_1$ and X are defined in formula (III); and
$R_2$, $R_3$, $R_4$, $R_5$, $R_6$, $R_7$, $R_8$, and $R_{10}$ in formula (IV) are identical to how $R_2$, $R_3$, $R_4$, $R_5$, $R_6$, $R_7$, $R_8$, and $R_{10}$ are defined in formula (III). For example, if $R_2$ is hydrogen for formula (III), then $R_2$ for formula (IV) is hydrogen also.

In formula (III), $R_1$ is for each occurrence a secondary alkyl, wherein a secondary carbon of each of the alkyl groups is attached to the amine nitrogen of the dialkyl tryptamine. $R_1$ may be a straight chain or branched secondary $C_3$-$C_{10}$ alkyl or a substituted or unsubstituted secondary $C_3$-$C_6$ cycloalkyl. $R_1$ may be a straight chain or branched secondary $C_3$-$C_{10}$ alkyl, for example a straight chain secondary $C_3$-$C_{10}$ alkyl, or a substituted or unsubstituted secondary $C_3$-$C_6$ cycloalkyl, for example cyclopropyl, cyclobutyl, cyclopentyl, etc. In some embodiments, $R_1$ may be a straight chain or branched secondary $C_3$-$C_6$ alkyl, for example a straight chain secondary $C_3$-$C_6$ alkyl. $R_1$ may be selected from isopropyl, 2-butyl, 2-pentyl, 3-pentyl, 2-hexyl, 3-hexyl, 2-heptyl, 3-heptyl, 4-heptyl, 2-octyl, 3-octyl, 4-octyl, 2-nonanyl, 3-nonanyl, 4-nonanyl, 5-nonanyl, 2-decanyl, 3-decanyl, 4-decanyl, 5-decanyl, 1-cyclopropyl, 1-cyclobutyl, 2-cyclobutyl, 1-cyclopentyl, 2-cyclopentyl, 3-cyclopentyl, 1-cyclohexyl, 2-cyclohexyl, or 3-cyclohexyl. In other embodiments of the disclosure, $R_1$ is isopropyl.

In formula (III), $R_2$, $R_3$, $R_4$, $R_5$, $R_6$, $R_7$, $R_8$, and $R_{10}$ are independently selected from hydrogen, optionally substituted $C_1$-$C_6$ alkyl, optionally substituted $C_2$-$C_6$ alkenyl, optionally substituted $C_1$-$C_6$ heteroalkyl, optionally substituted heteroaryl, optionally substituted aryl, halogen, hydroxy, —$OR_9$, —$OC(O)R_9$, —$OC(O)OR_9$, and —$OSO_2R_9$. $R_2$, $R_3$, $R_4$, $R_5$, $R_6$, $R_7$, $R_8$, and $R_{10}$ may each independently be hydrogen. $R_2$, $R_3$, $R_4$, $R_5$, $R_6$, $R_7$, $R_8$, and $R_{10}$ may each independently be an optionally substituted straight chain or branched $C_1$-$C_6$ alkyl, for example a straight chain $C_1$-$C_6$ alkyl, or an optionally substituted straight chain or branched $C_2$-$C_6$ alkenyl, for example allyl, 2-butenyl, etc. In some embodiments $R_2$, $R_3$, $R_4$, $R_5$, $R_6$, $R_7$, $R_8$, and $R_{10}$ may each independently be a straight chain or branched $C_1$-$C_4$ alkyl, for example a straight chain $C_1$-$C_4$ alkyl, or a $C_2$-$C_4$ alkenyl. $R_2$, $R_3$, $R_4$, $R_5$, $R_6$, $R_7$, $R_8$, and $R_{10}$ may each independently be an optionally substituted $C_1$-$C_6$-heteroalkyl, including but not limited to alkoxy, alkylthio, and alkylamino. $R_2$, $R_3$, $R_4$, $R_5$, $R_6$, $R_7$, $R_8$, and $R_{10}$ may each independently be an optionally substituted heteroaryl, including, but not limited to, furano, pyridinyl, pyrimidinyl, etc. $R_2$, $R_3$, $R_4$, $R_5$, $R_6$, $R_7$, $R_8$, and $R_{10}$ may each independently be an optionally substituted aryl. An aryl is a 6- to 14-membered aromatic ring, preferably a 6- to 10-membered aromatic ring and includes polycyclic ring systems in which two or more carbon atoms are common to adjoining rings where at least one ring is aromatic. Examples of aryl groups include, but are not limited to phenyl, naphthyl, anthracenyl, and phenantherenyl. An aryl group may be substituted with one or more $C_1$-$C_4$ alkyl or perfluoralkyl groups, $C_1$-$C_4$ hydroxyalkyl groups, hydroxyl groups, nitro groups or halo groups (e.g., F, Cl, I, or Br). An aryl group may be ortho-, meta-, and/or para-substituted, preferably para-substituted. $R_2$, $R_3$, $R_4$, $R_5$, $R_6$, $R_7$, $R_8$, and $R_{10}$ may each independently be a halogen. Exemplary halogens include fluorine (F), chlorine (Cl), bromine (Br), and iodine (I). $R_2$, $R_3$, $R_4$, $R_5$, $R_6$, $R_7$, $R_8$, and $R_{10}$ may each independently be hydroxy. $R_2$, $R_3$, $R_4$, $R_5$, $R_6$, $R_7$, $R_8$, and $R_{10}$ may each independently be —$OR_9$, —$OC(O)R_9$, —$OC(O)OR_9$, or —$OSO_2R_9$, wherein $R_9$ is independently selected from hydrogen, optionally substituted $C_1$-$C_6$ alkyl, optionally substituted $C_2$-$C_6$ alkenyl, and optionally substituted aryl.

In formula (III), $R_9$ is independently selected from hydrogen, optionally substituted $C_1$-$C_6$ alkyl, optionally substituted $C_2$-$C_6$ alkenyl, and optionally substituted aryl. $R_9$ may be hydrogen. $R_9$ may be an optionally substituted straight chain or branched $C_1$-$C_6$ alkyl, for example a straight chain $C_1$-$C_6$ alkyl, or an optionally substituted straight chain or branched $C_2$-$C_6$ alkenyl, for example allyl, 2-butenyl, etc. In some embodiments $R_9$ may be a straight chain or branched $C_1$-$C_4$ alkyl, for example a straight chain $C_1$-$C_4$ alkyl, or a $C_2$-$C_4$ alkenyl. $R_9$ may be an optionally substituted aryl. An aryl is a 6- to 14-membered aromatic ring, preferably a 6- to 10-membered aromatic ring and includes polycyclic ring systems in which two or more carbon atoms are common to adjoining rings where at least one ring is aromatic. Examples of aryl groups include, but are not limited to phenyl, naphthyl, anthracenyl, and phenantherenyl. An aryl group may be substituted with one or more $C_1$-$C_4$ alkyl or perfluoroalkyl groups, $C_1$-$C_4$ hydroxyalkyl groups, hydroxyl groups, nitro groups or halo groups (e.g., F, Cl, I, or Br). An aryl group may be ortho-, meta-, and/or para-substituted, preferably para-substituted.

The pharmaceutically acceptable halide anion, $X^-$, may be chloride ($Cl^-$), bromide ($Br^-$), or iodide ($I^-$).

$R_1$ and X of the secondary alkyl halide are identical to how $R_1$ and X are defined in formula (III). For example, if the secondary alkyl halide is isopropyl iodide, then $R_1$ in formula (III) is isopropyl and X in formula (I) is iodide ($I^-$).

In formula (IV), $R_2$, $R_3$, $R_4$, $R_5$, $R_6$, $R_7$, $R_8$, and $R_{10}$ are identical to how $R_2$, $R_3$, $R_4$, $R_5$, $R_6$, $R_7$, $R_8$, and $R_{10}$ are defined in formula (III). For example, if $R_2$ is hydrogen for formula (III), then $R_2$ for formula (IV) is hydrogen also.

Exemplary compounds of formula (III) are those wherein $R_1$ is isopropyl.

In one embodiment of the disclosure, a substituted or unsubstituted tryptamine of formula (IV) is reacted with an excess of a secondary alkyl halide, $R_1X$, wherein the secondary alkyl of the secondary alkyl halide is the same as the $R_1$ groups of formula (III) and wherein the halide is attached to a secondary carbon of alkyl group. The secondary alkyl halide may be a straight chain or branched secondary $C_3$-$C_{10}$ alkyl halide or a substituted or unsubstituted secondary $C_3$-$C_6$ cycloalkyl halide. The secondary alkyl halide may be a straight chain or branched secondary $C_3$-$C_{10}$ alkyl halide, for example a straight chain secondary $C_3$-$C_{10}$ alkyl halide, or a substituted or unsubstituted secondary $C_3$-$C_6$ cycloalkyl halide, for example cyclopropyl halide, cyclobutyl halide, cyclopentyl halide, etc. In some embodiments, the secondary alkyl halide may be a straight chain or branched secondary $C_3$-$C_6$ alkyl halide, for example a straight chain secondary $C_3$-$C_6$ alkyl halide. The secondary alkyl halide may be selected from an isopropyl halide, a 2-halide-butane, a 2-halide-pentane, a 3-halide-pentane, a 2-halide-hexane, a 3-halide-hexane, a 2-halide-heptane, a 3-halide-heptane, a 4-halide-heptane, a 2-halide-octane, a 3-halide-octane, a 4-halide-octane, a 2-halide-nonane, a 3-halide-nonane, a 4-halide-nonane, a 5-halide-nonane, a 2-halide-decane, a 3-halide-decane, a 4-halide-decane, a 5-halide-decane, a 1-halide-cyclopropane, a 1-halide-cyclobutane, a 2-halide-cyclobutane, a 1-halide-cyclopentane, a 2-halide-cyclopentane, a 3-halide-cyclopentane, a 1-halide-cyclohexane, a 2-halide-cyclohexane, or a 3-halide-cyclohexane. Exemplary halides include chloride ($Cl^-$), bromide ($Br^-$), and iodide ($I^-$). In some embodiments of the disclosure, the secondary alkyl halide is an isopropyl iodide, 2-iodo-butane, 2-iodo-pentane, 3-iodo-pentane, 2-iodo-hexane, 3-iodo-hexane, 2-iodo-heptane, 3-iodo-heptane, 4-iodo-heptane, 2-iodo-octane, 3-iodo-octane, 4-iodo-octane, 2-iodo-nonane, 3-iodo-nonane, 4-iodo-nonane, 5-iodo-nonane, 2-iodo-decane, 3-iodo-decane, 4-iodo-decane, 5-iodo-decane, 1-iodo-cyclopropane, 1-iodo-cyclobutane, 2-iodo-cyclobutane, 1-iodo-cyclopentane, 2-iodo-cyclopentane, 3-iodo-cyclopentane, 1-iodo-cyclohexane, 2-iodo-cyclohexane, or 3-iodo-cyclohexane. In other embodiments of the disclosure, the secondary alkyl halide is isopropyl iodide.

In other embodiments of the disclosure, to make the dialkyl tryptamine of formula (III), the substituted or unsubstituted tryptamine of formula (IV) is treated with an excess of a secondary alkyl halide and the solution is refluxed for about 36-72 hours. In one embodiment of the disclosure, the substituted or unsubstituted tryptamine of formula (IV) is treated with an excess of a secondary alkyl halide at a temperature sufficient to affect two alkylations, which can be monitored spectroscopically, e.g., by NMR. In some embodiments, excess is 5 equivalents, 6 equivalents, 7 equivalents, 8 equivalents, 9 equivalents, 10 equivalents, 11 equivalents, 12 equivalents, 13 equivalents, 14 equivalents, 15 equivalents, 16 equivalents, 17 equivalents, 18 equivalents, 19 equivalents, 20 equivalents, 21 equivalents, 22 equivalents, 23 equivalents, 24 equivalents, or 25 equivalents. In some embodiments of the disclosure, the primary amine is treated with an alkylating agent and the solution is refluxed for about 36 hours, about 37 hours, about 38 hours, about 39 hours, about 40 hours, about 41 hours, about 42 hours, about 43 hours, about 44 hours, about 45 hours, about 46 hours, about 47 hours, about 48 hours, about 49 hours, about 50 hours, about 51 hours, about 52 hours, about 53 hours, about 54 hours, about 55 hours, about 56 hours, about 57 hours, about 58 hours, about 59 hours, about 60 hours, about 61 hours, about 62 hours, about 63 hours, about 64 hours, about 65 hours, about 66 hours, about 67 hours, about 68 hours, about 69 hours, about 70 hours, about 71 hours, or about 72 hours. In one embodiment of the disclosure, the solution is refluxed in isopropanol.

Compounds of formula (II) may be prepared by the following reaction mechanism.

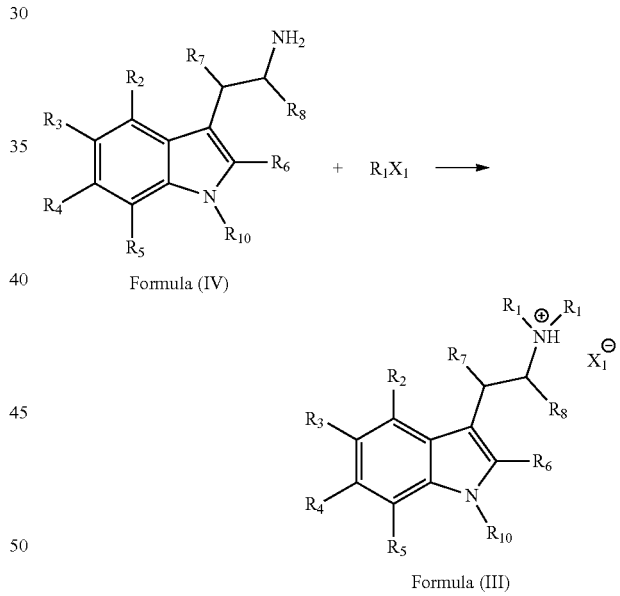

wherein:
$R_1$ is for each occurrence a secondary alkyl;
$X_2$ is a halide,
wherein $R_1X_1$ is a secondary alkyl halide
$R_2$, $R_3$, $R_4$, $R_5$, $R_6$, $R_7$, $R_8$, and $R_{10}$ are independently selected from hydrogen, optionally substituted $C_1$-$C_6$ alkyl, optionally substituted $C_2$-$C_6$ alkenyl, optionally substituted $C_1$-$C_6$ heteroalkyl, optionally substituted heteroaryl, optionally substituted aryl, halogen, hydroxy, —$OR_9$, —$OC(O)R_9$, —$OC(O)OR_9$, and —$OSO_2R_9$; and
$R_9$ is independently selected from hydrogen, optionally substituted $C_1$-$C_6$ alkyl, optionally substituted $C_2$-$C_6$ alkenyl, and optionally substituted aryl.

In formula (III), $R_1$ is for each occurrence a secondary alkyl, wherein a secondary carbon of each of the alkyl groups is attached to the amine nitrogen of the dialkyl tryptamine. $R_1$ may be a straight chain or branched secondary $C_3$-$C_{10}$ alkyl or a substituted or unsubstituted secondary $C_3$-$C_6$ cycloalkyl. $R_1$ may be a straight chain or branched secondary $C_3$-$C_{10}$ alkyl, for example a straight chain secondary $C_3$-$C_{10}$ alkyl, or a substituted or unsubstituted secondary $C_3$-$C_6$ cycloalkyl, for example cyclopropyl, cyclobutyl, cyclopentyl, etc. In some embodiments, $R_1$ may be a straight chain or branched secondary $C_3$-$C_6$ alkyl, for example a straight chain secondary $C_3$-$C_6$ alkyl. $R_1$ may be selected from isopropyl, 2-butyl, 2-pentyl, 3-pentyl, 2-hexyl, 3-hexyl, 2-heptyl, 3-heptyl, 4-heptyl, 2-octyl, 3-octyl, 4-octyl, 2-nonanyl, 3-nonanyl, 4-nonanyl, 5-nonanyl, 2-decanyl, 3-decanyl, 4-decanyl, 5-decanyl, 1-cyclopropyl, 1-cyclobutyl, 2-cyclobutyl, 1-cyclopentyl, 2-cyclopentyl, 3-cyclopentyl, 1-cyclohexyl, 2-cyclohexyl, or 3-cyclohexyl. In other embodiments of the disclosure, $R_1$ is isopropyl.

$X_1$ is a halide selected from the group consisting of chloride (Cl⁻), bromide (Br⁻), and iodide (I⁻). In some embodiments, $X_1$ is iodide.

In formulas (III) and (IV), $R_2$, $R_3$, $R_4$, $R_5$, $R_6$, $R_7$, $R_8$, and $R_{10}$ are independently selected from hydrogen, optionally substituted $C_1$-$C_6$ alkyl, optionally substituted $C_2$-$C_6$ alkenyl, optionally substituted $C_1$-$C_6$ heteroalkyl, optionally substituted heteroaryl, optionally substituted aryl, halogen, hydroxy, —$OR_9$, —$OC(O)R_9$, —$OC(O)OR_9$, and —$OSO_2R_9$. $R_2$, $R_3$, $R_4$, $R_5$, $R_6$, $R_7$, $R_8$, and $R_{10}$ may each independently be hydrogen. $R_2$, $R_3$, $R_4$, $R_5$, $R_6$, $R_7$, $R_8$, and $R_{10}$ may each independently be an optionally substituted straight chain or branched $C_1$-$C_6$ alkyl, for example a straight chain $C_1$-$C_6$ alkyl, or an optionally substituted straight chain or branched $C_2$-$C_6$ alkenyl, for example allyl, 2-butenyl, etc. In some embodiments $R_2$, $R_3$, $R_4$, $R_5$, $R_6$, $R_7$, $R_8$, and $R_{10}$ may each independently be a straight chain or branched $C_1$-$C_4$ alkyl, for example a straight chain $C_1$-$C_4$ alkyl, or a $C_2$-$C_4$ alkenyl. $R_2$, $R_3$, $R_4$, $R_5$, $R_6$, $R_7$, $R_8$, and $R_{10}$ may each independently be an optionally substituted $C_1$-$C_6$- heteroalkyl, including but not limited to alkoxy, alkylthio, and alkylamino. $R_2$, $R_3$, $R_4$, $R_5$, $R_6$, $R_7$, $R_8$, and $R_{10}$ may each independently be an optionally substituted heteroaryl, including, but not limited to, furano, pyridinyl, pyrimidinyl, etc. $R_2$, $R_3$, $R_4$, $R_5$, $R_6$, $R_7$, $R_8$, and $R_{10}$ may each independently be an optionally substituted aryl. An aryl is a 6- to 14-membered aromatic ring, preferably a 6- to 10-membered aromatic ring and includes polycyclic ring systems in which two or more carbon atoms are common to adjoining rings where at least one ring is aromatic. Examples of aryl groups include, but are not limited to phenyl, naphthyl, anthracenyl, and phenantherenyl. An aryl group may be substituted with one or more $C_1$-$C_4$ alkyl or perfluoroalkyl groups, $C_1$-$C_4$ hydroxyalkyl groups, hydroxyl groups, nitro groups or halo groups (e.g., F, Cl, I, or Br). An aryl group may be ortho-, meta-, and/or para-substituted, preferably para-substituted. $R_2$, $R_3$, $R_4$, $R_5$, $R_6$, $R_7$, $R_8$, and $R_{10}$ may each independently be a halogen. Exemplary halogens include fluorine (F), chlorine (Cl), bromine (Br), and iodine (I). $R_2$, $R_3$, $R_4$, $R_5$, $R_6$, $R_7$, $R_8$, and $R_{10}$ may each independently be hydroxy. $R_2$, $R_3$, $R_4$, $R_5$, $R_6$, $R_7$, $R_8$, and $R_{10}$ may each independently be —$OR_9$, —$OC(O)R_9$, —$OC(O)OR_9$, or —$OSO_2R_9$, wherein $R_9$ is independently selected from hydrogen, optionally substituted $C_1$-$C_6$ alkyl, optionally substituted $C_2$-$C_6$ alkenyl, and optionally substituted aryl. $R_2$, $R_3$, $R_4$, $R_5$, $R_6$, $R_7$, $R_8$, and $R_{10}$ in formula (IV) are identical to how $R_2$, $R_3$, $R_4$, $R_5$, $R_6$, $R_7$, $R_8$, and $R_{10}$ are defined in formula (III). For example, if $R_2$ is hydrogen for formula (III), then $R_2$ for formula (IV) is hydrogen also.

In formulas (III) and (IV), $R_9$ is independently selected from hydrogen, optionally substituted $C_1$-$C_6$ alkyl, optionally substituted $C_2$-$C_6$ alkenyl, and optionally substituted aryl. $R_9$ may be hydrogen. $R_9$ may be an optionally substituted straight chain or branched $C_1$-$C_6$ alkyl, for example a straight chain $C_1$-$C_6$ alkyl, or an optionally substituted straight chain or branched $C_2$-$C_6$ alkenyl, for example allyl, 2-butenyl, etc. In some embodiments $R_9$ may be a straight chain or branched $C_1$-$C_4$ alkyl, for example a straight chain $C_1$-$C_4$ alkyl, or a $C_2$-$C_4$ alkenyl. $R_9$ may be an optionally substituted aryl. An aryl is a 6- to 14-membered aromatic ring, preferably a 6- to 10-membered aromatic ring and includes polycyclic ring systems in which two or more carbon atoms are common to adjoining rings where at least one ring is aromatic. Examples of aryl groups include, but are not limited to phenyl, naphthyl, anthracenyl, and phenantherenyl. An aryl group may be substituted with one or more $C_1$-$C_4$ alkyl or perfluoralkyl groups, $C_1$-$C_4$ hydroxyalkyl groups, hydroxyl groups, nitro groups or halo groups (e.g., F, Cl, I, or Br). An aryl group may be ortho-, meta-, and/or para-substituted, preferably para-substituted.

Methods of Treatment and Therapeutic Uses

5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, or crystalline form 1 of 5-F-NiPT iodide, or a compound of formula (I) or formula (III) according to the disclosure, and the methods and the compositions (e.g., pharmaceutical compositions) are used to regulate the activity of a neurotransmitter receptor by administering a therapeutically effective dose of 5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, or crystalline form 1 of 5-F-NiPT iodide, or a compound of formula (I) or formula (III) of the disclosure. In one embodiment, 5-Cl-NiPT iodide, crystalline 5-Cl-NiPT iodide, [5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, or crystalline form 1 of 5-F-NiPT iodide, or a compound of formula (I) or formula (III) according to the disclosure, and the methods and the compositions (e.g., pharmaceutical compositions) are used to treat inflammation and/or pain by administering a therapeutically effective dose of 5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, or crystalline form 1 of 5-F-NiPT iodide, or a compound of formula (I) or formula (III) of the disclosure.

Methods of the disclosure also relate to the administration of a therapeutically effective amount of 5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, or crystalline form 1 of 5-F-NiPT iodide, or a compound of formula (I) or formula (III) of this disclosure to prevent or treat a disease or condition, such as those discussed below for a subject in need of treatment. 5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, or crystalline form 1 of 5-F-NiPT iodide, or a compound of formula (I) or formula (III) of this disclosure may be administered neat or as a composition comprising 5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, or crystalline form 1 of 5-F-NiPT iodide, or a compound of formula (I) or formula (III) of this disclosure as discussed below.

5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, or crystalline form 1 of 5-F-NiPT iodide, or a compound of formula (I) or formula (III) of this disclosure may be used to prevent and/or treat a psychological disorder. The disclosure provides a method for preventing and/or treating a psychological disorder by administering to a subject in need thereof a therapeutically effective amount of 5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, or crystalline form 1 of 5-F-NiPT iodide, or a compound of formula (I) or formula (III) of this disclosure, including the exemplary embodiments discussed herein. The psychological disorder may be chosen from: depression; psychotic disorder; schizophrenia; schizophreniform disorder (acute schizophrenic episode); schizoaffective disorder; bipolar I disorder (mania, manic disorder, manic-depressive psychosis); bipolar II disorder; major depressive disorder; major depressive disorder with psychotic feature (psychotic depression); delusional disorders (paranoia); shared psychotic disorder (shared paranoia disorder); brief psychotic disorder (other and unspecified reactive psychosis); psychotic disorder not otherwise specified (unspecified psychosis); paranoid personality disorder; schizoid personality disorder; schizotypal personality disorder; anxiety disorder; social anxiety disorder; substance-induced anxiety disorder; selective mutism; panic disorder; panic attacks; agoraphobia; attention deficit syndrome; post-traumatic stress disorder (PTSD); premenstrual dysphoric disorder (PMDD); and premenstrual syndrome (PMS).

5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, or crystalline form 1 of 5-F-NiPT iodide, or a compound of formula (I) or formula (III) of this disclosure may be used to prevent and/or treat a brain disorder. The disclosure provides a method for preventing and/or treating a brain disorder (e.g., Huntington's disease, Alzheimer's disease, dementia, and Parkinson's disease) by administering to a subject in need thereof a therapeutically effective amount of 5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, or crystalline form 1 of 5-F-NiPT iodide, or a compound of formula (I) or formula (III) of this disclosure.

5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, or crystalline form 1 of 5-F-NiPT iodide, or a compound of formula (I) or formula (III) of this disclosure may be used to prevent and/or treat developmental disorders, delirium, dementia, amnestic disorders and other cognitive disorders, psychiatric disorders due to a somatic condition, drug-related disorders, schizophrenia and other psychotic disorders, mood disorders, anxiety disorders, somatoform disorders, factitious disorders, dissociative disorders, eating disorders, sleep disorders, impulse control disorders, adjustment disorders, or personality disorders. The disclosure provides a method for preventing and/or treating these disorders by administering to a subject in need thereof a therapeutically effective amount of 5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, or crystalline form 1 of 5-F-NiPT iodide, or a compound of formula (I) or formula (III) of this disclosure including the exemplary embodiments discussed above.

5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, or crystalline form 1 of 5-F-NiPT iodide, or a compound of formula (I) or formula (III) of this disclosure may be used to prevent and/or treat inflammation and/or pain, such as for example inflammation and/or pain associated with inflammatory skeletal or muscular diseases or conditions. The disclosure provides a method for preventing and/or treating an inflammation and/or pain by administering to a subject in need thereof a therapeutically effective amount of 5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, or crystalline form 1 of 5-F-NiPT iodide, or a compound of formula (I) or formula (III) of this disclosure, including the exemplary embodiments discussed herein. Generally speaking, treatable "pain" includes nociceptive, neuropathic, and mix-type. A method of the disclosure may reduce or alleviate the symptoms associated with inflammation, including but not limited to treating localized manifestation of inflammation characterized by acute or chronic swelling, pain, redness, increased temperature, or loss of function in some cases. A method of the disclosure may reduce or alleviate the symptoms of pain regardless of the cause of the pain, including but not limited to reducing pain of varying severity, i.e., mild, moderate and severe pain, acute pain and chronic pain. A method of the disclosure is effective in treating joint pain, muscle pain, tendon pain, burn pain, and pain caused by inflammation such as rheumatoid arthritis. Skeletal or muscular diseases or conditions which may be treated include but are not limited to musculoskeletal sprains, musculoskeletal strains, tendinopathy, peripheral radiculopathy, osteoarthritis, joint degenerative disease, polymyalgia rheumatica, juvenile arthritis, gout, ankylosing spondylitis, psoriatic arthritis, systemic lupus erythematosus, costochondritis, tendonitis, bursitis, such as the common lateral epicondylitis (tennis elbow), medial epicondylitis (pitchers elbow) and trochanteric bursitis, temporomandibular joint syndrome, and fibromyalgia.

5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, or crystalline form 1 of 5-F-NiPT iodide, or a compound of formula (I) or formula (III) of this disclosure may be used to modulate activity of a mitogen-activated protein kinase (MAPK), comprising administering a composition of the invention. MAPKs provide a wide-ranging signaling cascade that allow cells to quickly respond to biotic and abiotic stimuli. Exemplary MAPKs include, but are not limited to, Tropomyosin Receptor Kinase A (TrkA), P38-alpha, and c-Jun N-Terminal Kinase 3 (JNK3). TrkA is a high affinity catalytic receptor of nerve growth factor (NGF) protein. TrkA regulates NGF response, influencing neuronal differentiation and outgrowth as well as programmed cell death. p38-alpha is involved with the regulation of pro-inflammatory cytokines, including TNF-a. In the central nervous system, p38-alpha regulates neuronal death and neurite degeneration, and it is a common target of Alzheimer's disease therapies. JNK3 is a neuronal-specific protein isoform of the JNKs. It is involved with the regulation of apoptosis. JNK3 also plays a role in modulating the response of cytokines, growth factors, and oxidative stress.

As used herein, the term "modulating activity of a mitogen-activated protein kinase" refers to changing, manipulating, and/or adjusting the activity of a mitogen-activated protein kinase. In one embodiment, modulating the activity of a MAPK can influence neural health, neurogenesis, neural growth and differentiation, and neurodegenerative diseases.

5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, or crystalline form 1 of 5-F-NiPT iodide, or a compound of formula (I) or formula (III) of this disclosure may be used to modulate neurogenesis, comprising administering a composition of the invention. As used herein, the term "modulating neurogenesis" refers to changing, manipulating, and/or adjusting the growth and development of neural tissue. In one embodiment, neurogenesis comprises adult neurogenesis, in which new neural stem cells are generated from neural stem cells in an adult animal. In one embodiment, modulating neurogenesis comprises increasing and/or enhancing the rate at which new neural tissue is developed.

5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, or crystalline form 1 of 5-F-NiPT iodide, or a compound of formula (I) or formula (III) of this disclosure may be used to modulate neurite outgrowth, comprising administering a composition of the invention. As used herein, the term "modulating neurite outgrowth" refers to changing, manipulating, and/or adjusting the growth and development of neural projections, or "neurites." In one embodiment, neurogenesis comprises modulating the growth of new neurites, the number of neurites per neuron, and/or neurite length. In one embodiment, modulating neurite outgrowth comprises increasing and/or enhancing the rate and/or length at which neurites develop.

5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, or crystalline form 1 of 5-F-NiPT iodide, or a compound of formula (I) or formula (III) of this disclosure may be used to prevent and/or treat sexual health disorders including, but not limited to, hypoactive sexual desire disorder, hyperactive sexual desire disorder, orgasmic disorder, arousal disorder, vaginismus, and dyspareunia. In some embodiments, the disorder is a male sexual dysfunction disorder. In some embodiments, the disorder is a female sexual dysfunction disorder.

5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, or crystalline form 1 of 5-F-NiPT iodide, or a compound of formula (I) or formula (III) of this disclosure may be used to prevent and/or treat women's health disorders including, but not limited to, menstrual cramping, dysmenorrhea, post-hysterectomy pain, vaginal or vulvar vestibule mucosa disorder, menopausal-related disorders, vaginal atrophy, or vulvar vestibulitis.

Compositions

The disclosure also relates to compositions comprising an effective amount of 5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, or crystalline form 1 of 5-F-NiPT iodide, or a compound of formula (I) or formula (III) of this disclosure and an excipient (e.g., a pharmaceutically-acceptable excipient). In another embodiment, the disclosure also relates to pharmaceutical compositions comprising a therapeutically effective amount of 5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, or crystalline form 1 of 5-F-NiPT iodide, or a compound of formula (I) or formula (III) of this disclosure and a pharmaceutically acceptable excipient (also known as a pharmaceutically acceptable carrier). As discussed above, 5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, or crystalline form 1 of 5-F-NiPT iodide, or a compound of formula (I) or formula (III) of this disclosure of the disclosure may be, for example, therapeutically useful to prevent and/or treat the psychological disorders, brain disorders, pain, and inflammation as well as the other disorders described herein.

A composition or a pharmaceutical composition of the disclosure may be in any form which contains 5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, or crystalline form 1 of 5-F-NiPT iodide, or a compound of formula (I) or formula (III) of this disclosure. The composition may be, for example, a tablet, capsule, liquid suspension, injectable, topical, or transdermal. The compositions generally contain, for example, about 1% to about 99% by weight of 5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, or crystalline form 1 of 5-F-NiPT iodide, or a compound of formula (I) or formula (III) of this disclosure and, for example, 99% to 1% by weight of at least one suitable pharmaceutically acceptable excipient. In one embodiment, the composition may be between about 5% and about 75% by weight of 5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, or crystalline form 1 of 5-F-NiPT iodide, or a compound of formula (I) or formula (III) of this disclosure, with the rest being at least one suitable pharmaceutically acceptable excipient or at least one other adjuvant, as discussed below.

Published US applications US 2018/0221396 A1 and US 2019/0142851 A1 disclose compositions comprising a combination of a first purified psilocybin derivative with a second purified psilocybin derivative, with one or two purified cannabinoids or with a purified terpene. Various ratios of these components in the composition are also disclosed. The disclosures of US 2018/0221396 A1 and US 2019/0142851 A1 are incorporated herein by reference. According to this disclosure, 5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, or crystalline form 1 of 5-F-NiPT iodide, or a compound of formula (I) or formula (III) of this disclosure may be used as the "first purified psilocybin derivative" in the compositions described in US 2018/0221396 A1 and US 2019/0142851 A1. Accordingly, this disclosure provides a composition comprising: a first component comprising 5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, or crystalline form 1 of 5-F-NiPT iodide, or a compound of formula (I) or formula (III) of this disclosure; at least one second component selected from at least one of (a) a serotonergic drug, (b) a purified psilocybin derivative, (c) a purified cannabinoid, and (d) a purified terpene; and at least one pharmaceutically-acceptable excipient or at least one other adjuvant. Such a composition may be a pharmaceutical composition wherein the components are present individually in therapeutically effective amounts or by combination in a therapeutically effective amount to treat a disease, disorder, or condition as described herein.

When used in such compositions as a first component comprising 5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, or crystalline form 1 of 5-F-NiPT iodide, or a compound of formula (I) or formula (III) of this disclosure with a second component selected from at least one of (a) a serotonergic drug, (b) a purified psilocybin derivative, (c) a purified cannabinoid, and (d) a purified terpene, the compositions represent particular embodiments of the invention. Compositions having as a first component 5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, or crystalline form 1 of 5-F-NiPT iodide, or a compound of formula (I) or formula (III) of this disclosure with a second component selected from at least one of (e) an adrenergic drug, (f) a dopaminergic drug, (g) a monoamine oxidase inhibitor, (h) a purified erinacine, and (i) a purified hericenone represent additional particular embodiments of the invention represented by the compositions having 5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, or crystalline form 1 of 5-F-NiPT iodide, or a compound of formula (I) or formula (III) of this disclosure. In some embodiments, the first and second components can be administered at the same time (e.g., together in the same composition), or at separate times over the course of treating a patient in need thereof. Such a composition may be a pharmaceutical composition wherein the components are present individually in therapeutically effective amounts or by combination in a therapeutically effective amount to treat a disease, disorder, or condition as described herein.

Within the context of this disclosure, the term "purified" means separated from other materials, such as plant or fungal material, e.g., protein, chitin, cellulose, or water. In one embodiment, the term "purified" refers to a compound substantially free of other materials. In one embodiment, the term "purified" refers to a compound that is substantially free from a second tryptamine compound. In one embodiment, the term "purified" refers to a compound substantially free from histidine. In one embodiment, the term "purified" refers to a compound substantially free from a biological material, such as mold, fungus, plant matter, or bacteria. In one embodiment, the term "purified" refers to a compound substantially free from a paralytic.

In one embodiment, the term "purified" refers to a compound which has been separated from other compounds that are typically co-extracted when the purified compound is extracted from a naturally occurring organism. In one embodiment, a "purified" psilocybin derivative is partially or completely isolated from other psilocybin derivatives present in a source material, such as a psilocybin-containing mushroom. In one example, "purified" baeocystin is substantially free from psilocybin and/or psilocin. By contrast, traditional psilocybin mushroom extracts (aka crude extracts or fruit body extracts) would be expected to contain an unpredictable and varying amount of psilocybin, psilocin, baeocystin, norbaeocystin, salts thereof, or combinations thereof. Other examples of unpurified psilocybin derivatives would include mycelium containing psilocybin derivatives and/or naturally occurring fungal material such as biological material and/or structural material such as chitin. Similarly, the term "*cannabis* extracts" or "cannabinoid extracts" traditionally refers to whole plants (aka crude or full spectrum extracts) which have not been subjected to further purification to eliminate unwanted molecules that naturally occur in the *cannabis* plant. For example, a "*cannabis* extract comprising cannabidiol" could be expected to include cannabidiol (aka "CBD") and also varying amounts of other compounds, including cannabinoids, terpenes, and other biological material.

In one embodiment, the term "purified" refers to a compound or composition that has been crystallized.

In one embodiment, the term "purified" refers to a compound or composition that has been chromatographed, for example by gas chromatography, liquid chromatography (e.g., LC, HPLC, etc.), etc.

In one embodiment, the term "purified" refers to a compound or composition that has been distilled.

In one embodiment, the term "purified" refers to a compound or composition that has been sublimed.

In one embodiment, the term "purified" refers to a compound or composition that has been subject to two or more steps chosen from crystallization, chromatography, distillation, or sublimation.

In one embodiment, the term "purified" refers to a compound that is between 80-100% pure.

In one embodiment, the term "purified" refers to a compound that is between 90-100% pure.

In one embodiment, the term "purified" refers to a compound that is between 95-100% pure.

In one embodiment, the term "purified" refers to a compound that is between 99-100% pure.

In one embodiment, the term "purified" refers to a compound that is between 99.9-100% pure.

A serotonergic drug refers to a compound that binds to, blocks, or otherwise influences (e.g., via an allosteric reaction) activity at a serotonin receptor as described in paragraphs [0245]-[0253] of US 2018/0221396 A1 and [0305]-[0311] US 2019/0142851 A1 as well as the disclosed exemplary embodiments. Exemplary psilocybin derivatives include but are not limited to psilocybin itself and the psilocybin derivatives described in paragraphs [0081]-[0109] of US 2018/0221396 A1 and [0082]-[0110] US 2019/0142851 A1 as well as the disclosed exemplary embodiments. Exemplary cannabinoids include but are not limited to the cannabinoids described in paragraphs [0111]-[0145] of US 2018/0221396 A1 and [0112]-[0146] US 2019/0142851 A1 as well as the disclosed exemplary embodiments. Exemplary terpenes include but are not limited to the terpenes described in paragraphs [0160]-[0238] of US 2018/0221396 A1 and [0161]-[0300] US 2019/0142851 A1 as well as the disclosed exemplary embodiments.

A pharmaceutical formulation of the disclosure may comprise, consist essentially of, or consist of (a) 5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, or crystalline form 1 of 5-F-NiPT iodide, or a compound of formula (I) or formula (III) of this disclosure and (b) at least one second active compound selected from a serotonergic drug, a purified psilocybin derivative, a purified cannabinoid, a purified terpene, an adrenergic drug, a dopaminergic drug, a monoamine oxidase inhibitor, a purified erinacine, and a purified hericenone, and (c) a pharmaceutically acceptable excipient. In some embodiments, 5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, or crystalline form 1 of 5-F-NiPT iodide, or a compound of formula (I) or formula (III) of this disclosure and the second active compound(s) are each present in a therapeutically effective amount using purposefully engineered and unnaturally occurring molar ratios. Exemplary molar ratios of 5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, or crystalline form 1 of 5-F-NiPT iodide, or a compound of formula (I) or formula (III) of this disclosure to the second active compound in a composition of the disclosure include but are not limited to from about 0.1:100 to about 100:0.1, from about 1:100 to about 100:1, from about 1:50 to about 50:1, from about 1:25 to about 25:1, from about 1:20 to about 20:1, from about 1:10 to about 10:1, from about 1:5 to about 5:1, from about 1:2 to about 2:1 or may be about 1:1.

A pharmaceutical formulation of the disclosure may comprise a composition containing 5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, or crystalline form 1 of 5-F-NiPT iodide, or a compound of formula (I) or formula (III) of this disclosure and a serotonergic drug, a purified psilocybin derivative, a purified cannabinoid, or a purified terpene, each present in a therapeutically effective amount using purposefully engineered and unnaturally occurring molar ratios. Published US applications US 2018/0221396 A1 and US 2019/0142851 A1 disclose compositions comprising a combination of a purified psilocybin derivative with a second purified psilocybin derivative, with one or two purified cannabinoids or with a purified terpene. According to this disclosure composition containing 5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, or crystalline form 1 of 5-F-NiPT iodide, or a compound of formula (I) or formula (III) of this disclosure may be used in place of a "purified psilocybin derivative" in the compositions described in US 2018/0221396 A1 and US 2019/0142851 A1. Accordingly, the disclosure provides a pharmaceutical formulation comprising as (a) 5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, or crystalline form 1 of 5-F-NiPT iodide, or a compound of formula (I) or formula (III) of this disclosure and at least one second component selected from (a) a purified psilocybin derivative, (b) a purified cannabinoid, and (c) a purified terpene; and at least one pharmaceutically-acceptable excipient or at least one other adjuvant, as described herein. Such a composition may be a pharmaceutical composition wherein the components are present individually in therapeutically effective amounts or by combination in a therapeutically effective amount to treat a disease, disorder, or condition as described herein.

A serotonergic drug refers to a compound that binds to, blocks, or otherwise influences (e.g., via an allosteric reaction) activity at a serotonin receptor as described in paragraphs [0245]-[0253] of US 2018/0221396 A1 and [0305]-[0311] US 2019/0142851 A1 as well as the disclosed exemplary embodiments. Some exemplary serotonergic drugs include SSRIs and SNRIs. Some examples of specific serotonergic drugs include the following molecules, including any salts, solvates, or polymorphs thereof: 6-allyl-N,N-diethyl-NL; N,N-dibutyl-T; N,N-diethyl-T; N,N-diisopropyl-T; 5-methyoxy-alpha-methyl-T; N,N-dimethyl-T; 2,alpha-dimethyl-T; alpha,N-dimethyl-T; N,N-dipropyl-T; N-ethyl-N-isopropyl-T; alpha-ethyl-T; 6-N,N-Triethyl-NL; 3,4-dihydro-7-methoxy-1-methyl-C; 7-methyoxy-1-methyl-C; N,N-dibutyl-4-hydroxy-T; N,N-diethyl-4-hydroxy-T; N,N-diisopropyl-4-hydroxy-T; N,N-dimethyl-4-hydroxy-T; N,N-dimethyl-5-hydroxy-T; N, N-dipropyl-4-hydroxy-T; N-ethyl-4-hydroxy-N-methyl-T; 4-hydroxy-N-isopropyl-N-methyl-T; 4-hydroxy-N-methyl-N-propyl-T; 4-hydroxy-N,N-tetramethylene-T; ibogaine; N,N-diethyl-L; N-butyl-N-methyl-T; N,N-diisopropyl-4,5-methylenedioxy-T; N,N-diisopropyl-5,6-methylenedioxy-T; N,N-dimethyl-4,5-methylenedioxy-T; N,N-dimethyl-5,6-methylenedioxy-T; N-isopropyl-N-methyl-5,6-methylenedioxy-T; N,N-diethyl-2-methyl-T; 2-N,N-trimethyl-T; N-acetyl-5-methoxy-T; N,N-diethyl-5-methoxy-T; N,N-diisopropyl-5-methoxy-T; 5-methoxy-N,N-dimethyl-T; N-isopropyl-4-methoxy-N-methyl-T; N-isopropyl-5-methoxy-N-methyl-T; 5,6-dimethoxy-N-isopropyl-N-methyl-T; 5-methoxy-N-methyl-T; 5-methoxy-N,N-tetramethylene-T; 6-methoxy-1-methyl-1,2,3,4-tetrahydro-C; 5-methoxy-2-N,N-trimethyl-T; N,N-dimethyl-5-methylthio-T; N-isopropyl-N-methyl-T; alpha-methyl-T; N-ethyl-T; N-methyl-T; 6-propyl-N L; N,N-tetramethylene-T; tryptamine; 7-methoxy-1-methyl-1,2,3,4-tetrahydro-C; and alpha,N-dimethyl-5-methoxy-T. For additional information regarding these compounds see Shulgin, A. T., & Shulgin, A. (2016). Tihkal: The Continuation. Berkeley, Calif.: Transform Press. In one embodiment, a serotonergic drug is chosen from alprazolam, amphetamine, aripiprazole, azapirone, a barbiturate, bromazepam, bupropion, buspirone, a cannabinoid, chlordiazepoxide, citalopram, clonazepam, clorazepate, dextromethorphan, diazepam, duloxetine, escitalopram, fluoxetine, flurazepam, fluvoxamine, lorazepam, lysergic acid diethylamide, lysergamide, 3,4-methylenedioxymethamphetamine, milnacipran, mirtazapine, naratriptan, paroxetine, pethidine, phenethylamine, psicaine, oxazepam, reboxetine, serenic, serotonin, sertraline, temazepam, tramadol, triazolam, a tryptamine, venlafaxine, vortioxetine, and/or derivatives thereof. In an exemplary embodiment, the serotonergic drug is 3,4-methylenedioxymethamphetamine.

Exemplary psilocybin derivatives include but are not limited to psilocybin itself and the psilocybin derivatives described in paragraphs [0081]-[0109] of US 2018/0221396 A1 and [0082]-[0110] US 2019/0142851 A1 as well as the disclosed exemplary embodiments, incorporated here by reference. In one embodiment, the compositions disclosed herein comprise one or more purified psilocybin derivatives chosen from: [3-(2-dimethylaminoethyl)-1H-indol-4-yl]dihydrogen phosphate; 4-hydroxytryptamine; 4-hydroxy-N,N-dimethyltryptamine; [3-(2-methylaminoethyl)-1H-indol-4-yl]dihydrogen phosphate; 4-hydroxy-N-methyltryptamine; [3-(aminoethyl)-1H-indol-4-yl]dihydrogen phosphate; [3-(2-trimethylaminoethyl)-1H-indol-4-yl]dihydrogen phosphate; and 4-hydroxy-N,N,N-trimethyltryptamine.

Exemplary cannabinoids include but are not limited to the cannabinoids described in paragraphs [0111]-[0145] of US 2018/0221396 A1 and [0112]-[0146] US 2019/0142851 A1 as well as the disclosed exemplary embodiments. Examples of cannabinoids within the context of this disclosure include the following molecules: cannabichromene (CBC); cannabichromenic acid (CBCA); cannabichromevarin (CBCV); cannabichromevarinic acid (CBCVA); cannabicyclol (CBL); cannabicyclolic acid (CBLA); cannabicyclovarin (CBLV); cannabidiol (CBD); cannabidiol monomethylether (CBDM); cannabidiolic acid (CBDA); cannabidiorcol (CBD-C1); cannabidivarin (CBDV); cannabidivarinic acid (CBDVA); cannabielsoic acid B (CBEA-B); cannabielsoin (CBE); cannabielsoin acid A (CBEA-A); cannabigerol (CBG); cannabigerol monomethylether (CBGM); cannabigerolic acid (CBGA); cannabigerolic acid monomethylether (CBGAM); cannabigerovarin (CBGV); cannabigerovarinic acid (CBGVA); cannabinodiol (CBND); cannabinodivarin (CBVD); cannabinol (CBN); cannabinol methylether (CBNM); cannabinol-C2 (CBN-C2); cannabinol-C4 (CBN-C4); cannabinolic acid (CBNA); cannabiorcol (CBN-C1); cannabivarin (CBV); cannabitriol (CBT); cannabitriolvarin (CBTV); 10-ethoxy-9-hydroxy-delta-6a-tetrahydrocannabinol; cannabicitran (CBTC); cannabiripsol (CBR); 8,9-dihydroxy-delta-6a-tetrahydrocannabinol; delta-8-tetrahydrocannabinol (Δ8-THC); delta-8-tetrahydrocannabinolic acid (Δ8-THCA); delta-9-tetrahydrocannabinol (THC); delta-9-tetrahydrocannabinol-C4 (THC-C4); delta-9-tetrahydrocannabinolic acid A (THCA-A); delta-9-tetrahydrocannabinolic acid B (THCA-B); delta-9-tetrahydrocannabinolic acid-C4 (THCA-C4); delta-9-tetrahydrocannabiorcol (THC-C1); delta-9-tetrahydrocannabiorcolic acid (THCA-C1); delta-9-tetrahydrocannabivarin (THCV); delta-9-tetrahydrocannabivarinic acid (THCVA); 10-oxo-delta-6a- tetrahydrocannabinol (OTHC); cannabichromanon (CBCF); cannabifuran (CBF); cannabiglendol; delta-9-cis-tetrahydrocannabinol (cis-THC); trihydroxy-delta-9-tetrahydrocannabinol (triOH-THC); dehydrocannabifuran (DCBF); and 3,4,5,6-tetrahydro-7-hydroxy-alpha-alpha-2-trimethyl-9-n-propyl-2,6-methano-2H-1-benzoxocin-5-methanol. In one embodiment, the purified cannabinoid is chosen from THC, THCA, THCV, THCVA, CBC, CBCA, CBCV, CBCVA, CBD, CBDA, CBDV, CBVD, CBDVA, CBG, CBGA, CBGV, or CBGVA.

Exemplary terpenes include but are not limited to the terpenes described in paragraphs [0160]-[0238] of US 2018/0221396 A1 and [0161]-[0300] US 2019/0142851 A1 as well as the disclosed exemplary embodiments. In one embodiment, a purified terpene is chosen from acetanisole, acetyl cedrene, anethole, anisole, benzaldehyde, bornyl acetate, borneol, cadinene, cafestol, caffeic acid, camphene, camphor, capsaicin, carene, carotene, carvacrol, carvone, caryophyllene, caryophyllene, caryophyllene oxide, cedrene, cedrene epoxide, cecanal, cedrol, cembrene, cinnamaldehyde, cinnamic acid, citronellal, citronellol, cymene, eicosane, elemene, estragole, ethyl acetate, ethyl cinnamate, ethyl maltol, eucalyptol/1,8-cineole, eudesmol, eugenol, euphol, farnesene, farnesol, fenchone, geraniol, geranyl acetate, guaia-1(10),11-diene, guaiacol, guaiol, guaiene, gurjunene, herniarin, hexanaldehyde, hexanoic acid, humulene, ionone, ipsdienol, isoamyl acetate, isoamyl alcohol, isoamyl formate, isoborneol, isomyrcenol, isoprene, isopulegol, isovaleric acid, lavandulol, limonene, gamma-linolenic acid, linalool, longifolene, lycopene, menthol, methyl butyrate, 3-mercapto-2-methylpentanal, beta-mercaptoethanol, mercaptoacetic acid, methyl salicylate, methylbutenol, methyl-2-methylvalerate, methyl thiobutyrate, myrcene, gamma-muurolene, nepetalactone, nerol, nerolidol, neryl acetate, nonanaldehyde, nonanoic acid, ocimene, octanal, octanoic acid, pentyl butyrate, phellandrene, phenylacetaldehyde, phenylacetic acid, phenylethanethiol, phytol, pinene, propanethiol, pristimerin, pulegone, retinol, rutin, sabinene, squalene, taxadiene, terpineol, terpine-4-ol, terpinolene, thujone, thymol, umbelliferone, undecanal, verdoxan, or vanillin. In one embodiment, a purified terpene is chosen from bornyl acetate, alpha-bisabolol, borneol, camphene, camphor, carene, caryophyllene, cedrene, cymene, elemene, eucalyptol, eudesmol, farnesene, fenchol, geraniol, guaiacol, humulene, isoborneol, limonene, linalool, menthol, myrcene, nerolidol, ocimene, phellandrene, phytol, pinene, pulegone, sabinene, terpineol, terpinolene, or valencene.

As used herein, the term "adrenergic drug" refers to a compound that binds, blocks, or otherwise influences (e.g., via an allosteric reaction) activity at an adrenergic receptor. In one embodiment, an adrenergic drug binds to an adrenergic receptor. In one embodiment, an adrenergic drug indirectly affects an adrenergic receptor, e.g., via interactions affecting the reactivity of other molecules at the adrenergic receptor. In one embodiment, an adrenergic drug is an agonist, e.g., a compound activating an adrenergic receptor. In one embodiment, an adrenergic drug is an antagonist, e.g., a compound binding but not activating an adrenergic receptor, e.g., blocking a receptor. In one embodiment, an adrenergic drug is an effector molecule, e.g., a compound binding to an enzyme for allosteric regulation. In one embodiment, an adrenergic drug acts (either directly or indirectly) at more than one type of receptor (e.g., 5HT, dopamine, adrenergic, acetylcholine, etc.).

In one embodiment, an adrenergic drug is an antidepressant. In one embodiment, an adrenergic drug is a norepinephrine transporter inhibitor. In one embodiment, an adrenergic drug is a vesicular monoamine transporter inhibitor. In one embodiment, an adrenergic drug is chosen from adrenaline, agmatine, amoxapine, aptazapine, atomoxetine, bupropion, clonidine, doxepin, duloxetine, esmirtazpine, mianserin, ketanserin, mirabegron, mirtazapine, norepinephrine, phentolamine, phenylephrine, piperoxan, reserpine, ritodrine, setiptiline, tesofensine, timolol, trazodone, trimipramine, or xylazine.

As used herein, the term "dopaminergic drug" refers to a compound that binds, blocks, or otherwise influences (e.g., via an allosteric reaction) activity at a dopamine receptor. In one embodiment, a dopaminergic drug binds to a dopamine receptor. In one embodiment, a dopaminergic drug indirectly affects a dopamine receptor, e.g., via interactions affecting the reactivity of other molecules at the dopamine receptor. In one embodiment, a dopaminergic drug is an agonist, e.g., a compound activating a dopamine receptor. In one embodiment, a dopaminergic drug is an antagonist, e.g., a compound binding but not activating a dopamine receptor, e.g., blocking a receptor. In one embodiment, a dopaminergic drug is an effector molecule, e.g., a compound binding to an enzyme for allosteric regulation. In one embodiment, a dopaminergic drug acts (either directly or indirectly) at more than one type of receptor (e.g., 5HT, dopamine, adrenergic, acetylcholine, etc.).

In one embodiment, a dopaminergic drug is a dopamine transporter inhibitor. In one embodiment, a dopaminergic drug is a vesicular monoamine transporter inhibitor. In one embodiment, a dopaminergic drug is chosen from amineptine, apomorphine, benzylpiperazine, bromocriptine, cabergoline, chlorpromazine, clozapine, dihydrexidine, domperidone, dopamine, fluphenazine, haloperidol, ketamine, loxapine, methamphetamine, olanzapine, pemoline, perphenazine, pergolide, phencyclidine, phenethylamine, phenmetrazine, pimozide, piribedil, a psychostimulant, reserpine, risperidone, ropinirole, tetrabenazine, or thioridazine.

As used herein, the term "monoamine oxidase inhibitor" (MAOI) refers to a compound that blocks the actions of monoamine oxidase enzymes. In one embodiment, a MAOI inhibits the activity of one or both monoamine oxidase A and monoamine oxidase B. In one embodiment a MAOI is a reversible inhibitor of monoamine oxidase A. In one embodiment a MAOI is a drug chosen from isocarboxazid, phenelzine, or tranylcypromine. In one embodiment, a MAOI is β-carboline, pinoline, harmane, harmine, harmaline, harmalol, tetrahydroharmine, 9-methyl-β-carboline, or 3-carboxy-tetrahydrononharman.

In one embodiment, the compositions and methods disclosed herein include one or more purified erinacine molecules. In one embodiment, the compositions and methods disclosed herein comprise purified erinacine A. In one embodiment, the compositions and methods disclosed herein comprise erinacine B. In one embodiment, the compositions and methods disclosed herein comprise erinacine C. In one embodiment, the compositions and methods disclosed herein comprise erinacine D. In one embodiment, the compositions and methods disclosed herein comprise erinacine E. In one embodiment, the compositions and methods disclosed herein comprise erinacine F. In one embodiment, the compositions and methods disclosed herein comprise erinacine G. In one embodiment, the compositions and methods disclosed herein comprise erinacine H. In one embodiment, the compositions and methods disclosed herein comprise erinacine I. In one embodiment, the compositions and methods disclosed herein comprise erinacine J. In one embodiment, the compositions and methods disclosed herein comprise erinacine K. In one embodiment, the compositions and methods disclosed herein comprise erinacine P. In one embodiment, the compositions and methods disclosed herein comprise erinacine Q. In one embodiment, the compositions and methods disclosed herein comprise erinacine R. In one embodiment, the compositions and methods disclosed herein comprise erinacine S.

In one embodiment, the compositions and methods disclosed herein include one or more purified hericenone molecules. In one embodiment, the compositions and methods disclosed herein comprise purified hericenone A. In one embodiment, the compositions and methods disclosed herein comprise purified hericenone B. In one embodiment, the compositions and methods disclosed herein comprise purified hericenone C. In one embodiment, the compositions and methods disclosed herein comprise purified hericenone D. In one embodiment, the compositions and methods disclosed herein comprise purified hericenone E. In one embodiment, the compositions and methods disclosed herein comprise purified hericenone F. In one embodiment, the compositions and methods disclosed herein comprise purified hericenone G. In one embodiment, the compositions and methods disclosed herein comprise purified hericenone H.

Exemplary compositions of 5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, or crystalline form 1 of 5-F-NiPT iodide, or a compound of formula (I) or formula (III) of this disclosure and a second compound selected from a serotonergic drug, a purified psilocybin derivative, a purified cannabinoid, a purified terpene, an adrenergic drug, a dopaminergic drug, a monoamine oxidase inhibitor, a purified erinacine, and a purified hericenone in exemplary molar ratios are shown in Table 1. 5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, or crystalline form 1 of 5-F-NiPT iodide, or a compound of formula (I) or formula (III) of this disclosure may be any one of the exemplary embodiments described above including the crystalline forms as disclosed herein.

TABLE 1

| Second Compound | Molar ratio of 5-Cl-NiPT iodide or crystalline 5-Cl-NiPT iodide, such as crystalline form 1 of 5-Cl-NiPT iodide: second compound | Molar ratio of 5-MeO-NiPT iodide or crystalline 5-MeO-NiPT iodide, such as crystalline form 1 of 5-MeO-NiPT iodide: second compound | Molar ratio of 5-Me-NiPT iodide or crystalline 5-Me-NiPT iodide, such as crystalline form 1 of 5-Me-NiPT iodide: second compound | Molar ratio of 2-Me-NiPT iodide or crystalline 2-Me-NiPT iodide, such as crystalline form 1 of 2-Me-NiPT iodide: second compound | Molar ratio of 7-Me-NiPT iodide or crystalline 7-Me-NiPT iodide, such as crystalline form 1 of 7-Me-NiPT iodide: second compound | Molar ratio of 5-F-NiPT iodide or crystalline 5-F-NiPT iodide, such as crystalline form 1 of 5-F-NiPT iodide: second compound | Molar ratio of a compound of formula (I) or formula (III) of the disclosure: second compound |
|---|---|---|---|---|---|---|---|
| 3,4-methylene-dioxy-methamphet-amine | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |
| Citalopram | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |

TABLE 1-continued

| Second Compound | Molar ratio of 5-Cl-NiPT iodide or crystalline 5-Cl-NiPT iodide, such as crystalline form 1 of 5-Cl-NiPT iodide: second compound | Molar ratio of 5-MeO-NiPT iodide or crystalline 5-MeO-NiPT iodide, such as crystalline form 1 of 5-MeO-NiPT iodide: second compound | Molar ratio of 5-Me-NiPT iodide or crystalline 5-Me-NiPT iodide, such as crystalline form 1 of 5-Me-NiPT iodide: second compound | Molar ratio of 2-Me-NiPT iodide or crystalline 2-Me-NiPT iodide, such as crystalline form 1 of 2-Me-NiPT iodide: second compound | Molar ratio of 7-Me-NiPT iodide or crystalline 7-Me-NiPT iodide, such as crystalline form 1 of 7-Me-NiPT iodide: second compound | Molar ratio of 5-F-NiPT iodide or crystalline 5-F-NiPT iodide, such as crystalline form 1 of 5-F-NiPT iodide: second compound | Molar ratio of a compound of formula (I) or formula (III) of the disclosure: second compound |
|---|---|---|---|---|---|---|---|
| Escitalopram | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |
| Fluoxetine | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |
| Paroxetine | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |
| Sertraline | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |
| Duloxetine | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |

TABLE 1-continued

| Second Compound | Molar ratio of 5-Cl-NiPT iodide or crystalline 5-Cl-NiPT iodide, such as crystalline form 1 of 5-Cl-NiPT iodide: second compound | Molar ratio of 5-MeO-NiPT iodide or crystalline 5-MeO-NiPT iodide, such as crystalline form 1 of 5-MeO-NiPT iodide: second compound | Molar ratio of 5-Me-NiPT iodide or crystalline 5-Me-NiPT iodide, such as crystalline form 1 of 5-Me-NiPT iodide: second compound | Molar ratio of 2-Me-NiPT iodide or crystalline 2-Me-NiPT iodide, such as crystalline form 1 of 2-Me-NiPT iodide: second compound | Molar ratio of 7-Me-NiPT iodide or crystalline 7-Me-NiPT iodide, such as crystalline form 1 of 7-Me-NiPT iodide: second compound | Molar ratio of 5-F-NiPT iodide or crystalline 5-F-NiPT iodide, such as crystalline form 1 of 5-F-NiPT iodide: second compound | Molar ratio of a compound of formula (I) or formula (III) of the disclosure: second compound |
|---|---|---|---|---|---|---|---|
| [3-(2-dimethylaminoethyl)-1H-indol-4-yl] dihydrogen phosphate | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |
| 4-hydroxytryptamine | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |
| 4-hydroxy-N,N-dimethyltryptamine | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |
| [3-(2-methylaminoethyl)-1H-indol-4-yl] dihydrogen phosphate | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |
| 4-hydroxy-N-methyltryptamine | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |

TABLE 1-continued

| Second Compound | Molar ratio of 5-Cl-NiPT iodide or crystalline 5-Cl-NiPT iodide, such as crystalline form 1 of 5-Cl-NiPT iodide: second compound | Molar ratio of 5-MeO-NiPT iodide or crystalline 5-MeO-NiPT iodide, such as crystalline form 1 of 5-MeO-NiPT iodide: second compound | Molar ratio of 5-Me-NiPT iodide or crystalline 5-Me-NiPT iodide, such as crystalline form 1 of 5-Me-NiPT iodide: second compound | Molar ratio of 2-Me-NiPT iodide or crystalline 2-Me-NiPT iodide, such as crystalline form 1 of 2-Me-NiPT iodide: second compound | Molar ratio of 7-Me-NiPT iodide or crystalline 7-Me-NiPT iodide, such as crystalline form 1 of 7-Me-NiPT iodide: second compound | Molar ratio of 5-F-NiPT iodide or crystalline 5-F-NiPT iodide, such as crystalline form 1 of 5-F-NiPT iodide: second compound | Molar ratio of a compound of formula (I) or formula (III) of the disclosure: second compound |
|---|---|---|---|---|---|---|---|
| [3-(amino-ethyl)-1H-indol-4-yl] dihydrogen phosphate | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |
| [3-(2-trimethyl-aminoethyl)-1H-indol-4-yl] dihydrogen phosphate | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |
| 4-hydroxy-N,N,N-trimethyl-tryptamine | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |
| THC | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |
| CBC | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |

TABLE 1-continued

| Second Compound | Molar ratio of 5-Cl-NiPT iodide or crystalline 5-Cl-NiPT iodide, such as crystalline form 1 of 5-Cl-NiPT iodide: second compound | Molar ratio of 5-MeO-NiPT iodide or crystalline 5-MeO-NiPT iodide, such as crystalline form 1 of 5-MeO-NiPT iodide: second compound | Molar ratio of 5-Me-NiPT iodide or crystalline 5-Me-NiPT iodide, such as crystalline form 1 of 5-Me-NiPT iodide: second compound | Molar ratio of 2-Me-NiPT iodide or crystalline 2-Me-NiPT iodide, such as crystalline form 1 of 2-Me-NiPT iodide: second compound | Molar ratio of 7-Me-NiPT iodide or crystalline 7-Me-NiPT iodide, such as crystalline form 1 of 7-Me-NiPT iodide: second compound | Molar ratio of 5-F-NiPT iodide or crystalline 5-F-NiPT iodide, such as crystalline form 1 of 5-F-NiPT iodide: second compound | Molar ratio of a compound of formula (I) or formula (III) of the disclosure: second compound |
|---|---|---|---|---|---|---|---|
| CBD | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |
| CBG | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |
| Myrcene | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |
| Pinene | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |
| Caryophyllene | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |

TABLE 1-continued

| Second Compound | Molar ratio of 5-Cl-NiPT iodide or crystalline 5-Cl-NiPT iodide, such as crystalline form 1 of 5-Cl-NiPT iodide: second compound | Molar ratio of 5-MeO-NiPT iodide or crystalline 5-MeO-NiPT iodide, such as crystalline form 1 of 5-MeO-NiPT iodide: second compound | Molar ratio of 5-Me-NiPT iodide or crystalline 5-Me-NiPT iodide, such as crystalline form 1 of 5-Me-NiPT iodide: second compound | Molar ratio of 2-Me-NiPT iodide or crystalline 2-Me-NiPT iodide, such as crystalline form 1 of 2-Me-NiPT iodide: second compound | Molar ratio of 7-Me-NiPT iodide or crystalline 7-Me-NiPT iodide, such as crystalline form 1 of 7-Me-NiPT iodide: second compound | Molar ratio of 5-F-NiPT iodide or crystalline 5-F-NiPT iodide, such as crystalline form 1 of 5-F-NiPT iodide: second compound | Molar ratio of a compound of formula (I) or formula (III) of the disclosure: second compound |
|---|---|---|---|---|---|---|---|
| Limonene | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |
| Humulene | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |
| Linalool | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |
| Adrenaline | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |
| Amineptine | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |

TABLE 1-continued

| Second Compound | Molar ratio of 5-Cl-NiPT iodide or crystalline 5-Cl-NiPT iodide, such as crystalline form 1 of 5-Cl-NiPT iodide: second compound | Molar ratio of 5-MeO-NiPT iodide or crystalline 5-MeO-NiPT iodide, such as crystalline form 1 of 5-MeO-NiPT iodide: second compound | Molar ratio of 5-Me-NiPT iodide or crystalline 5-Me-NiPT iodide, such as crystalline form 1 of 5-Me-NiPT iodide: second compound | Molar ratio of 2-Me-NiPT iodide or crystalline 2-Me-NiPT iodide, such as crystalline form 1 of 2-Me-NiPT iodide: second compound | Molar ratio of 7-Me-NiPT iodide or crystalline 7-Me-NiPT iodide, such as crystalline form 1 of 7-Me-NiPT iodide: second compound | Molar ratio of 5-F-NiPT iodide or crystalline 5-F-NiPT iodide, such as crystalline form 1 of 5-F-NiPT iodide: second compound | Molar ratio of a compound of formula (I) or formula (III) of the disclosure: second compound |
|---|---|---|---|---|---|---|---|
| Erinacine A | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |
| Hericenone A | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |
| Phenelzine | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |

Exemplary pharmaceutical compositions of 5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, or crystalline form 1 of 5-F-NiPT iodide, or a compound of formula (I) or formula (III) of this disclosure and a second compound selected from a serotonergic drug, a purified psilocybin derivative, a purified cannabinoid, a purified terpene, an adrenergic drug, a dopaminergic drug, a monoamine oxidase inhibitor, a purified erinacine, and a purified hericenone and an excipient with exemplary molar ratios of 5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, or crystalline form 1 of 5-F-NiPT iodide, or a compound of formula (I) or formula (III) of this disclosure to the second compound are shown in Table 2. 5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, or crystalline form 1 of 5-F-NiPT iodide, or a compound of formula (I) or formula (III) of this disclosure may be any one of the exemplary embodiments described above including the crystalline forms as disclosed herein.

TABLE 2

| Second Compound | Molar ratio of 5-Cl-NiPT iodide or crystalline 5-Cl-NiPT iodide, such as crystalline form 1 of 5-Cl-NiPT iodide: second compound | Molar ratio of 5-MeO-NiPT iodide or crystalline 5-MeO-NiPT iodide, such as crystalline form 1 of 5-MeO-NiPT iodide: second compound | Molar ratio of 5-Me-NiPT iodide or crystalline 5-Me-NiPT iodide, such as crystalline form 1 of 5-Me-NiPT iodide: second compound | Molar ratio of 2-Me-NiPT iodide or crystalline 2-Me-NiPT iodide, such as crystalline form 1 of 2-Me-NiPT iodide: second compound | Molar ratio of 7-Me-NiPT iodide or crystalline 7-Me-NiPT iodide, such as crystalline form 1 of 7-Me-NiPT iodide: second compound | Molar ratio of 5-F-NiPT iodide or crystalline 5-F-NiPT iodide, such as crystalline form 1 of 5-F-NiPT iodide: second compound | Molar ratio of a compound of formula (I) or formula (III) of the disclosure: second compound |
|---|---|---|---|---|---|---|---|
| 3,4-methylene-dioxy-methamphetamine | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |
| Citalopram | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |
| Escitalopram | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |
| Fluoxetine | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |
| Paroxetine | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |

TABLE 2-continued

| Second Compound | Molar ratio of 5-Cl-NiPT iodide or crystalline 5-Cl-NiPT iodide, such as crystalline form 1 of 5-Cl-NiPT iodide: second compound | Molar ratio of 5-MeO-NiPT iodide or crystalline 5-MeO-NiPT iodide, such as crystalline form 1 of 5-MeO-NiPT iodide: second compound | Molar ratio of 5-Me-NiPT iodide or crystalline 5-Me-NiPT iodide, such as crystalline form 1 of 5-Me-NiPT iodide: second compound | Molar ratio of 2-Me-NiPT iodide or crystalline 2-Me-NiPT iodide, such as crystalline form 1 of 2-Me-NiPT iodide: second compound | Molar ratio of 7-Me-NiPT iodide or crystalline 7-Me-NiPT iodide, such as crystalline form 1 of 7-Me-NiPT iodide: second compound | Molar ratio of 5-F-NiPT iodide or crystalline 5-F-NiPT iodide, such as crystalline form 1 of 5-F-NiPT iodide: second compound | Molar ratio of a compound of formula (I) or formula (III) of the disclosure: second compound |
|---|---|---|---|---|---|---|---|
| Sertraline | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |
| Duloxetine | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |
| [3-(2-dimethyl-aminoethyl)-1H-indol-4-yl] dihydrogen phosphate | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |
| 4-hydroxy-tryptamine | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |
| 4-hydroxy-N,N-dimethyl-tryptamine | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |

TABLE 2-continued

| Second Compound | Molar ratio of 5-Cl-NiPT iodide or crystalline 5-Cl-NiPT iodide, such as crystalline form 1 of 5-Cl-NiPT iodide: second compound | Molar ratio of 5-MeO-NiPT iodide or crystalline 5-MeO-NiPT iodide, such as crystalline form 1 of 5-MeO-NiPT iodide: second compound | Molar ratio of 5-Me-NiPT iodide or crystalline 5-Me-NiPT iodide, such as crystalline form 1 of 5-Me-NiPT iodide: second compound | Molar ratio of 2-Me-NiPT iodide or crystalline 2-Me-NiPT iodide, such as crystalline form 1 of 2-Me-NiPT iodide: second compound | Molar ratio of 7-Me-NiPT iodide or crystalline 7-Me-NiPT iodide, such as crystalline form 1 of 7-Me-NiPT iodide: second compound | Molar ratio of 5-F-NiPT iodide or crystalline 5-F-NiPT iodide, such as crystalline form 1 of 5-F-NiPT iodide: second compound | Molar ratio of a compound of formula (I) or formula (III) of the disclosure: second compound |
|---|---|---|---|---|---|---|---|
| [3-(2-methyl-aminoethyl)-1H-indol-4-yl] dihydrogen phosphate | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |
| 4-hydroxy-N-methyl-tryptamine | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |
| [3-(amino-ethyl)-1H-indol-4-yl] dihydrogen phosphate | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |
| [3-(2-trimethyl aminoethyl)-1H-indol-4-yl] dihydrogen phosphate | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |
| 4-hydroxy-N,N,N-trimethyl-tryptamine | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |

TABLE 2-continued

| Second Compound | Molar ratio of 5-Cl-NiPT iodide or crystalline 5-Cl-NiPT iodide, such as crystalline form 1 of 5-Cl-NiPT iodide: second compound | Molar ratio of 5-MeO-NiPT iodide or crystalline 5-MeO-NiPT iodide, such as crystalline form 1 of 5-MeO-NiPT iodide: second compound | Molar ratio of 5-Me-NiPT iodide or crystalline 5-Me-NiPT iodide, such as crystalline form 1 of 5-Me-NiPT iodide: second compound | Molar ratio of 2-Me-NiPT iodide or crystalline 2-Me-NiPT iodide, such as crystalline form 1 of 2-Me-NiPT iodide: second compound | Molar ratio of 7-Me-NiPT iodide or crystalline 7-Me-NiPT iodide, such as crystalline form 1 of 7-Me-NiPT iodide: second compound | Molar ratio of 5-F-NiPT iodide or crystalline 5-F-NiPT iodide, such as crystalline form 1 of 5-F-NiPT iodide: second compound | Molar ratio of a compound of formula (I) or formula (III) of the disclosure: second compound |
|---|---|---|---|---|---|---|---|
| THC | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |
| CBC | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |
| CBD | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |
| CBG | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |
| Myrcene | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |

TABLE 2-continued

| Second Compound | Molar ratio of 5-Cl-NiPT iodide or crystalline 5-Cl-NiPT iodide, such as crystalline form 1 of 5-Cl-NiPT iodide: second compound | Molar ratio of 5-MeO-NiPT iodide or crystalline 5-MeO-NiPT iodide, such as crystalline form 1 of 5-MeO-NiPT iodide: second compound | Molar ratio of 5-Me-NiPT iodide or crystalline 5-Me-NiPT iodide, such as crystalline form 1 of 5-Me-NiPT iodide: second compound | Molar ratio of 2-Me-NiPT iodide or crystalline 2-Me-NiPT iodide, such as crystalline form 1 of 2-Me-NiPT iodide: second compound | Molar ratio of 7-Me-NiPT iodide or crystalline 7-Me-NiPT iodide, such as crystalline form 1 of 7-Me-NiPT iodide: second compound | Molar ratio of 5-F-NiPT iodide or crystalline 5-F-NiPT iodide, such as crystalline form 1 of 5-F-NiPT iodide: second compound | Molar ratio of a compound of formula (I) or formula (III) of the disclosure: second compound |
|---|---|---|---|---|---|---|---|
| Pinene | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |
| Caryophyllene | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |
| Limonene | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |
| Humulene | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |
| Linalool | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |

TABLE 2-continued

| Second Compound | Molar ratio of 5-Cl-NiPT iodide or crystalline 5-Cl-NiPT iodide, such as crystalline form 1 of 5-Cl-NiPT iodide: second compound | Molar ratio of 5-MeO-NiPT iodide or crystalline 5-MeO-NiPT iodide, such as crystalline form 1 of 5-MeO-NiPT iodide: second compound | Molar ratio of 5-Me-NiPT iodide or crystalline 5-Me-NiPT iodide, such as crystalline form 1 of 5-Me-NiPT iodide: second compound | Molar ratio of 2-Me-NiPT iodide or crystalline 2-Me-NiPT iodide, such as crystalline form 1 of 2-Me-NiPT iodide: second compound | Molar ratio of 7-Me-NiPT iodide or crystalline 7-Me-NiPT iodide, such as crystalline form 1 of 7-Me-NiPT iodide: second compound | Molar ratio of 5-F-NiPT iodide or crystalline 5-F-NiPT iodide, such as crystalline form 1 of 5-F-NiPT iodide: second compound | Molar ratio of a compound of formula (I) or formula (III) of the disclosure: second compound |
|---|---|---|---|---|---|---|---|
| Adrenaline | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |
| Amineptine | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |
| Erinacine A | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |
| Hericenone A | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |
| Phenelzine | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 | About 1:100 to about 100:1 About 1:25 to about 25:1 About 1:5 to about 5:1 |

An "effective amount" or a "therapeutically effective amount" of 5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, or crystalline form 1 of 5-F-NiPT iodide, or a compound of formula (I) or formula (III) of this disclosure is generally in the range of about 0.1 to about 100 mg daily (oral dose), of about 0.1 to about 50 mg daily (oral dose), of about 0.25 to about 25 mg daily (oral dose), of about 0.1 to about 5 mg daily (oral dose), or of about 0.5 to about 2.5 mg daily (oral dose). The actual amount required for treatment of any particular patient may depend upon a variety of factors including, for example, the disease being treated and its severity; the specific pharmaceutical composition employed; the age, body weight, general health, sex, and diet of the patient; the mode of administration; the time of administration; the route of administration; and the rate of excretion; the duration of the treatment; any drugs used in combination or coincidental with the specific compound employed; and other such factors well known in the medical arts. These factors are discussed in Goodman and Gilman's "The Pharmacological Basis of Therapeutics," Tenth Edition, A. Gilman, J. Hardman and L. Limbird, eds., McGraw-Hill Press, 155-173 (2001), which is incorporated herein by reference. 5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, or crystalline form 1 of 5-F-NiPT iodide, or a compound of formula (I) or formula (III) of this disclosure and pharmaceutical compositions containing it may be used in combination with other agents that are generally administered to a patient being treated for psychological and other disorders discussed above. They may also be co-formulated with one or more of such agents in a single pharmaceutical composition.

Depending on the type of pharmaceutical composition, the pharmaceutically acceptable carrier may be chosen from any one or a combination of carriers known in the art. The choice of the pharmaceutically acceptable carrier depends upon the pharmaceutical form and the desired method of administration to be used. Exemplary carriers include those that do not substantially alter the structure or activity of 5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, or crystalline form 1 of 5-F-NiPT iodide, or a compound of formula (I) or formula (III) of this disclosure, or produce undesirable biological effects or otherwise interact in a deleterious manner with any other component(s) of the pharmaceutical composition.

The pharmaceutical compositions of the disclosure may be know in the pharmaceutical formulation art, for example, see Remington's Pharmaceutical Sciences, 18th Ed., (Mack Publishing Company, Easton, Pa., 1990), which is incorporated herein by reference. In a solid dosage form, 5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, or crystalline form 1 of 5-F-NiPT iodide, or a compound of formula (I) or formula (III) of this disclosure may be admixed with at least one pharmaceutically acceptable excipient such as, for example, sodium citrate or dicalcium phosphate or (a) fillers or extenders, such as, for example, starches, lactose, sucrose, glucose, mannitol, and silicic acid, (b) binders, such as, for example, cellulose derivatives, starch, alginates, gelatin, polyvinylpyrrolidone, sucrose, and gum acacia, (c) humectants, such as, for example, glycerol, (d) disintegrating agents, such as, for example, agar-agar, calcium carbonate, potato or tapioca starch, alginic acid, croscarmellose sodium, complex silicates, and sodium carbonate, (e) solution retarders, such as, for example, paraffin, (f) absorption accelerators, such as, for example, quaternary ammonium compounds, (g) wetting agents, such as, for example, cetyl alcohol, and glycerol monostearate, magnesium stearate and the like, (h) adsorbents, such as, for example, kaolin and bentonite, and (i) lubricants, such as, for example, talc, calcium stearate, magnesium stearate, solid polyethylene glycols, sodium lauryl sulfate, or mixtures thereof. In the case of capsules, tablets, and pills, the dosage forms may also comprise buffering agents. In some embodiments, the excipient is not water. In some embodiments, the excipient is not a solvent (e.g., EtOH, diethyl ether, ethyl acetate, or hydrocarbon-based solvents (e.g., hexanes). In some embodiments, the dosage form is substantially free of water and/or solvents, for example less than about 5% water by mass, less than 2% water by mass, less than 1% water by mass, less than 0.5% water by mass, or less than 0.1% water by mass.

Excipients or pharmaceutically acceptable adjuvants known in the pharmaceutical formulation art may also be used in the pharmaceutical compositions of the disclosure. These include, but are not limited to, preserving, wetting, suspending, sweetening, flavoring, perfuming, emulsifying, and dispensing agents. Prevention of the action of microorganisms may be ensured by inclusion of various antibacterial and antifungal agents, for example, parabens, chlorobutanol, phenol, sorbic acid, and the like. It may also be desirable to include isotonic agents, for example, sugars, sodium chloride, and the like. If desired, a pharmaceutical composition of the disclosure may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Solid dosage forms as described above may be prepared with coatings and shells, such as enteric coatings and others well known in the art. They may contain pacifying agents and can also be of such composition that they release the active compound or compounds in a certain part of the intestinal tract in a delayed manner. Non-limiting examples of embedded compositions that may be used are polymeric substances and waxes. The active compounds may also be in microencapsulated form, if appropriate, with one or more of the above-mentioned excipients.

Suspensions, in addition to the active compounds, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Solid dosage forms for oral administration, which includes capsules, tablets, pills, powders, and granules, may be used. In such solid dosage forms, the active compound may be mixed with at least one inert, pharmaceutically acceptable excipient (also known as a pharmaceutically acceptable carrier).

Administration of 5-Cl-NiPT iodide, crystalline 5-Cl-NiPT iodide, 5-MeO-NiPT iodide, crystalline 5-MeO-NiPT iodide, 5-Me-NiPT iodide, crystalline 5-Me-NiPT iodide, 2-Me-NiPT iodide, crystalline 2-Me-NiPT iodide, 7-Me-NiPT iodide, crystalline 7-Me-NiPT iodide, 5-F-NiPT iodide, crystalline 5-F-NiPT iodide, specific crystalline forms thereof, such as crystalline form 1 of 5-Cl-NiPT iodide, crystalline form 1 of 5-MeO-NiPT iodide, crystalline form 1 of 5-Me-NiPT iodide, crystalline form 1 of 2-Me-NiPT iodide, crystalline form 1 of 7-Me-NiPT iodide, or crystalline form 1 of 5-F-NiPT iodide, or a compound of formula (I) or formula (III) of this disclosure in pure form or in an appropriate pharmaceutical composition may be carried out via any of the accepted modes of administration or agents for serving similar utilities. Thus, administration may be, for example, orally, buccally, nasally, parenterally (intravenous, intramuscular, or subcutaneous), topically, transdermally, intravaginally, intravesically, or intrasystemically, in the form of solid, semi-solid, lyophilized powder, or liquid dosage forms, such as, for example, tablets, suppositories, pills, soft elastic and hard gelatin capsules, powders, solutions, suspensions, or aerosols, or the like, such as, for example, in unit dosage forms suitable for simple administration of precise dosages. One route of administration may be oral administration, using a convenient daily dosage regimen that can be adjusted according to the degree of severity of the disease-state to be treated.

Exemplary Embodiments of the Invention

E1. [2-(5-chloro-1H-indol-3-yl)ethyl](propan-2-yl)azanium iodide (5-chloro-N-isopropyltryptammonium iodide).

E2. Crystalline [2-(5-chloro-1H-indol-3-yl)ethyl](propan-2-yl)azanium iodide (5-chloro-N-isopropyltryptammonium iodide).

E3. Crystalline form 1 of [2-(5-chloro-1H-indol-3-yl)ethyl](propan-2-yl)azanium iodide (5-chloro-N-isopropyltryptammonium iodide).

E4. Crystalline form 1 of 5-chloro-N-isopropyltryptammonium iodide according to E3, characterized by at least one of:
 an orthorhombic crystal system at a temperature of about 297 K;
 a $P2_12_12_1$ space group at a temperature of about 297 K;
 unit cell dimensions a=5.9905(3) Å, b=11.2975(5) Å, c=22.7295(12) Å, α=90°, β=90°, and γ=90°;
 an X-ray powder diffraction pattern substantially similar to FIG. 13; or
 an X-ray powder diffraction pattern characterized by at least two peaks selected from 8.7, 18.9, and 20.5° 2θ±0.2° 2θ.

E5. A composition comprising 5-chloro-N-isopropyltryptammonium iodide according to E1 and an excipient.

E6. A composition comprising crystalline 5-chloro-N-isopropyltryptammonium iodide according to any one of E2-E4 and an excipient.

E7. A composition comprising 5-chloro-N-isopropyltryptammonium iodide according to E1 as a first component and a second component selected from at least one of (a) a serotonergic drug, (b) a purified psilocybin derivative, (c) a purified cannabinoid, (d) a purified terpene, (e) an adrenergic drug, (f) a dopaminergic drug, (g) a monoamine oxidase inhibitor, (h) a purified erinacine, and (i) a purified hericenone.

E8. A composition comprising crystalline 5-chloro-N-isopropyltryptammonium iodide according to any one of E2-E4 as a first component and a second component selected from at least one of (a) a serotonergic drug, (b) a purified psilocybin derivative, (c) a purified cannabinoid, (d) a purified terpene, (e) an adrenergic drug, (f) a dopaminergic drug, (g) a monoamine oxidase inhibitor, (h) a purified erinacine, and (i) a purified hericenone.

E9. A method of preventing or treating a psychological disorder comprising the step of:
 administering to a subject in need thereof a therapeutically effective amount of 5-chloro-N-isopropyltryptammonium iodide according to E1.

E10. A method of preventing or treating a psychological disorder comprising the step of:
 administering to a subject in need thereof a therapeutically effective amount of crystalline 5-chloro-N-isopropyltryptammonium iodide according to any one of E2-E4.

E11. A method of preventing or treating a psychological disorder comprising the step of:
 administering to a subject in need thereof a composition according to E5 or E7.

E12. A method of preventing or treating a psychological disorder comprising the step of:
 administering to a subject in need thereof a composition according to E6 or E8.

E13. A method of preventing or treating inflammation and/or pain comprising the step of:
 administering to a subject in need thereof a therapeutically effective amount of 5-chloro-N-isopropyltryptammonium iodide according to E1.

E14. A method of preventing or treating inflammation and/or pain comprising the step of:
 administering to a subject in need thereof a therapeutically effective amount of crystalline 5-chloro-N-isopropyltryptammonium iodide according to any one of E2-E4.

E15. A method of preventing or treating inflammation and/or pain comprising the step of:
 administering to a subject in need thereof a composition according to E5 or E7.

E16. A method of preventing or treating inflammation and/or pain comprising the step of:
 administering to a subject in need thereof a composition according to E6 or E8.

E17. [2-(5-methoxy-1H-indol-3-yl)ethyl](propan-2-yl)azanium iodide (5-methoxy-N-isopropyltryptammonium iodide).

E18. Crystalline [2-(5-methoxy-1H-indol-3-yl)ethyl](propan-2-yl)azanium iodide (5-methoxy-N-isopropyltryptammonium iodide).

E19. Crystalline form 1 of [2-(5-methoxy-1H-indol-3-yl)ethyl](propan-2-yl)azanium iodide (5-methoxy-N-isopropyltryptammonium iodide).

E20. Crystalline form 1 of 5-methoxy-N-isopropyltryptammonium iodide according to E19, characterized by at least one of:
- an orthorhombic crystal system at a temperature of about 300 K;
- a $P2_12_12_1$ space group at a temperature of about 300 K;
- unit cell dimensions a=5.9940(5) Å, b=11.2071(9) Å, c=23.736(2) Å, α=90°, β=90°, and γ=90°;
- an X-ray powder diffraction pattern substantially similar to FIG. 14; or
- an X-ray powder diffraction pattern characterized by at least two peaks selected from 7.4, 8.7, 10.8, and 13.7° 2θ±0.2° 2θ.

E21. A composition comprising 5-methoxy-N-isopropyltryptammonium iodide according to E17 and an excipient.

E22. A composition comprising crystalline 5-methoxy-N-isopropyltryptammonium iodide according to any one of E18-E20 and an excipient.

E23. A composition comprising 5-methoxy-N-isopropyltryptammonium iodide according to E17 as a first component and a second component selected from at least one of (a) a serotonergic drug, (b) a purified psilocybin derivative, (c) a purified cannabinoid, (d) a purified terpene, (e) an adrenergic drug, (f) a dopaminergic drug, (g) a monoamine oxidase inhibitor, (h) a purified erinacine, and (i) a purified hericenone.

E24. A composition comprising crystalline 5-methoxy-N-isopropyltryptammonium iodide according to any one of E18-E20 as a first component and a second component selected from at least one of (a) a serotonergic drug, (b) a purified psilocybin derivative, (c) a purified cannabinoid, (d) a purified terpene, (e) an adrenergic drug, (f) a dopaminergic drug, (g) a monoamine oxidase inhibitor, (h) a purified erinacine, and (i) a purified hericenone.

E25. A method of preventing or treating a psychological disorder comprising the step of:
administering to a subject in need thereof a therapeutically effective amount of 5-methoxy-N-isopropyltryptammonium iodide according to E17.

E26. A method of preventing or treating a psychological disorder comprising the step of:
administering to a subject in need thereof a therapeutically effective amount of crystalline 5-methoxy-N-isopropyltryptammonium iodide according to any one of E18-E20.

E27. A method of preventing or treating a psychological disorder comprising the step of:
administering to a subject in need thereof a composition according to E21 or E23.

E28. A method of preventing or treating a psychological disorder comprising the step of:
administering to a subject in need thereof a composition according to E22 or E24.

E29. A method of preventing or treating inflammation and/or pain comprising the step of:
administering to a subject in need thereof a therapeutically effective amount of 5-methoxy-N-isopropyltryptammonium iodide according to E17.

E30. A method of preventing or treating inflammation and/or pain comprising the step of:
administering to a subject in need thereof a therapeutically effective amount of crystalline 5-methoxy-N-isopropyltryptammonium iodide according to any one of E18-E20.

E31. A method of preventing or treating inflammation and/or pain comprising the step of:
administering to a subject in need thereof a composition according to E21 or E23.

E32. A method of preventing or treating inflammation and/or pain comprising the step of:
administering to a subject in need thereof a composition according to E22 or E24.

E33. [2-(5-methyl-1H-indol-3-yl)ethyl](propan-2-yl)azanium iodide (5-methyl-N-isopropyltryptammonium iodide).

E34. Crystalline [2-(5-methyl-1H-indol-3-yl)ethyl](propan-2-yl)azanium iodide (5-methyl-N-isopropyltryptammonium iodide).

E35. Crystalline form 1 of [2-(5-methyl-1H-indol-3-yl)ethyl](propan-2-yl)azanium iodide (5-methyl-N-isopropyltryptammonium iodide).

E36. Crystalline form 1 of 5-methyl-N-isopropyltryptammonium iodide according to E35, characterized by at least one of:
- an orthorhombic crystal system at a temperature of about 297 K;
- a $P2_12_12_1$ space group at a temperature of about 297 K;
- unit cell dimensions a=6.0607(3) Å, b=11.2510(6) Å, c=22.8679(14) Å, α=90°, β=90°, and γ=90°;
- an X-ray powder diffraction pattern substantially similar to FIG. 15; or
- an X-ray powder diffraction pattern characterized by at least two peaks selected from 7.7, 8.8, and 20.3° 2θ±0.2° 2θ.

E37. A composition comprising 5-methyl-N-isopropyltryptammonium iodide according to E33 and an excipient.

E38. A composition comprising crystalline 5-methyl-N-isopropyltryptammonium iodide according to any one of E34-E36 and an excipient.

E39. A composition comprising 5-methyl-N-isopropyltryptammonium iodide according to E33 as a first component and a second component selected from at least one of (a) a serotonergic drug, (b) a purified psilocybin derivative, (c) a purified cannabinoid, (d) a purified terpene, (e) an adrenergic drug, (f) a dopaminergic drug, (g) a monoamine oxidase inhibitor, (h) a purified erinacine, and (i) a purified hericenone.

E40. A composition comprising crystalline 5-methyl-N-isopropyltryptammonium iodide according to any one of E34-E36 as a first component and a second component selected from at least one of (a) a serotonergic drug, (b) a purified psilocybin derivative, (c) a purified cannabinoid, (d) a purified terpene, (e) an adrenergic drug, (f) a dopaminergic drug, (g) a monoamine oxidase inhibitor, (h) a purified erinacine, and (i) a purified hericenone.

E41. A method of preventing or treating a psychological disorder comprising the step of:
administering to a subject in need thereof a therapeutically effective amount of 5-methyl-N-isopropyltryptammonium iodide according to E33.

E42. A method of preventing or treating a psychological disorder comprising the step of:
administering to a subject in need thereof a therapeutically effective amount of crystalline 5-methyl-N-isopropyltryptammonium iodide according to any one of E34-E36.

E43. A method of preventing or treating a psychological disorder comprising the step of:

administering to a subject in need thereof a composition according to E37 or E39.

E44. A method of preventing or treating a psychological disorder comprising the step of:
administering to a subject in need thereof a composition according to E38 or E40.

E45. A method of preventing or treating inflammation and/or pain comprising the step of:
administering to a subject in need thereof a therapeutically effective amount of 5-methyl-N-isopropyltryptammonium iodide according to E33.

E46. A method of preventing or treating inflammation and/or pain comprising the step of:
administering to a subject in need thereof a therapeutically effective amount of crystalline 5-methyl-N-isopropyltryptammonium iodide according to any one of E34-E36.

E47. A method of preventing or treating inflammation and/or pain comprising the step of:
administering to a subject in need thereof a composition according to E37 or E39.

E48. A method of preventing or treating inflammation and/or pain comprising the step of:
administering to a subject in need thereof a composition according to E38 or E40.

E49. [2-(2-methyl-1H-indol-3-yl)ethyl](propan-2-yl)azanium iodide (2-methyl-N-isopropyltryptammonium iodide).

E50. Crystalline [2-(2-methyl-1H-indol-3-yl)ethyl](propan-2-yl)azanium iodide (2-methyl-N-isopropyltryptammonium iodide).

E51. Crystalline form 1 of [2-(2-methyl-1H-indol-3-yl)ethyl](propan-2-yl)azanium iodide (2-methyl-N-isopropyltryptammonium iodide).

E52. Crystalline form 1 of 2-methyl-N-isopropyltryptammonium iodide according to E51, characterized by at least one of:
an orthorhombic crystal system at a temperature of about 273 K;
a $P2_12_12_1$ space group at a temperature of about 273 K;
unit cell dimensions a=7.5933(5) Å, b=10.7783(5) Å, c=19.1520(12) Å, α=90°, β=90°, and γ=90°;
an X-ray powder diffraction pattern substantially similar to FIG. 16; or
an X-ray powder diffraction pattern characterized by at least two peaks selected from 9.2, 16.4, and 18.1° 2θ±0.2° 2θ.

E53. A composition comprising 2-methyl-N-isopropyltryptammonium iodide according to E49 and an excipient.

E54. A composition comprising crystalline 2-methyl-N-isopropyltryptammonium iodide according to any one of E50-E52 and an excipient.

E55. A composition comprising 2-methyl-N-isopropyltryptammonium iodide according to E49 as a first component and a second component selected from at least one of (a) a serotonergic drug, (b) a purified psilocybin derivative, (c) a purified cannabinoid, (d) a purified terpene, (e) an adrenergic drug, (f) a dopaminergic drug, (g) a monoamine oxidase inhibitor, (h) a purified erinacine, and (i) a purified hericenone.

E56. A composition comprising crystalline 2-methyl-N-isopropyltryptammonium iodide according to any one of E50-E52 as a first component and a second component selected from at least one of (a) a serotonergic drug, (b) a purified psilocybin derivative, (c) a purified cannabinoid, (d) a purified terpene, (e) an adrenergic drug, (f) a dopaminergic drug, (g) a monoamine oxidase inhibitor, (h) a purified erinacine, and (i) a purified hericenone.

E57. A method of preventing or treating a psychological disorder comprising the step of:
administering to a subject in need thereof a therapeutically effective amount of 2-methyl-N-isopropyltryptammonium iodide according to E49.

E58. A method of preventing or treating a psychological disorder comprising the step of:
administering to a subject in need thereof a therapeutically effective amount of crystalline 2-methyl-N-isopropyltryptammonium iodide according to any one of E50-E52.

E59. A method of preventing or treating a psychological disorder comprising the step of:
administering to a subject in need thereof a composition according to E53 or E55.

E60. A method of preventing or treating a psychological disorder comprising the step of:
administering to a subject in need thereof a composition according to E54 or E56.

E61. A method of preventing or treating inflammation and/or pain comprising the step of:
administering to a subject in need thereof a therapeutically effective amount of 2-methyl-N-isopropyltryptammonium iodide according to E49.

E62. A method of preventing or treating inflammation and/or pain comprising the step of:
administering to a subject in need thereof a therapeutically effective amount of crystalline 2-methyl-N-isopropyltryptammonium iodide according to any one of E50-E52.

E63. A method of preventing or treating inflammation and/or pain comprising the step of:
administering to a subject in need thereof a composition according to E53 or E55.

E64. A method of preventing or treating inflammation and/or pain comprising the step of:
administering to a subject in need thereof a composition according to E54 or E56.

E65. [2-(7-methyl-1H-indol-3-yl)ethyl](propan-2-yl)azanium iodide (7-methyl-N-isopropyltryptammonium iodide).

E66. Crystalline [2-(7-methyl-1H-indol-3-yl)ethyl](propan-2-yl)azanium iodide (7-methyl-N-isopropyltryptammonium iodide).

E67. Crystalline form 1 of [2-(7-methyl-1H-indol-3-yl)ethyl](propan-2-yl)azanium iodide (7-methyl-N-isopropyltryptammonium iodide).

E68. Crystalline form 1 of 7-methyl-N-isopropyltryptammonium iodide according to E67, characterized by at least one of:
a monoclinic crystal system at a temperature of about 300 K;
a P21/n space group at a temperature of about 300 K;
unit cell dimensions a=13.3208(11) Å, b=8.6748(5) Å, c=15.0094(12) Å, α=90°, β=115.070(3°), and γ=90°;
an X-ray powder diffraction pattern substantially similar to FIG. 17; or
an X-ray powder diffraction pattern characterized by at least two peaks selected from 7.4, 14.9, and 16.8 2θ±0.2° 2θ.

E69. A composition comprising 7-methyl-N-isopropyltryptammonium iodide according to E65 and an excipient.

E70. A composition comprising crystalline 7-methyl-N-isopropyltryptammonium iodide according to any one of E66-E68 and an excipient.

E71. A composition comprising 7-methyl-N-isopropyltryptammonium iodide according to E65 as a first component and a second component selected from at least one of (a) a serotonergic drug, (b) a purified psilocybin derivative, (c) a purified cannabinoid, (d) a purified terpene, (e) an adrenergic drug, (f) a dopaminergic drug, (g) a monoamine oxidase inhibitor, (h) a purified erinacine, and (i) a purified hericenone.

E72. A composition comprising crystalline 7-methyl-N-isopropyltryptammonium iodide according to any one of E66-E68 as a first component and a second component selected from at least one of (a) a serotonergic drug, (b) a purified psilocybin derivative, (c) a purified cannabinoid, (d) a purified terpene, (e) an adrenergic drug, (f) a dopaminergic drug, (g) a monoamine oxidase inhibitor, (h) a purified erinacine, and (i) a purified hericenone.

E73. A method of preventing or treating a psychological disorder comprising the step of:
administering to a subject in need thereof a therapeutically effective amount of 7-methyl-N-isopropyltryptammonium iodide according to E65.

E74. A method of preventing or treating a psychological disorder comprising the step of:
administering to a subject in need thereof a therapeutically effective amount of crystalline 7-methyl-N-isopropyltryptammonium iodide according to any one of E66-E68.

E75. A method of preventing or treating a psychological disorder comprising the step of:
administering to a subject in need thereof a composition according to E69 or E71.

E76. A method of preventing or treating a psychological disorder comprising the step of:
administering to a subject in need thereof a composition according to E70 or E72.

E77. A method of preventing or treating inflammation and/or pain comprising the step of:
administering to a subject in need thereof a therapeutically effective amount of 7-methyl-N-isopropyltryptammonium iodide according to E65.

E78. A method of preventing or treating inflammation and/or pain comprising the step of:
administering to a subject in need thereof a therapeutically effective amount of crystalline 7-methyl-N-isopropyltryptammonium iodide according to any one of E66-E68.

E79. A method of preventing or treating inflammation and/or pain comprising the step of:
administering to a subject in need thereof a composition according to E69 or E71.

E80. A method of preventing or treating inflammation and/or pain comprising the step of:
administering to a subject in need thereof a composition according to E70 or E72.

E81. [2-(5-fluoro-1H-indol-3-yl)ethyl](propan-2-yl)azanium iodide (5-fluoro-N-isopropyltryptammonium iodide).

E82. Crystalline [2-(5-fluoro-1H-indol-3-yl)ethyl](propan-2-yl)azanium iodide (5-fluoro-N-isopropyltryptammonium iodide).

E83. Crystalline form 1 of [2-(5-fluoro-1H-indol-3-yl)ethyl](propan-2-yl)azanium iodide (5-fluoro-N-isopropyltryptammonium iodide).

E84. Crystalline form 1 of 5-fluoro-N-isopropyltryptammonium iodide according to E83, characterized by at least one of:
an orthorhombic crystal system at a temperature of about 300 K;
a $P2_12_12_1$ space group at a temperature of about 300 K;
unit cell dimensions a=5.9493(4) Å, b=11.4462(5) Å, c=21.7601(12) Å, α=90, β=90°, and γ=90°;
an X-ray powder diffraction pattern substantially similar to FIG. 18; or
an X-ray powder diffraction pattern characterized by at least two peaks selected from 8.1, 19.3, and 20.8° 2θ±0.2° 2θ.

E85. A composition comprising 5-fluoro-N-isopropyltryptammonium iodide according to E81 and an excipient.

E86. A composition comprising crystalline 5-fluoro-N-isopropyltryptammonium iodide according to any one of E82-E84 and an excipient.

E87. A composition comprising 5-fluoro-N-isopropyltryptammonium iodide according to E81 as a first component and a second component selected from at least one of (a) a serotonergic drug, (b) a purified psilocybin derivative, (c) a purified cannabinoid, (d) a purified terpene, (e) an adrenergic drug, (f) a dopaminergic drug, (g) a monoamine oxidase inhibitor, (h) a purified erinacine, and (i) a purified hericenone.

E88. A composition comprising crystalline 5-fluoro-N-isopropyltryptammonium iodide according to any one of E82-E84 as a first component and a second component selected from at least one of (a) a serotonergic drug, (b) a purified psilocybin derivative, (c) a purified cannabinoid, (d) a purified terpene, (e) an adrenergic drug, (f) a dopaminergic drug, (g) a monoamine oxidase inhibitor, (h) a purified erinacine, and (i) a purified hericenone.

E89. A method of preventing or treating a psychological disorder comprising the step of:
administering to a subject in need thereof a therapeutically effective amount of 5-fluoro-N-isopropyltryptammonium iodide according to E81.

E90. A method of preventing or treating a psychological disorder comprising the step of:
administering to a subject in need thereof a therapeutically effective amount of crystalline 5-fluoro-N-isopropyltryptammonium iodide according to any one of E82-E84.

E91. A method of preventing or treating a psychological disorder comprising the step of:
administering to a subject in need thereof a composition according to E85 or E87.

E92. A method of preventing or treating a psychological disorder comprising the step of:
administering to a subject in need thereof a composition according to E86 or E88.

E93. A method of preventing or treating inflammation and/or pain comprising the step of:
administering to a subject in need thereof a therapeutically effective amount of 5-fluoro-N-isopropyltryptammonium iodide according to E81.

E94. A method of preventing or treating inflammation and/or pain comprising the step of:
administering to a subject in need thereof a therapeutically effective amount of crystalline 5-fluoro-N-isopropyltryptammonium iodide according to any one of E82-E84.

E95. A method of preventing or treating inflammation and/or pain comprising the step of:
administering to a subject in need thereof a composition according to E85 or E87.

E96. A method of preventing or treating inflammation and/or pain comprising the step of:
administering to a subject in need thereof a composition according to E86 or E88.

E97. A method of making a mono alkyl tryptamine, comprising the step of:

reacting a substituted or unsubstituted tryptamine with an excess of a secondary alkyl halide and refluxing the solution for 12-24 hours.

E98. A method of making a mono alkyl tryptamine compound of formula (I)

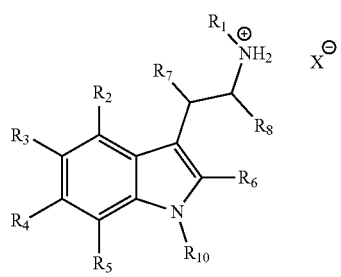

(I)

wherein:
- $R_1$ is a secondary alkyl;
- $R_2$, $R_3$, $R_4$, $R_5$, $R_6$, $R_7$, $R_8$, and $R_{10}$ are independently selected from hydrogen, optionally substituted $C_1$-$C_6$ alkyl, optionally substituted $C_2$-$C_6$ alkenyl, optionally substituted $C_1$-$C_6$ heteroalkyl, optionally substituted heteroaryl, optionally substituted aryl, halogen, hydroxy, —$OR_9$, —$OC(O)R_9$, —$OC(O)OR_9$, and —$OSO_2R_9$;
- $R_9$ is independently selected from hydrogen, optionally substituted $C_1$-$C_6$ alkyl, optionally substituted $C_1$-$C_6$ alkenyl, and optionally substituted aryl; and
- $X^-$ is a pharmaceutically acceptable halide anion;

comprising the step of:
reacting a substituted or unsubstituted tryptamine of formula (II)

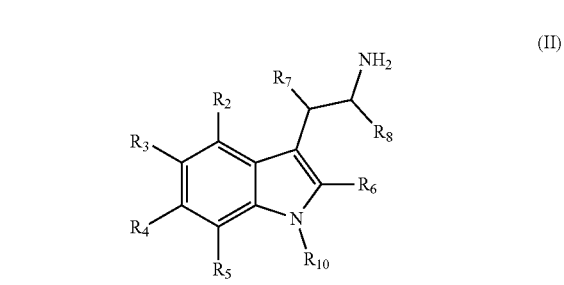

(II)

with an excess of a secondary alkyl halide, $R_1X$, and refluxing the solution for 12-24 hours;
wherein:
- $R_1$ and X of the secondary alkyl halide are identical to how $R_1$ and X are defined in formula (I); and
- $R_2$, $R_3$, $R_4$, $R_5$, $R_6$, $R_7$, $R_8$, and $R_{10}$ in formula (II) are identical to how $R_2$, $R_3$, $R_4$, $R_5$, $R_6$, $R_7$, $R_8$, and $R_{10}$ are defined in formula (I).

E99. The method of E98, wherein the halide, X, is selected from the group consisting of chloride (Cl⁻), bromide (Br⁻), and iodide (I⁻).

E100. The method of any one of E97-E99, wherein the secondary alkyl halide is an isopropyl halide.

E101. The method of any one of E97-E100, wherein the secondary alkyl halide is an isopropyl iodide.

E102. The method of any of E97-E101, wherein the compound of formula (I) is a substituted or unsubstituted N-isopropyl tryptamine.

E103. The method of any one of E97-E102, wherein the monoalkyl tryptamine or the compound of formula (I) is 5-methoxy-N-isopropyltryptammonium iodide.

E104. The method of any one of E97-E102, wherein the monoalkyl tryptamine or the compound of formula (I) is 5-methyl-N-isopropyltryptammonium iodide.

E105. The method of any one of E97-E102, wherein the monoalkyl tryptamine or the compound of formula (I) is 2-methyl-N-isopropyltryptammonium iodide.

E106. The method of any one of E97-E102, wherein the monoalkyl tryptamine or the compound of formula (I) is 7-methyl-N-isopropyltryptammonium iodide.

E107. The method of any one of E97-E102, wherein the monoalkyl tryptamine or the compound of formula (I) is 5-fluoro-N-isopropyltryptammonium iodide.

E108. A method of making a dialkyl tryptamine, comprising the step of:
reacting a substituted or unsubstituted tryptamine with an excess of a secondary alkyl halide and refluxing the solution for 36-72 hours.

E109. A method of making a dialkyl tryptamine compound of formula (III)

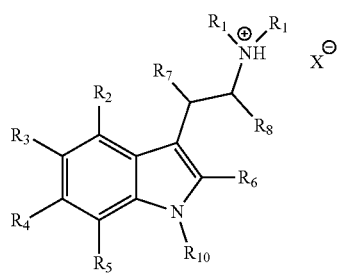

(III)

wherein:
- $R_1$ is for each occurrence a secondary alkyl;
- $R_2$, $R_3$, $R_4$, $R_5$, $R_6$, $R_7$, $R_8$, and $R_{10}$ are independently selected from hydrogen, optionally substituted $C_1$-$C_6$ alkyl, optionally substituted $C_2$-$C_6$ alkenyl, optionally substituted $C_1$-$C_6$ heteroalkyl, optionally substituted heteroaryl, optionally substituted aryl, halogen, hydroxy, —$OR_9$, —$OC(O)R_9$, —$OC(O)OR_9$, and —$OSO_2R_9$;
- $R_9$ is independently selected from hydrogen, optionally substituted $C_1$-$C_6$ alkyl, optionally substituted $C_2$-$C_6$ alkenyl, and optionally substituted aryl; and
- $X^-$ is a pharmaceutically acceptable halide anion;

comprising the step of:
reacting a substituted or unsubstituted tryptamine of formula (IV)

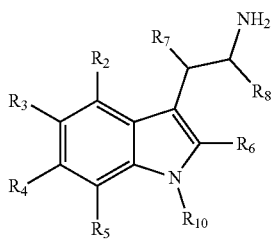

(IV)

with an excess of a secondary alkyl halide, R₁X, and refluxing the solution for 36-72 hours;
wherein:
R₁ and X of the secondary alkyl halide are identical to how $R_1$ and X are defined in formula (III); and
$R_2, R_3, R_4, R_5, R_6, R_7, R_8$, and $R_{10}$ in formula (IV) are identical to how $R_2, R_3, R_4, R_5, R_6, R_7, R_8$, and $R_{10}$ are defined in formula (III).

E110. The method of E109, wherein the halide, X, is selected from the group consisting of chloride (Cl⁻), bromide (Br⁻), and iodide (I⁻).

E111. The method of any one of E108-E110, wherein the secondary alkyl halide is an isopropyl halide.

E112. The method of any one of E108-E111, wherein the secondary alkyl halide is an isopropyl iodide.

E113. The method of any one of E108-E112, wherein the dialkyl tryptamine or the compound of formula (III) is a substituted or unsubstituted N,N-di-n-isopropyl tryptamine.

E114. A mono alkyl tryptamine compound of formula (I):

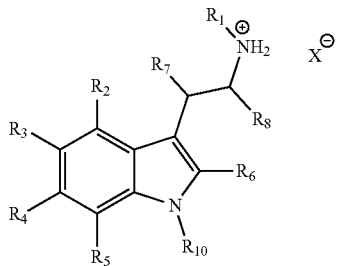

(I)

wherein:
$R_1$ is a secondary alkyl;
$R_2, R_3, R_4, R_5, R_6, R_7, R_8$, and $R_{10}$ are independently selected from hydrogen, optionally substituted $C_1$-$C_6$ alkyl, optionally substituted $C_2$-$C_6$ alkenyl, optionally substituted $C_1$-$C_6$ heteroalkyl, optionally substituted heteroaryl, optionally substituted aryl, halogen, hydroxy, —OR₉, —OC(O)R₉, —OC(O)OR₉, and —OSO₂R₉;
$R_9$ is independently selected from hydrogen, optionally substituted $C_1$-$C_6$ alkyl, optionally substituted $C_1$-$C_6$ alkenyl, and optionally substituted aryl; and
X⁻ is a pharmaceutically acceptable halide anion.

E115. The mono alkyl tryptamine compound of E114, wherein $R_1$ is isopropyl.

E116. The mono alkyl tryptamine compound of E114 or E115, wherein the compound of formula (I) is 5-chloro-N-isopropyltryptammonium iodide.

E117. The mono alkyl tryptamine compound of E114 or E115, wherein the compound of formula (I) is 5-methoxy-N-isopropyltryptammonium iodide.

E118. The mono alkyl tryptamine compound of E114 or E115, wherein the compound of formula (I) is 5-methyl-N-isopropyltryptammonium iodide.

E119. The mono alkyl tryptamine compound of E114 or E115, wherein the compound of formula (I) is 2-methyl-N-isopropyltryptammonium iodide.

E120. The mono alkyl tryptamine compound of E114 or E115, wherein the compound of formula (I) is 7-methyl-N-isopropyltryptammonium iodide.

E121. The mono alkyl tryptamine compound of E114 or E115, wherein the compound of formula (I) is 5-fluoro-N-isopropyltryptammonium iodide.

E122. The mono alkyl tryptamine compound of E114 or E115, wherein the compound of formula (I) is 5-bromo-N-isopropyltryptammonium iodide.

E123. The mono alkyl tryptamine compound of E114 or E115, wherein the compound of formula (I) is 6-fluoro-N-isopropyltryptammonium iodide.

E124. A dialkyl tryptamine compound of formula (III):

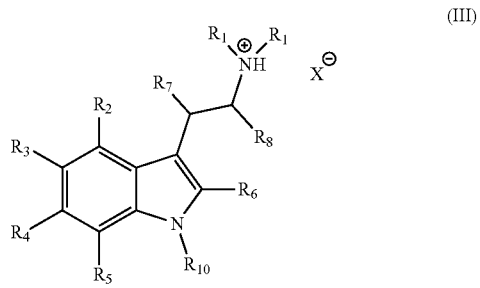

(III)

wherein:
$R_1$ is for each occurrence a secondary alkyl;
$R_2, R_3, R_4, R_5, R_6, R_7, R_8$, and $R_{10}$ are independently selected from hydrogen, optionally substituted $C_1$-$C_6$ alkyl, optionally substituted $C_2$-$C_6$ alkenyl, optionally substituted $C_1$-$C_6$ heteroalkyl, optionally substituted heteroaryl, optionally substituted aryl, halogen, hydroxy, —OR₉, —OC(O)R₉, —OC(O)OR₉, and —OSO₂R₉;
$R_9$ is independently selected from hydrogen, optionally substituted $C_1$-$C_6$ alkyl, optionally substituted $C_2$-$C_6$ alkenyl, and optionally substituted aryl; and
X⁻ is a pharmaceutically acceptable halide anion.

E125. The dialkyl tryptamine compound of E124, wherein $R_1$ is isopropyl.

E126. A composition comprising the mono alkyl tryptamine compound according to any one of E114-E123 and an excipient.

E127. A composition comprising the dialkyl tryptamine compound according to E124 or E125 and an excipient.

E128. A composition comprising the mono alkyl tryptamine compound according to any one of E114-E123 as a first component and a second component selected from at least one of (a) a serotonergic drug, (b) a purified psilocybin derivative, (c) a purified cannabinoid, (d) a purified terpene, (e) an adrenergic drug, (f) a dopaminergic drug, (g) a monoamine oxidase inhibitor, (h) a purified erinacine, and (i) a purified hericenone.

E129. A composition comprising the dialkyl tryptamine compound according to E124 or E125 as a first component and a second component selected from at least one of (a) a serotonergic drug, (b) a purified psilocybin derivative, (c) a purified cannabinoid, (d) a purified terpene, (e) an adrenergic drug, (f) a dopaminergic drug, (g) a monoamine oxidase inhibitor, (h) a purified erinacine, and (i) a purified hericenone.

E130. A method of preventing or treating a psychological disorder comprising the step of:
administering to a subject in need thereof a therapeutically effective amount of the mono alkyl tryptamine compound according to any one of E114-E123.

E131. A method of preventing or treating a psychological disorder comprising the step of:
administering to a subject in need thereof a therapeutically effective amount of the dialkyl tryptamine compound according to E124 or E125.

E132. A method of preventing or treating a psychological disorder comprising the step of:
  administering to a subject in need thereof a composition according to E126 or E128.

E133. A method of preventing or treating a psychological disorder comprising the step of:
  administering to a subject in need thereof a composition according to E127 or E129.

E134. A method of preventing or treating inflammation and/or pain comprising the step of:
  administering to a subject in need thereof a therapeutically effective amount of the mono alkyl tryptamine compound according to any one of E114-E123.

E135. A method of preventing or treating inflammation and/or pain comprising the step of:
  administering to a subject in need thereof a therapeutically effective amount of the dialkyl tryptamine compound according to E124 or E125.

E136. A method of preventing or treating inflammation and/or pain comprising the step of:
  administering to a subject in need thereof a composition according to E126 or E128.

E137. A method of preventing or treating inflammation and/or pain comprising the step of:
  administering to a subject in need thereof a composition according to E127 or E129.

EXAMPLES

The preparation and characterization of each of crystalline form 1 of [2-(5-chloro-1H-indol-3-yl)ethyl](propan-2-yl)azanium iodide (5-chloro-N-isopropyltryptammonium iodide or 5-Cl-NiPT iodide), crystalline form 1 of [2-(5-methoxy-1H-indol-3-yl)ethyl](propan-2-yl)azanium iodide (5-methoxy-N-isopropyltryptammonium iodide or 5-MeO-NiPT iodide), crystalline form 1 of [2-(5-methyl-1H-indol-3-yl)ethyl](propan-2-yl)azanium iodide (5-methyl-N-isopropyltryptammonium iodide or 5-Me-NiPT iodide), crystalline form 1 of [2-(2-methyl-1H-indol-3-yl)ethyl](propan-2-yl)azanium iodide (2-methyl-N-isopropyltryptammonium iodide or 2-Me-NiPT iodide), crystalline form 1 of [2-(7-methyl-1H-indol-3-yl)ethyl](propan-2-yl)azanium iodide (7-methyl-N-isopropyltryptammonium iodide or 7-Me-NiPT iodide), and crystalline form 1 of [2-(5-fluoro-1H-indol-3-yl)ethyl](propan-2-yl)azanium iodide (5-fluoro-N-isopropyltryptammonium iodide or 5-F-NiPT iodide) are described below.

The examples for crystalline form 1 of 5-Meo-NiPT iodide, crystalline form 1 of 5-Me-NiPT iodide, crystalline form 1 of 2-Me-NiPT iodide, crystalline form 1 of 7-Me-NiPT iodide, and crystalline form 1 of 5-F-NiPT iodide were prepared using the methods of this disclosure.

Single Crystal X-Ray Diffraction (SCXRD) Characterization: Data were collected on a Bruker D8 Venture CMOS Diffractometer equipped with an Oxford Cryosystems Cryostream cooling device and using Mo Kα radiation. Structures were solved using the Bruker SHELXTL program and refined with the SHELXTL program as part of the Bruker SHELXTL suite, or OLEX2 software. Unless otherwise stated, hydrogen atoms attached to carbon were placed geometrically and allowed to refine with a riding isotropic displacement parameter. Hydrogen atoms attached to a heteroatom were located in a difference Fourier synthesis and were allowed to refine freely with an isotropic displacement parameter.

Example 1: Preparation and Characterization of Crystalline Form 1 of 5-Cl-NiPT Iodide Synthesis
A round bottom flask was charged with 151 mg of 5-chloro-N-isopropyltryptamine hydrochloride, 207 mg of sodium carbonate, 0.913 mL of 2-iodopropane and 30 mL of methanol. The mixture was refluxed for 12 hours under an atmosphere of nitrogen. The remaining solid was filtered off and solvent was removed in vacuo to yield a yellow powder. The powder was dissolved in tetrahydrofuran, and the addition of dichloromethane resulted in the precipitation of a pure white powder.

Crystallization
Single crystals suitable for X-ray diffraction studies were grown from the slow evaporation of an ethanol/water solution.

Single Crystal Characterization
The single crystal data and structure refinement parameters for the crystalline form 1 structure of 5-Cl-NiPT iodide are reported in Table 3, below.

Example 2: Preparation and Characterization of Crystalline form 1 of 5-MeO-NiPT Iodide Synthesis
100 mg of 5-methoxytryptamine freebase, 0.735 mL of 2-iodopropane and 167 mg of sodium carbonate were mixed in 20 mL of isopropanol. The solution was refluxed for 16 hours. Solvent was removed in vacuo. After washing with diethyl ether, the resulting solid was recrystallized from ethanol.

Crystallization
Single crystals suitable for X-ray diffraction studies were grown from the slow evaporation of a methylene chloride solution.

Single Crystal Characterization
The single crystal data and structure refinement parameters for the crystalline form 1 structure of 5-MeO-NiPT iodide are reported in Table 3, below.

Example 3: Preparation and Characterization of Crystalline Form 1 of 5-Me-NiPT Iodide Synthesis
100 mg of 5-methyltryptamine freebase, 0.664 mL of 2-iodopropane and 151 mg of sodium carbonate were combined in 50 mL of isopropanol and refluxed for 16 hours. The solution was filtered and solvent was removed in vacuo to produce a solid residue.

Crystallization
Single crystals suitable for X-ray diffraction studies were grown from the slow evaporation of a methanol solution.

Single Crystal Characterization
The single crystal data and structure refinement parameters for the crystalline form 1 structure of 5-Me-NiPT iodide are reported in Table 3, below.

Example 4: Preparation and Characterization of Crystalline Form 1 of 2-Me-NiPT Iodide Synthesis
100 mg of 2-methyltryptamine freebase was mixed with 0.804 mL of 2-iodopropane and 183 mg of sodium carbonate in 20 mL of isopropanol. The solution was refluxed for 18 hours, and then solvent was removed in vacuo to yield a solid residue.

Crystallization
Single crystals suitable for X-ray diffraction studies were grown from the slow evaporation of a methanol solution.

Single Crystal Characterization

The single crystal data and structure refinement parameters for the crystalline form 1 structure of 2-Me-NiPT iodide are reported in Table 3, below.

Example 5: Preparation and Characterization of Crystalline Form 1 of 7-Me-NiPT Iodide Synthesis 100 mg of 7-methyltryptamine hydrochloride was mixed with 0.664 mL of 2-iodopropane and 151 mg of sodium carbonate in 20 mL of isopropanol. The solution was refluxed for 17 hours. The solution was filtered and solvent was removed in vacuo to yield a yellow residue.

Crystallization

Single crystals suitable for X-ray diffraction studies were grown from the slow evaporation of a methanol solution.

Single Crystal Characterization

The single crystal data and structure refinement parameters for the crystalline form 1 structure of 7-Me-NiPT iodide are reported in Table 3, below.

Example 6: Preparation and Characterization of Crystalline Form 1 of C—F-NiPT Iodide Synthesis 100 mg of 5-fluorotryptamine hydrochloride, 0.652 mL of 2-iodopropane and 148 mg of sodium carbonate were mixed together in 25 mL of isopropanol. The solution was heated at reflux for 17 hours. The resulting solution was filtered and solvent was removed in vacuo to yield a yellow powder.

Crystallization

Single crystals suitable for X-ray diffraction studies were grown from the slow evaporation of a methanol solution.

Single Crystal Characterization

The single crystal data and structure refinement parameters for the crystalline form 1 structure of 5-F-NiPT iodide are reported in Table 3, below.

TABLE 3

Single crystal data and structure refinement parameters

| Crystal data | Crystalline form 1 of 5-Cl-NiPT iodide | Crystalline form 1 of 5-MeO-NiPT iodide | Crystalline form 1 of 5-Me-NiPT iodide | Crystalline form 1 of 2-Me-NiPT iodide | Crystalline form 1 of 7-Me-NiPT iodide | Crystalline form of 1 5-F-NiPT iodide |
|---|---|---|---|---|---|---|
| Chemical formula | I·$C_{13}H_{18}ClN_2$ | I·$C_{14}H_{21}N_2O$ | I·$C_{14}H_{21}N_2$ | I·$C_{14}H_{21}N_2$ | I·$C_{14}H_{21}N_2$ | I·$C_{13}H_{18}FN_2$ |
| $M_r$ | 364.64 | 360.23 | 344.23 | 344.23 | 344.23 | 348.19 |
| Crystal system, space group | orthorhombic, $P2_12_12_1$ | orthorhombic, $P2_12_12_1$ | orthorhombic, $P2_12_12_1$ | orthorhombic, $P2_12_12_1$ | monoclinic, $P2_1/n$ | orthorhombic, $P2_12_12_1$ |
| Temperature (K.) | 297(2) | 300(2) | 297(2) | 273(2) | 300(2) | 300(2) |
| a, b, c (Å) | 5.9905(3), 11.2975(5), 22.7295(12) | 5.9940(5), 11.2071(9), 23.736(2) | 6.0607(3), 11.2510(6), 22.8679(14) | 7.5933(5), 10.7783(5), 19.1520(12) | 13.3208(11), 8.6748(5), 15.0094(12) | 5.9493(4), 11.4462(5), 21.7601(12) |
| α (°) | 90 | 90 | 90 | 90 | 90 | 90 |
| β (°) | 90 | 90 | 90 | 90 | 115.070(3) | 90 |
| γ (°) | 90 | 90 | 90 | 90 | 90 | 90 |
| V (Å$^3$) | 1538.28(13) | 1594.5(2) | 1559.34(15) | 1567.45(16) | 1571.0(2) | 1481.79(14) |
| Z | 4 | 4 | 4 | 4 | 4 | 4 |
| F(000) | 720 | 720 | 688 | 688 | 688 | 688 |
| $D_x$ (Mg m$^{-3}$) | 1.574 | 1.501 | 1.466 | 1.459 | 1.455 | 1.561 |
| Radiation type | Mo Kα | Mo Kα | Mo Kα | Mo Kα | Mo Kα | Mo Kα |
| λ (Å) | 0.71073 | 0.71073 | 0.71073 | 0.71073 | 0.71073 | 0.71073 |
| θ (°) | 2.54-26.40 | 3.15-26.37 | 2.54-26.41 | 2.89-25.37 | 2.69-26.39 | 3.33-26.34 |
| μ (mm$^{-1}$) | 2.238 | 2.001 | 2.038 | 2.027 | 2.022 | 2.155 |
| Crystal size (mm) | 0.24 × 0.22 × 0.2 | 0.21 × 0.2 × 0.19 | 0.33 × 0.06 × 0.06 | 0.4 × 0.2 × 0.05 | 0.25 × 0.19 × 0.09 | 0.28 × 0.05 × 0.05 |
| Crystal description | block | block | block | plate | block | block |
| Crystal color | colourless | colourless | colourless | colourless | colourless | colourless |
| Data collection | | | | | | |
| Diffractometer | Bruker APEX-II CCD | Bruker APEX-II CCD | Bruker APEX-II CCD | Bruker APEX-II CCD | Bruker APEX-II CCD | Bruker APEX-II CCD |
| Absorption correction | Multi-scan SADABS (Bruker, 2016) was used. wR2(int) was 0.0597 before and 0.0495 after correction. The Ratio of minimum to maximum transmission is 0.9192. The λ/2 | Multi-scan SADABS (Bruker, 2016) was used. wR2(int) was 0.0585 before and 0.0517 after correction. The Ratio of minimum to maximum transmission is 0.8811. The λ/2 | Multi-scan SADABS (Bruker, 2016) was used. wR2(int) was 0.0645 before and 0.0577 after correction. The Ratio of minimum to maximum transmission is 0.8967. The λ/2 | Multi-scan SADABS (Bruker, 2016) was used. wR2(int) was 0.0711 before and 0.0499 after correction. The Ratio of minimum to maximum transmission is 0.8355. The λ/2 | Multi-scan SADABS (Bruker, 2016) was used. wR2(int) was 0.0590 before and 0.0439 after correction. The Ratio of minimum to maximum transmission is 0.8774. The λ/2 | Multi-scan SADABS (Bruker, 2016) was used. wR2(int) was 0.0652 before and 0.0495 after correction. The Ratio of minimum to maximum transmission is 0.8680. The λ/2 |

TABLE 3-continued

Single crystal data and structure refinement parameters

| Crystal data | Crystalline form 1 of 5-Cl-NiPT iodide | Crystalline form 1 of 5-MeO-NiPT iodide | Crystalline form 1 of 5-Me-NiPT iodide | Crystalline form 1 of 2-Me-NiPT iodide | Crystalline form 1 of 7-Me-NiPT iodide | Crystalline form of 1 5-F-NiPT iodide |
|---|---|---|---|---|---|---|
| $T_{min}$, $T_{max}$ | correction factor is not present. 0.6852, 0.7454 | correction factor is not present. 0.6568, 0.7454 | correction factor is not present. 0.6684, 0.7454 | correction factor is not present. 0.6226, 0.7452 | correction factor is not present. 0.6540, 0.7454 | correction factor is not present. 0.6470, 0.7454 |
| No. of measured, independent, and observed [I > 2σ(I)] reflections | 46153, 3138, 3062 | 44446, 3277, 3158 | 41277, 3205, 3056 | 29283, 2857, 2757 | 46665, 3214, 2919 | 27893, 3040, 2825 |
| $R_{int}$ | 0.0228 | 0.0381 | 0.0301 | 0.0309 | 0.0259 | 0.0277 |
| $θ_{max}$, $θ_{min}$ (°) | 26.414, 2.542 | 26.419, 2.500 | 26.444, 3.228 | 25.401, 2.845 | 26.418, 2.690 | 26.379, 3.325 |
| h, k, l | −7 → 7, −14 → 14, −28 → 28 | −7 → 7, −14 → 14, −29 → 29 | −7 → 7, −14 → 14, −28 → 28 | −9 → 9, −12 → 12, −23 → 23 | −16 → 16, −10 → 10, −18 → 18 | −7 → 7, −14 → 14, −27 → 27 |

Refinement

| | | | | | | |
|---|---|---|---|---|---|---|
| $R[F^2 > 2σ(F^2)]$, $WR(F^2)$, S | 0.0212, 0.0533, 1.074 | 0.0333, 0.0780, 1.185 | 0.0308, 0.0751, 1.098 | 0.0199, 0.0480, 1.109 | 0.0203, 0.0527, 1.114 | 0.0261, 0.0604, 1.102 |
| No. of reflections | 3138 | 3277 | 3205 | 2857 | 3214 | 3040 |
| No. of parameters | 168 | 178 | 169 | 166 | 169 | 168 |
| No. of restraints | 3 | 3 | 3 | 3 | 9 | 3 |
| Absolute structure | Flack x determined using 1231 quotients [(I+) − (I−)]/[(I+) + (I−)] (Parsons, Flack and Wagner, Acta Cryst. B69 (2013) 249-259). | Flack x determined using 1238 quotients [(I+) − (I−)]/[(I+) + (I−)] (Parsons, Flack and Wagner, Acta Cryst. B69 (2013) 249-259). | Flack x determined using 1164 quotients [(I+) − (I−)]/[(I+) + (I−)] (Parsons, Flack and Wagner, Acta Cryst. B69 (2013) 249-259). | Refined as a perfect inversion twin. | — | Flack x determined using 1081 quotients [(I+) − (I−)]/[(I+) + (I−)] (Parsons, Flack and Wagner, Acta Cryst. B69 (2013) 249-259). |
| Absolute structure parameter | 0.003(4) | −0.005(7) | 0.006(8) | 0.5 | — | 0.008(8) |
| H-atom treatment | H atoms treated by a mixture of independent and constrained refinement | H atoms treated by a mixture of independent and constrained refinement | H atoms treated by a mixture of independent and constrained refinement | H atoms treated by a mixture of independent and constrained refinement | H atoms treated by a mixture of independent and constrained refinement | H atoms treated by a mixture of independent and constrained refinement |
| w | w = 1/[σ²($F_o^2$) + (0.0188P)² + 0.9897P] where P = ($F_o^2$ + 2$F_c^2$)/3 | w = 1/[σ²($F_o^2$) + (0.0294P)₂ + 1.2889P] where P = ($F_o^2$ + 2$F_c^2$)/3 | w = 1/[σ²($F_o^2$) + (0.0318P)² + 1.1523P] where P = ($F_o^2$ + 2$F_c^2$)/3 | w = 1/[σ²($F_o^2$) + (0.0179P)² + 0.8376P] where P = ($F_o^2$ + 2$F_c^2$)/3 | w = 1/[σ²($F_o^2$) + (0.0216P)² + 0.9204P] where P = ($F_o^2$ + 2$F_c^2$)/3 | w = 1/[σ²($F_o^2$) + (0.0203P)² + 0.9980P] where P = ($F_o^2$ + 2$F_c^2$)/3 |
| $(Δ/σ)_{max}$ | 0.001 | 0.002 | 0.001 | 0.001 | 0.002 | 0.000 |
| $Δρ_{max}$, $Δρ_{min}$ (e Å⁻³) | 0.603, −0.770 | 0.968, −0.489 | 0.881, −0.548 | 0.456, −0.474 | 0.435, −0.572 | 0.888, −0.889 |
| | Data collection: Bruker APEX4; cell refinement: Bruker SAINT; data reduction: Bruker SAINT; program(s) used to solve structure: | Data collection: Bruker APEX4; cell refinement: Bruker SAINT; data reduction: Bruker SAINT; program(s) used to solve structure: | Data collection: Bruker APEX4; cell refinement: Bruker SAINT; data reduction: Bruker SAINT; program(s) used to solve structure: | Data collection: Bruker APEX3; cell refinement: Bruker SAINT; data reduction: Bruker SAINT; program(s) used to solve structure: | Data collection: Bruker APEX4; cell refinement: Bruker SAINT; data reduction: Bruker SAINT; program(s) used to solve structure: | Data collection: Bruker APEX4; cell refinement: Bruker SAINT; data reduction: Bruker SAINT; program(s) used to solve structure: |

TABLE 3-continued

Single crystal data and structure refinement parameters

| Crystal data | Crystalline form 1 of 5-Cl-NiPT iodide | Crystalline form 1 of 5-MeO-NiPT iodide | Crystalline form 1 of 5-Me-NiPT iodide | Crystalline form 1 of 2-Me-NiPT iodide | Crystalline form 1 of 7-Me-NiPT iodide | Crystalline form of 1 5-F-NiPT iodide |
|---|---|---|---|---|---|---|
| | SHELXS97 (Sheldrick 2008); program(s) used to refine structure: SHELXL 2018/3 (Sheldrick, 2015); molecular graphics: Olex2 1.3 (Dolomanov et al., 2009); software used to prepare material for publication: Olex2 1.3 (Dolomanov et al., 2009). | SHELXS97 (Sheldrick 2008); program(s) used to refine structure: SHELXL 2018/3 (Sheldrick, 2015); molecular graphics: Olex2 1.3 (Dolomanov et al., 2009); software used to prepare material for publication: Olex2 1.3 (Dolomanov et al., 2009). | SHELXS97 (Sheldrick 2008); program(s) used to refine structure: SHELXL 2018/3 (Sheldrick, 2015); molecular graphics: Olex2 1.3 (Dolomanov et al., 2009); software used to prepare material for publication: Olex2 1.3 (Dolomanov et al., 2009). | SHELXT 2018/2 (Sheldrick 2018); program(s) used to refine structure: SHELXL 2018/3 (Sheldrick, 2015); molecular graphics: Olex2 1.5 (Dolomanov et al., 2009); software used to prepare material for publication: Olex2 1.5 (Dolomanov et al., 2009). | SHELXS97 (Sheldrick 2008); program(s) used to refine structure: SHELXL 2018/3 (Sheldrick, 2015); molecular graphics: Olex2 1.5 (Dolomanov et al., 2009); software used to prepare material for publication: Olex2 1.5 (Dolomanov et al., 2009). | SHELXS97 (Sheldrick 2008); program(s) used to refine structure: SHELXL 2018/3 (Sheldrick, 2015); molecular graphics: Olex2 1.5 (Dolomanov et al., 2009); software used to prepare material for publication: Olex2 1.5 (Dolomanov et al., 2009). |

FIG. 1 shows the molecular structure of crystalline form 1 of 5-Cl-NiPT iodide, showing the atomic labeling.

Figure 2:
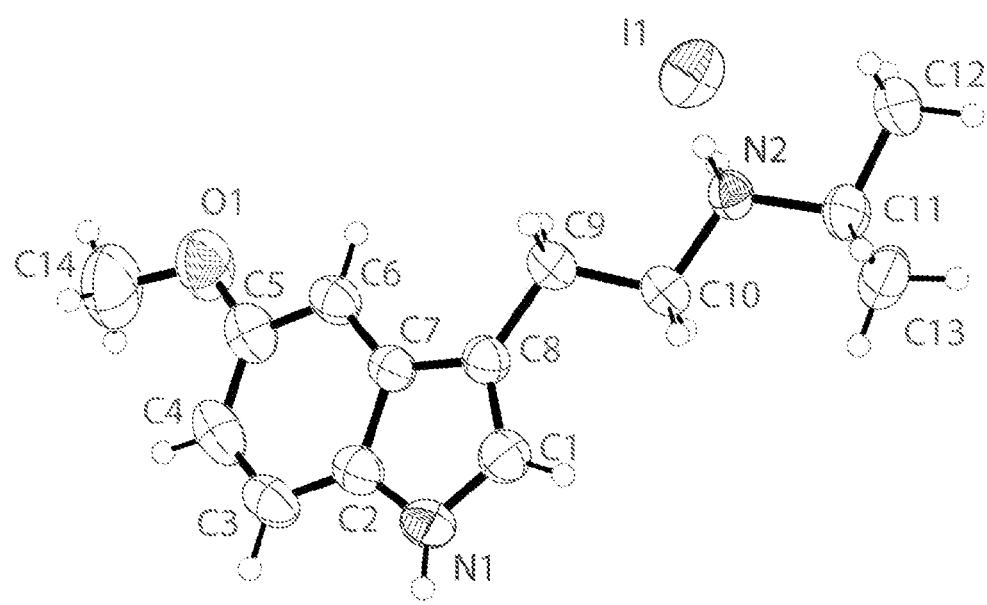
FIG. 2 shows the molecular structure of crystalline form 1 of 5-methoxy-N-isopropyltryptammonium iodide.

FIG. 2 shows the molecular structure of crystalline form 1 of 5-MeO-NiPT iodide, showing the atomic labeling.

Figure 3:
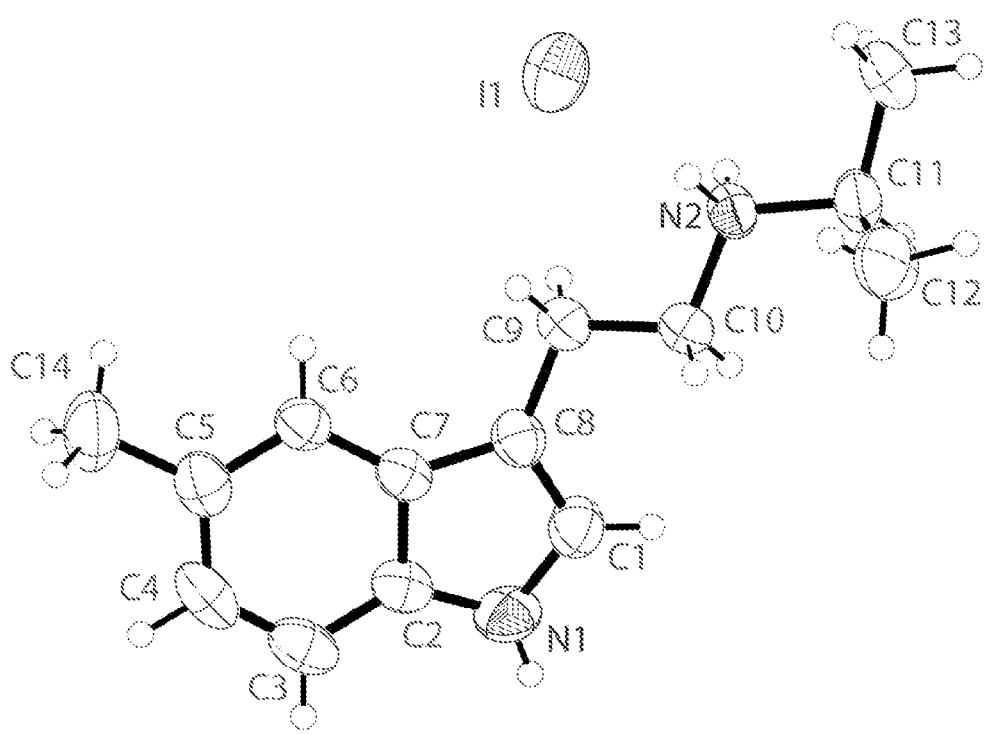
FIG. 3 shows the molecular structure of crystalline form 1 of 5-methyl-N-isopropyltryptammonium iodide.

FIG. 3 shows the molecular structure of crystalline form 1 of 5-Me-NiPT iodide, showing the atomic labeling.

Figure 4:
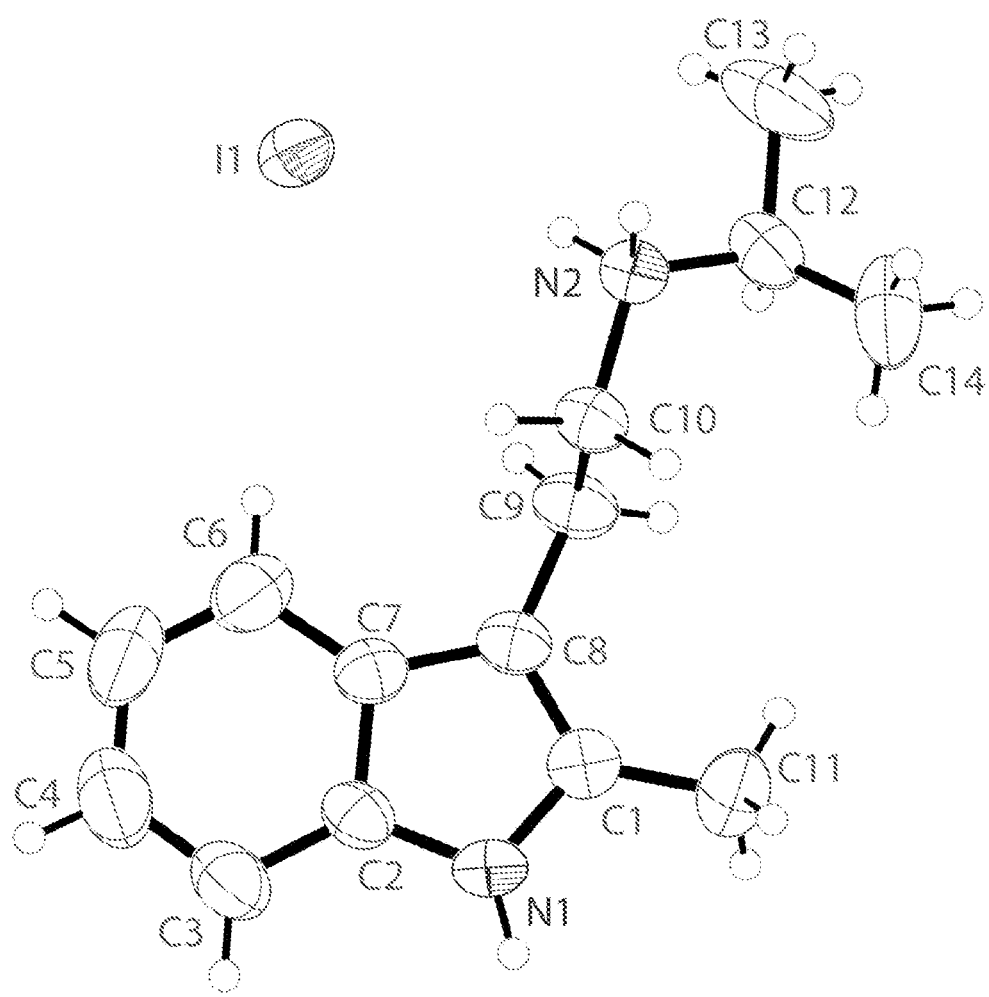
FIG. 4 shows the molecular structure of crystalline form 1 of 2-methyl-N-isopropyltryptammonium iodide.

FIG. 4 shows the molecular structure of crystalline form 1 of 2-Me-NiPT iodide, showing the atomic labeling.

Figure 5:
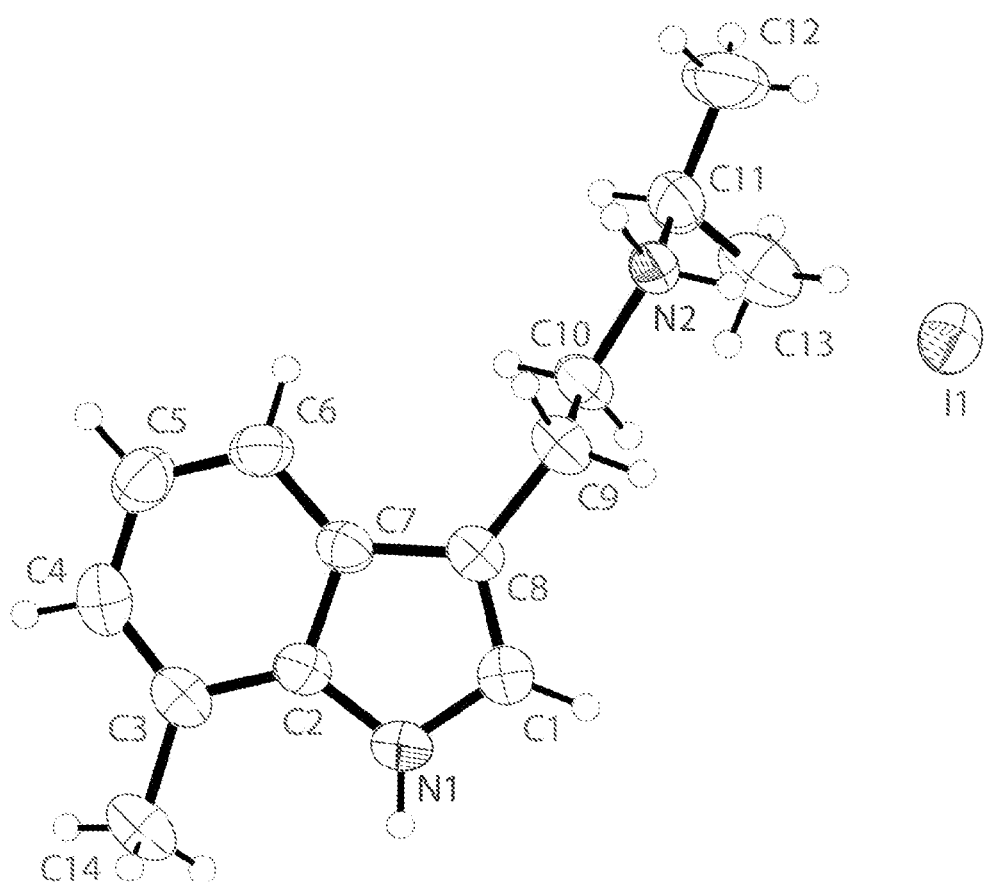
FIG. 5 shows the molecular structure of crystalline form 1 of 7-methyl-N-isopropyltryptammonium iodide.

FIG. 5 shows the molecular structure of crystalline form 1 of 7-Me-NiPT iodide, showing the atomic labeling.

Figure 6:
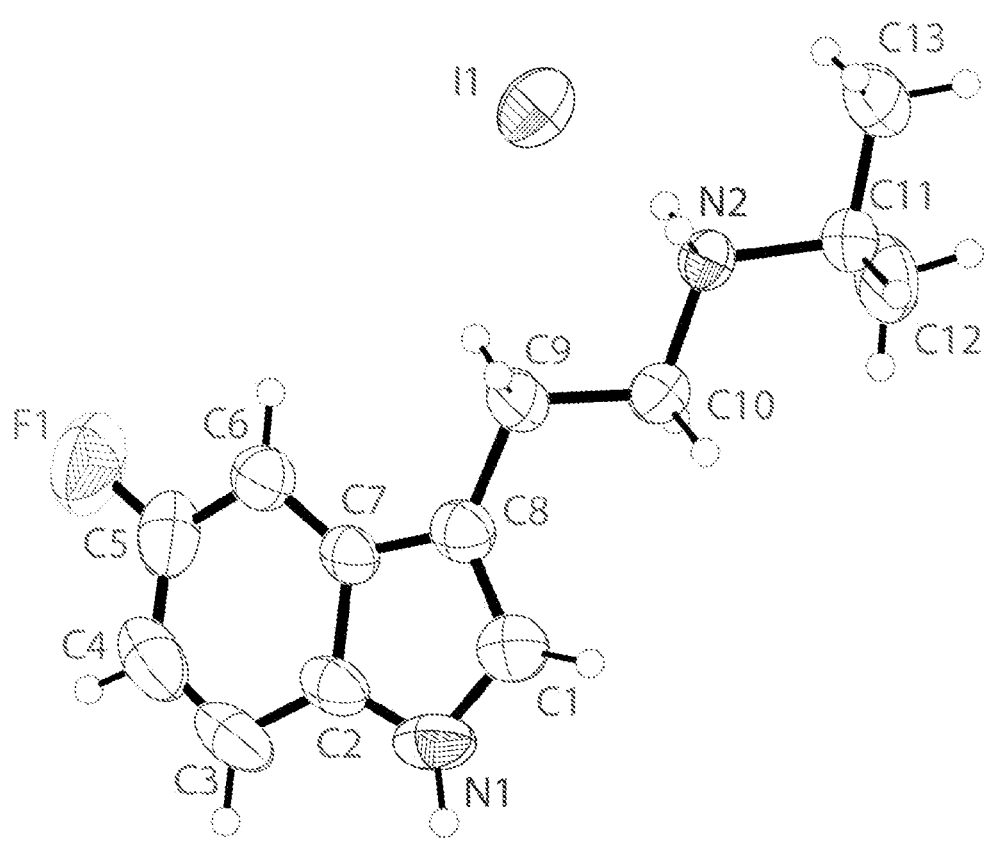
FIG. 6 shows the molecular structure of crystalline form 1 of 5-fluoro-N-isopropyltryptammonium iodide.

FIG. 6 shows the molecular structure of crystalline form 1 of 5-F-NiPT iodide, showing the atomic labeling.

Figure 7:
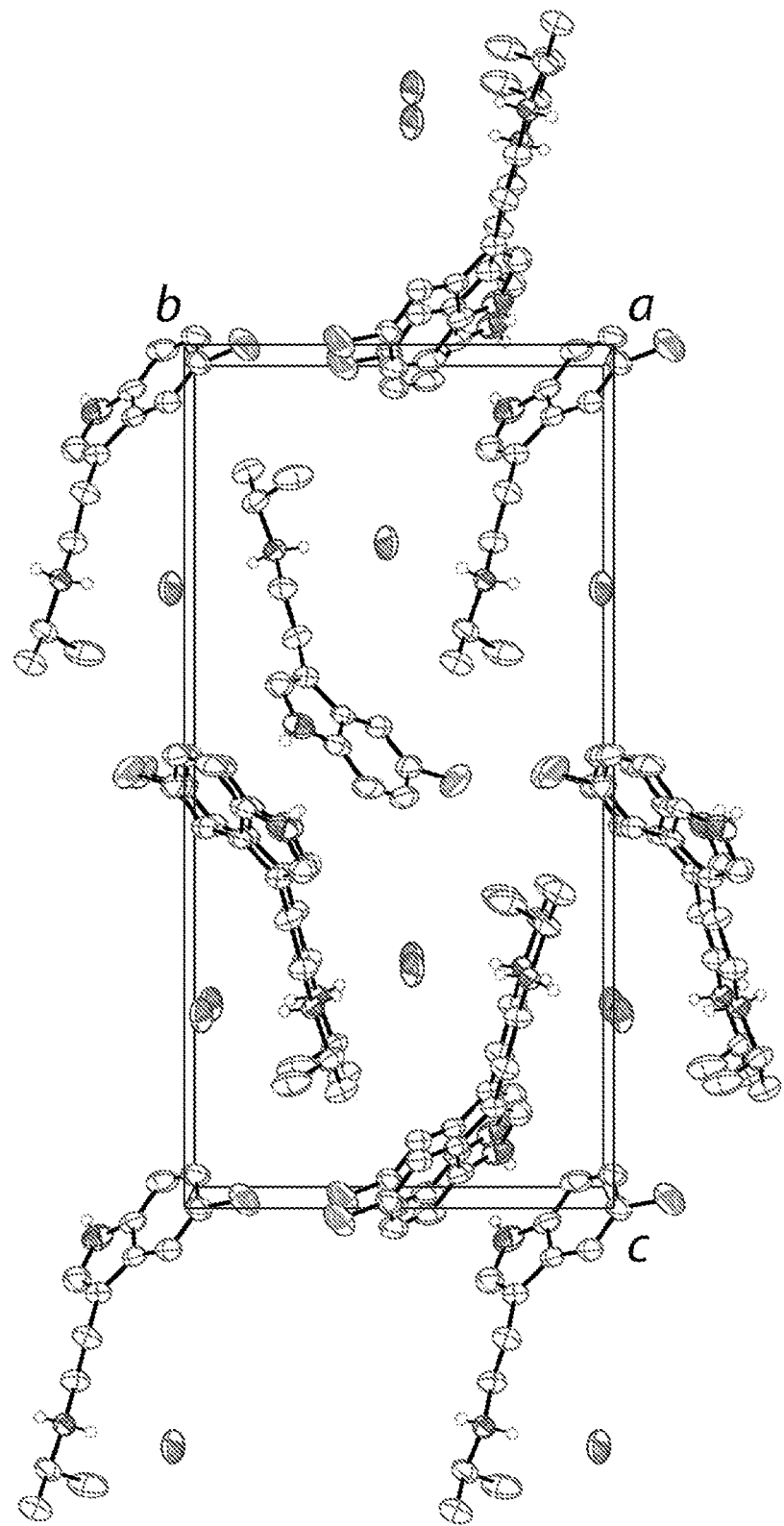
FIG. 7 shows the unit cell of crystalline form 1 of 5-chloro-N-isopropyltryptammonium iodide along the a-axis.

FIG. 7 shows the unit cell of crystalline form 1 of 5-Cl-NiPT iodide along the a-axis.

Figure 8:
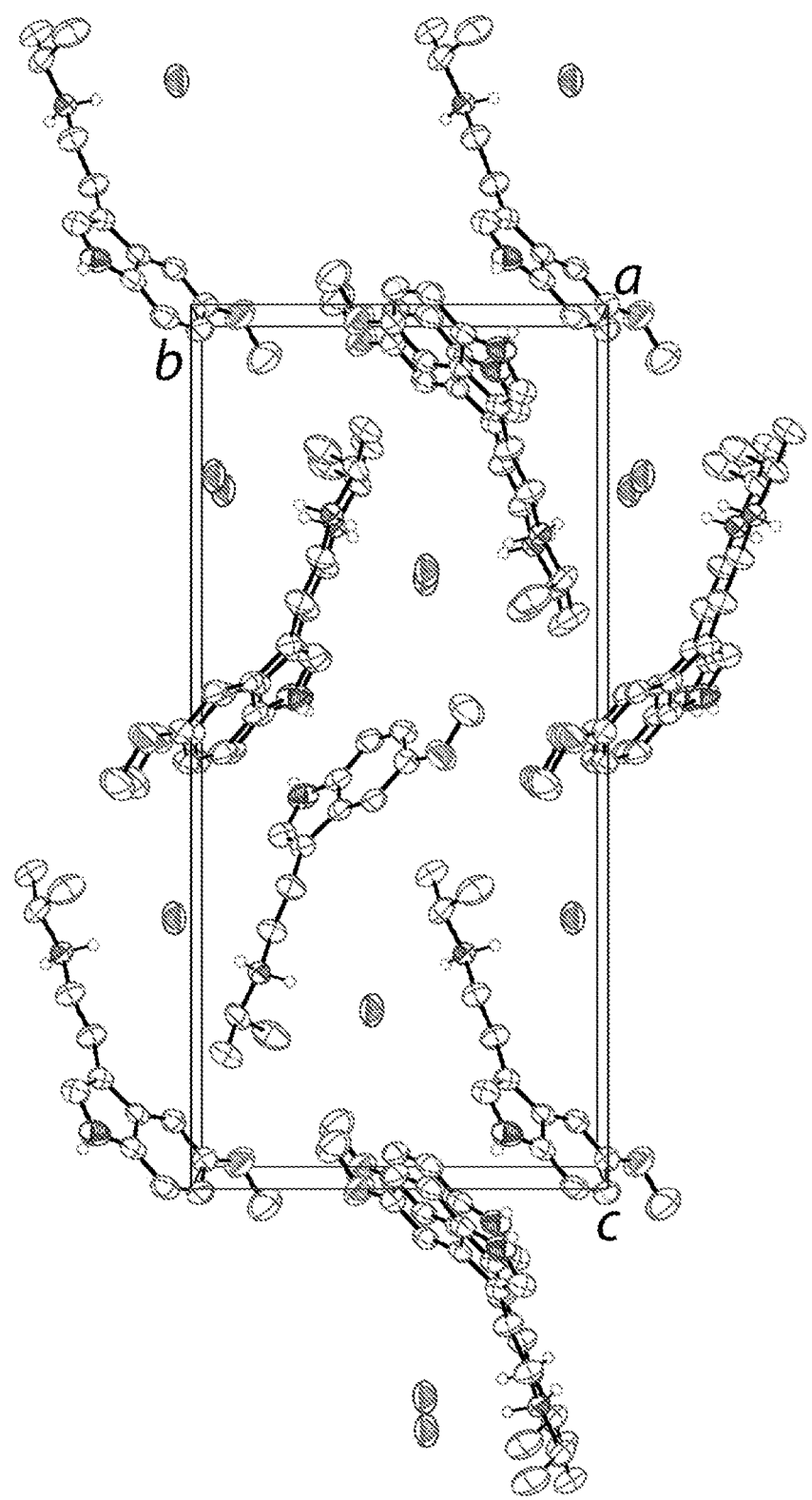
FIG. 8 shows the unit cell of crystalline form 1 of 5-methoxy-N-isopropyltryptammonium iodide along the a-axis.

FIG. 8 shows the unit cell of crystalline form 1 of 5-MeO-NiPT iodide along the a-axis.

Figure 9:
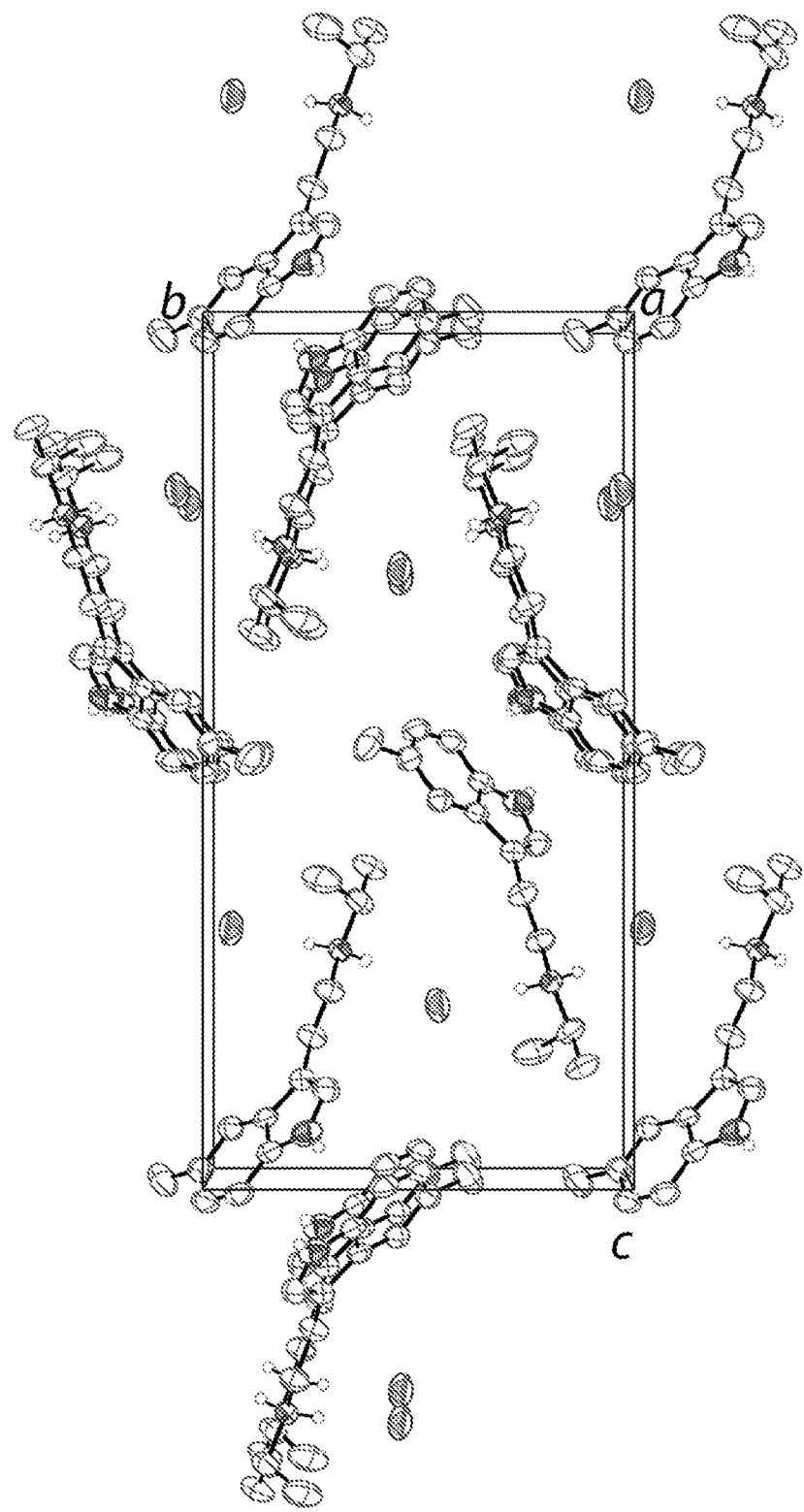
FIG. 9 shows the unit cell of crystalline form 1 of 5-methyl-N-isopropyltryptammonium iodide along the a-axis.

FIG. 9 shows the unit cell of crystalline form 1 of 5-Me-NiPT iodide along the a-axis.

Figure 10:
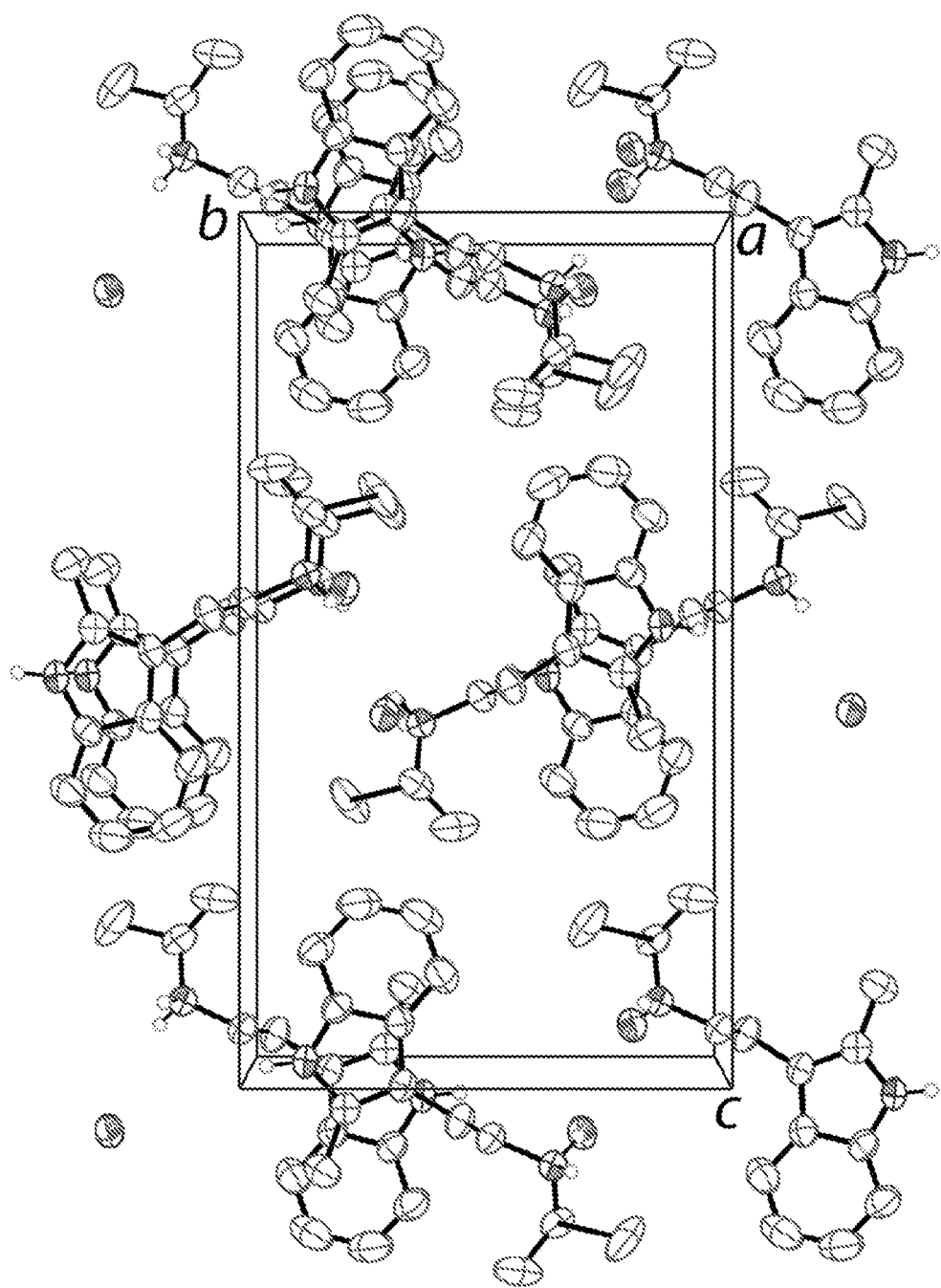
FIG. 10 shows the unit cell of crystalline form 1 of 2-methyl-N-isopropyltryptammonium iodide along the a-axis.

FIG. 10 shows the unit cell of crystalline form 1 of 2-Me-NiPT iodide along the a-axis.

Figure 11:
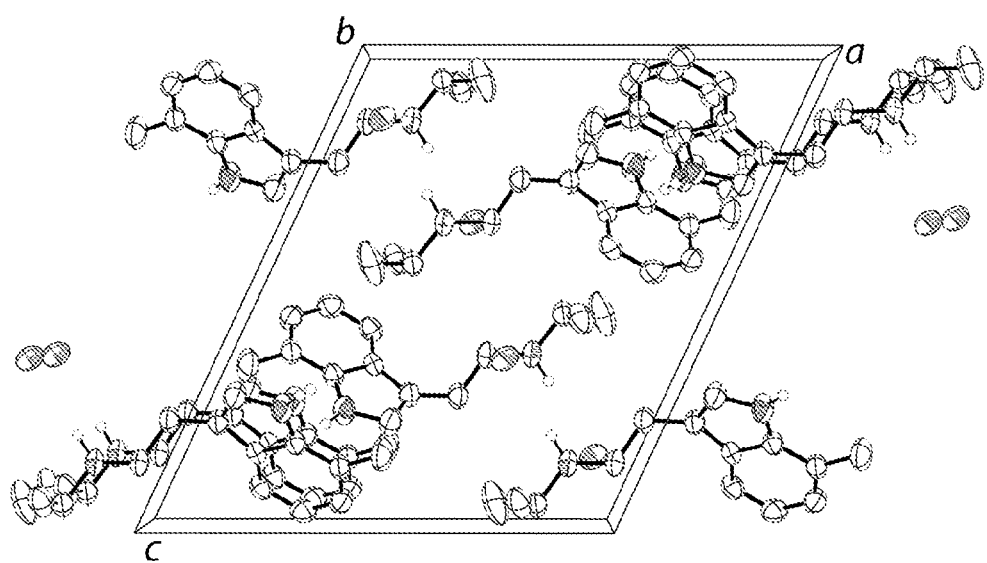
FIG. 11 shows the unit cell of crystalline form 1 of 7-methyl-N-isopropyltryptammonium iodide along the b-axis.

FIG. 11 shows the unit cell of crystalline form 1 of 7-Me-NiPT iodide along the b-axis.

Figure 12:
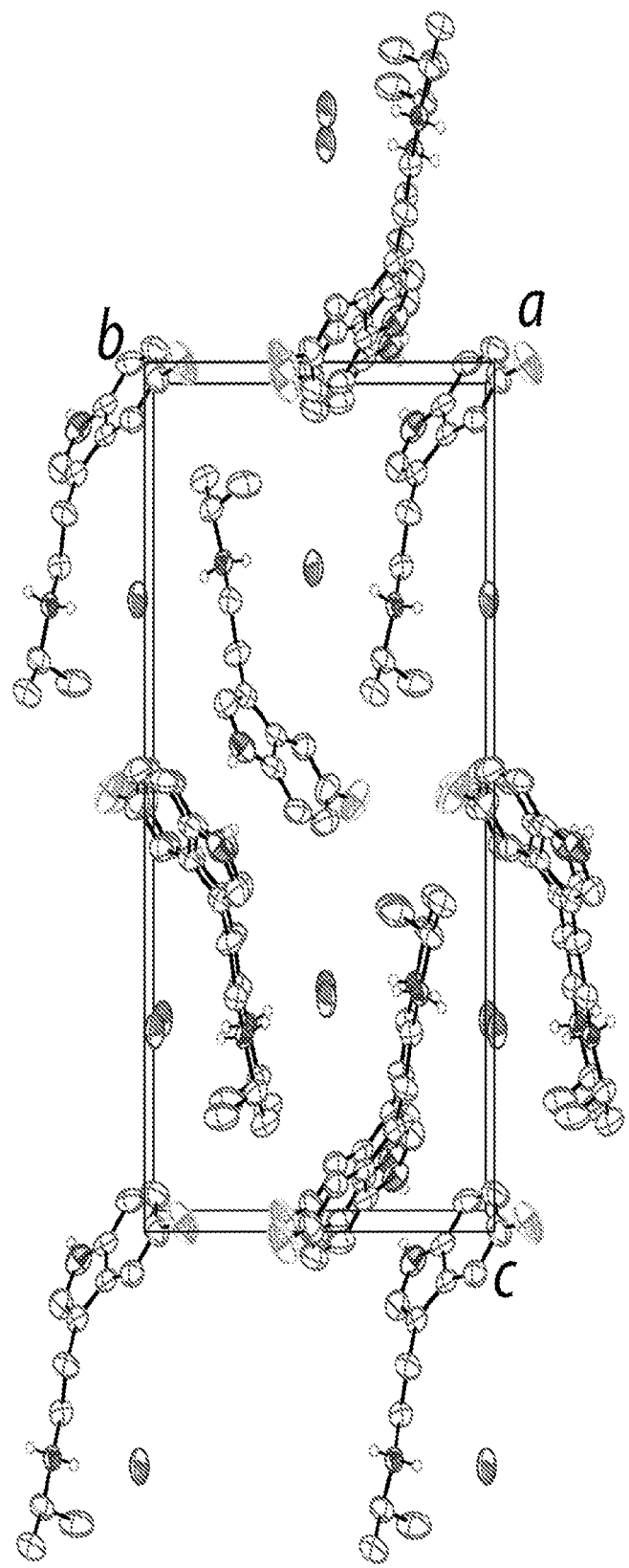
FIG. 12 shows the unit cell of crystalline form 1 of 5-fluoro-N-isopropyltryptammonium iodide along the a-axis.

FIG. 12 shows the unit cell of crystalline form 1 of 5-F-NiPT iodide along the a-axis.

Simulated Powder X-ray Diffraction (PXRD) Pattern

Figure 13:
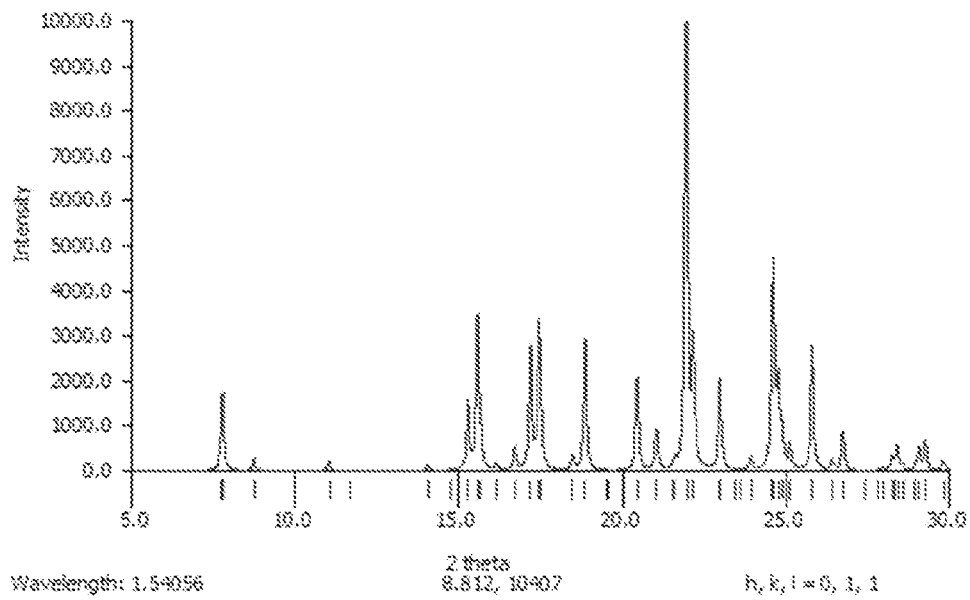
FIG. 13 shows the simulated X-ray powder diffraction pattern (XRPD) for crystalline form 1 of 5-chloro-N-isopropyltryptammonium iodide.

FIG. 13 shows a simulated X-ray powder diffraction pattern (XRPD) for crystalline form 1 of 5-Cl-NiPT iodide generated from its single crystal data. Table 4 lists the angles, ° 2θ±0.2° 2θ, and d-spacing of the peaks identified in the experimental XRPD pattern of FIG. 13. The entire list of peaks, or a subset thereof, may be sufficient to characterize the cocrystal. For example, the cocrystal may be characterized by at least two peaks selected from the peaks at 8.7, 18.9, and 20.5° 2θ±0.2° 2θ or their corresponding d-spacing as well as by an XRPD pattern substantially similar to FIG. 13.

Simulated Powder X-ray Diffraction (PXRD) Pattern

Figure 14:
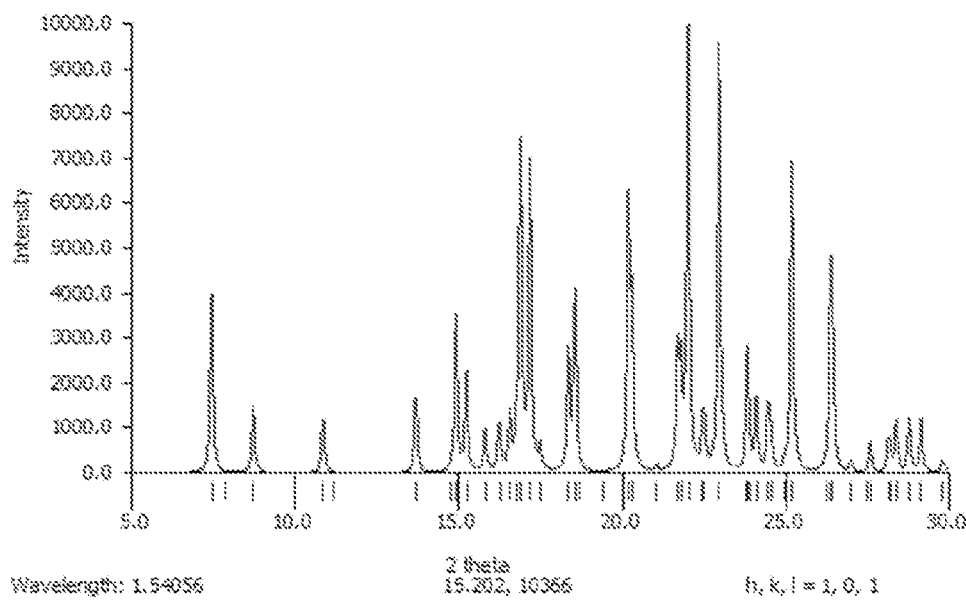
FIG. 14 shows the simulated X-ray powder diffraction pattern (XRPD) for crystalline form 1 of 5-methoxy-N-isopropyltryptammonium iodide.

FIG. 14 shows a simulated X-ray powder diffraction pattern (XRPD) for crystalline form 1 of 5-MeO-NiPT iodide generated from its single crystal data. Table 5 lists the angles, 02θ±0.2° 2θ, and d-spacing of the peaks identified in the experimental XRPD pattern of FIG. 14. The entire list of peaks, or a subset thereof, may be sufficient to characterize the cocrystal. For example, the cocrystal may be characterized by at least two peaks selected from the peaks at 7.4, 8.7, 10.8, and 13.7° 2θ±0.2° 2θ or their corresponding d-spacing as well as by an XRPD pattern substantially similar to FIG. 14.

Simulated Powder X-Ray Diffraction (PXRD) Pattern

Figure 15:
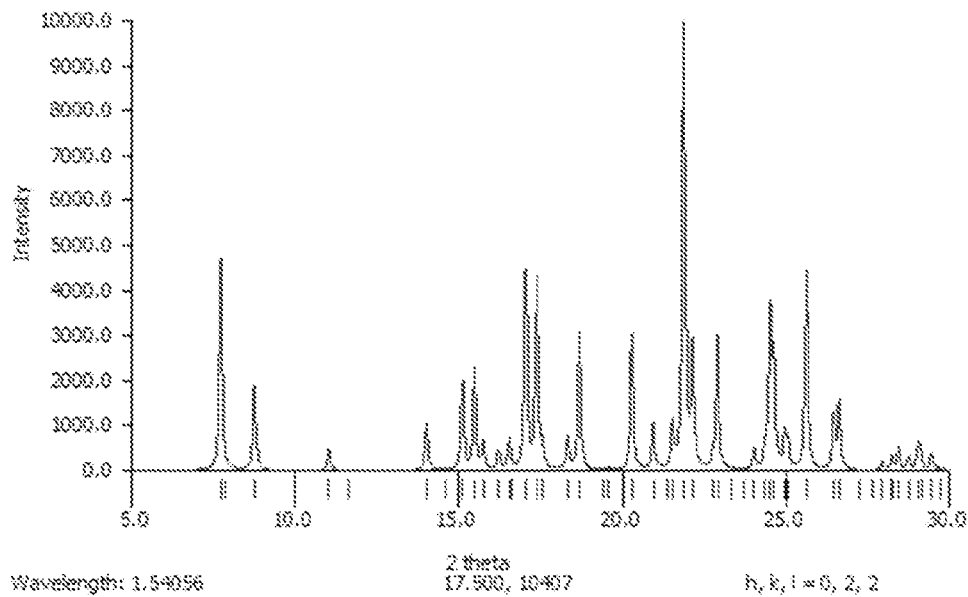
FIG. 15 shows the simulated X-ray powder diffraction pattern (XRPD) for crystalline form 1 of 5-methyl-N-isopropyltryptammonium iodide.

FIG. 15 shows a simulated X-ray powder diffraction pattern (XRPD) for crystalline form 1 of 5-Me-NiPT iodide generated from its single crystal data. Table 6 lists the angles, ° 2θ±0.2° 2θ, and d-spacing of the peaks identified in the experimental XRPD pattern of FIG. 15. The entire list of peaks, or a subset thereof, may be sufficient to characterize the cocrystal. For example, the cocrystal may be characterized by at least two peaks selected from the peaks at 7.7, 8.8, and 20.3° 2θ±0.2° 2θ or their corresponding d-spacing as well as by an XRPD pattern substantially similar to FIG. 15.

Simulated Powder X-Ray Diffraction (PXRD) Pattern

Figure 16:
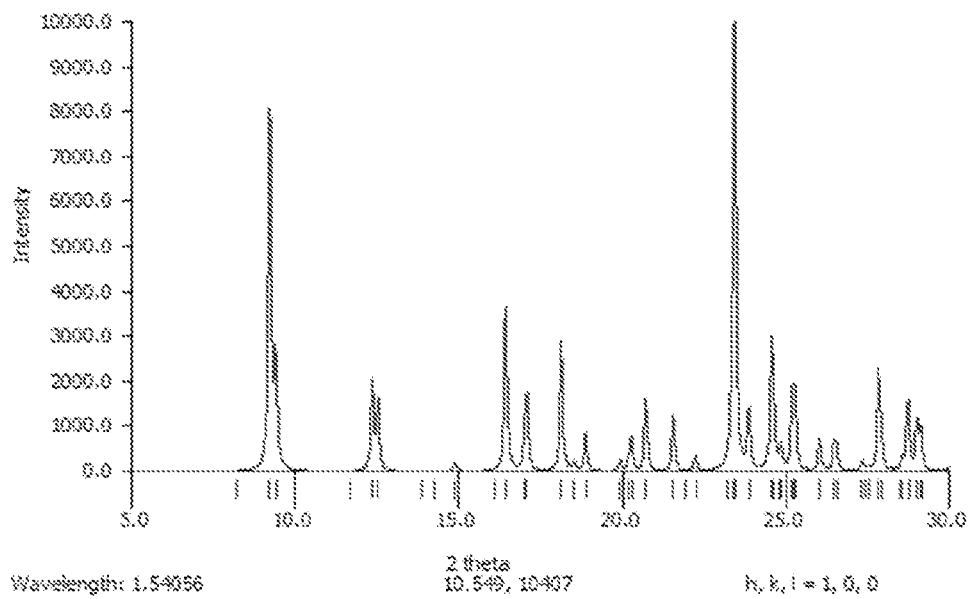
FIG. 16 shows the simulated X-ray powder diffraction pattern (XRPD) for crystalline form 1 of 2-methyl-N-isopropyltryptammonium iodide.

FIG. 16 shows a simulated X-ray powder diffraction pattern (XRPD) for crystalline form 1 of 2-Me-NiPT iodide generated from its single crystal data. Table 7 lists the angles, ° 2θ±0.2° 2θ, and d-spacing of the peaks identified in the experimental XRPD pattern of FIG. 16. The entire list of peaks, or a subset thereof, may be sufficient to characterize the cocrystal. For example, the cocrystal may be characterized by at least two peaks selected from the peaks at 9.2, 16.4, and 18.1° 2θ±0.2° 2θ or their corresponding d-spacing as well as by an XRPD pattern substantially similar to FIG. 16.

Simulated Powder X-Ray Diffraction (PXRD) Pattern

Figure 17:
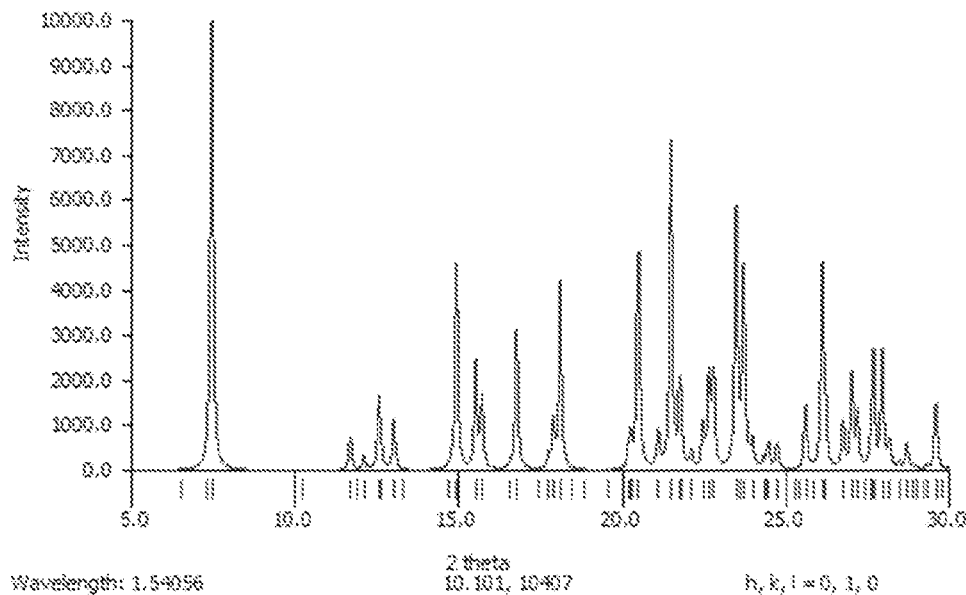
FIG. 17 shows the simulated X-ray powder diffraction pattern (XRPD) for crystalline form 1 of 7-methyl-N-isopropyltryptammonium iodide.

FIG. 17 shows a simulated X-ray powder diffraction pattern (XRPD) for crystalline form 1 of 7-Me-NiPT iodide generated from its single crystal data. Table 8 lists the angles, ° 2θ±0.2° 2θ, and d-spacing of the peaks identified in the experimental XRPD pattern of FIG. 17. The entire list of peaks, or a subset thereof, may be sufficient to characterize the cocrystal. For example, the cocrystal may be characterized by at least two peaks selected from the peaks at 7.4, 14.9, and 16.8° 2θ±0.2° 2θ or their corresponding d-spacing as well as by an XRPD pattern substantially similar to FIG. 17.

Simulated Powder X-Ray Diffraction (PXRD) Pattern

Figure 18:
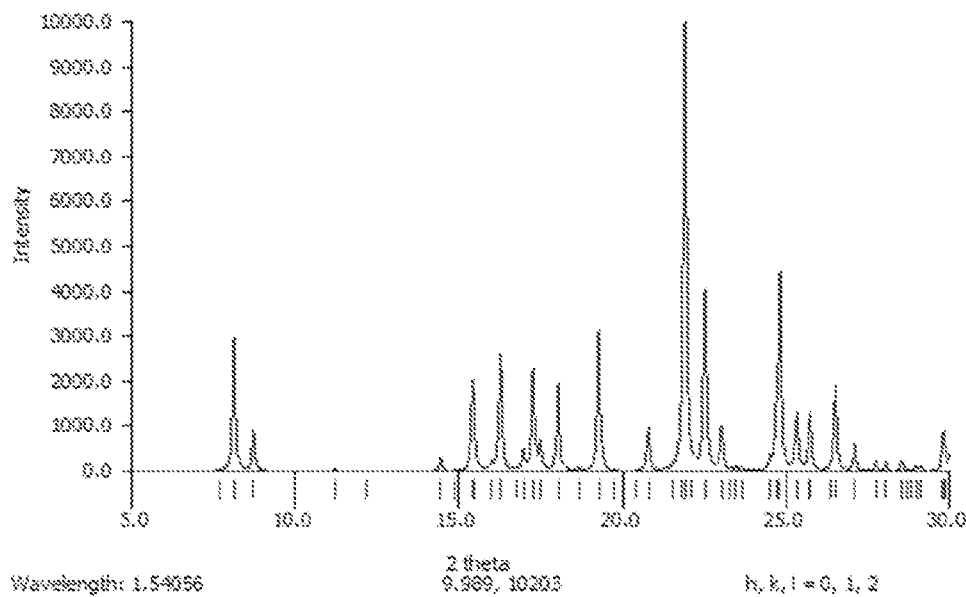
FIG. 18 shows the simulated X-ray powder diffraction pattern (XRPD) for crystalline form 1 of 5-fluoro-N-isopropyltryptammonium iodide.

FIG. 18 shows a simulated X-ray powder diffraction pattern (XRPD) for crystalline form 1 of 5-F-NiPT iodide generated from its single crystal data. Table 9 lists the angles, ° 2θ±0.2° 2θ, and d-spacing of the peaks identified in the experimental XRPD pattern of FIG. 18. The entire list of peaks, or a subset thereof, may be sufficient to characterize the cocrystal. For example, the cocrystal may be characterized by at least two peaks selected from the peaks at 8.1, 19.3, and 20.8° 2θ±0.2° 2θ or their corresponding d-spacing as well as by an XRPD pattern substantially similar to FIG. 18.

TABLE 4

Crystalline form 1 of 5-Cl-NiPT iodide

| d-spacing (Å) | °2θ + 0.2°2θ | Intensity |
| --- | --- | --- |
| 11.36 | 7.77 | 9072 |
| 10.12 | 8.73 | 1760 |
| 8.01 | 11.03 | 2482 |
| 6.29 | 14.06 | 2167 |
| 5.79 | 15.28 | 30567 |
| 5.68 | 15.58 | 71059 |
| 5.65 | 15.67 | 8624 |
| 5.48 | 16.15 | 3515 |
| 5.30 | 16.72 | 11422 |
| 5.29 | 16.74 | 1766 |
| 5.15 | 17.19 | 71836 |
| 5.08 | 17.46 | 80331 |
| 5.06 | 17.52 | 19028 |
| 4.80 | 18.48 | 9190 |
| 4.70 | 18.87 | 94011 |
| 4.53 | 19.59 | 64 |
| 4.34 | 20.45 | 77323 |
| 4.22 | 21.05 | 35103 |
| 4.12 | 21.54 | 73 |
| 4.11 | 21.61 | 6826 |
| 4.04 | 21.96 | 420479 |
| 4.01 | 22.17 | 119599 |
| 3.87 | 22.94 | 10545 |
| 3.86 | 22.99 | 92779 |
| 3.79 | 23.46 | 343 |
| 3.72 | 23.93 | 16067 |
| 3.62 | 24.56 | 37156 |
| 3.61 | 24.62 | 232855 |
| 3.59 | 24.77 | 96255 |
| 3.57 | 24.89 | 40694 |
| 3.54 | 25.12 | 29691 |
| 3.45 | 25.81 | 168542 |
| 3.37 | 26.41 | 16460 |
| 3.33 | 26.75 | 57870 |
| 3.20 | 27.84 | 886 |
| 3.19 | 27.96 | 5675 |
| 3.16 | 28.24 | 22962 |
| 3.15 | 28.34 | 1634 |
| 3.14 | 28.41 | 39666 |
| 3.12 | 28.58 | 9391 |
| 3.08 | 28.96 | 6478 |
| 3.07 | 29.07 | 39561 |
| 3.05 | 29.27 | 53312 |
| 3.00 | 29.80 | 17714 |

TABLE 5

Crystalline form 1 of 5-MeO-NiPT iodide

| d-spacing (Å) | °2θ + 0.2°2θ | Intensity |
| --- | --- | --- |
| 11.87 | 7.44 | 9773 |
| 10.13 | 8.72 | 4952 |
| 8.15 | 10.85 | 6516 |
| 6.46 | 13.69 | 14222 |
| 5.93 | 14.92 | 34940 |
| 5.81 | 15.23 | 23554 |
| 5.60 | 15.80 | 10208 |
| 5.45 | 16.24 | 12369 |
| 5.35 | 16.56 | 14764 |
| 5.29 | 16.76 | 8784 |
| 5.24 | 16.89 | 94763 |
| 5.16 | 17.17 | 92372 |
| 5.07 | 17.49 | 7554 |
| 4.83 | 18.36 | 40287 |
| 4.78 | 18.56 | 62412 |
| 4.57 | 19.40 | 33 |
| 4.40 | 20.19 | 110902 |
| 4.37 | 20.30 | 67725 |
| 4.22 | 21.05 | 2696 |
| 4.09 | 21.69 | 54224 |
| 4.07 | 21.80 | 46913 |
| 4.03 | 22.02 | 219894 |
| 3.96 | 22.46 | 14918 |
| 3.95 | 22.51 | 22124 |
| 3.87 | 22.96 | 233604 |
| 3.73 | 23.83 | 73468 |
| 3.72 | 23.89 | 549 |
| 3.69 | 24.10 | 42705 |
| 3.64 | 24.46 | 38780 |
| 3.62 | 24.56 | 20503 |
| 3.56 | 24.97 | 5804 |
| 3.53 | 25.19 | 206314 |
| 3.38 | 26.36 | 113419 |
| 3.37 | 26.43 | 114299 |
| 3.30 | 26.98 | 8360 |
| 3.25 | 27.46 | 285 |
| 3.23 | 27.58 | 23678 |
| 3.17 | 28.12 | 4888 |
| 3.17 | 28.15 | 20082 |
| 3.16 | 28.20 | 8458 |
| 3.14 | 28.38 | 44714 |
| 3.10 | 28.77 | 46416 |
| 3.06 | 29.13 | 49362 |
| 3.00 | 29.79 | 11096 |

TABLE 6

Crystalline form 1 of 5-Me-NiPT iodide

| d-spacing (Å) | °2θ + 0.2°2θ | Intensity |
| --- | --- | --- |
| 11.43 | 7.73 | 19225 |
| 10.10 | 8.75 | 10059 |
| 8.02 | 11.02 | 4157 |
| 6.31 | 14.02 | 14260 |
| 5.86 | 15.11 | 31465 |
| 5.72 | 15.49 | 37865 |
| 5.63 | 15.74 | 10092 |
| 5.46 | 16.21 | 7246 |
| 5.35 | 16.54 | 12479 |
| 5.34 | 16.60 | 249 |
| 5.20 | 17.05 | 90950 |
| 5.10 | 17.39 | 88437 |
| 5.05 | 17.56 | 9938 |
| 4.84 | 18.33 | 16435 |
| 4.74 | 18.69 | 76677 |
| 4.53 | 19.60 | 1252 |
| 4.37 | 20.30 | 86796 |
| 4.24 | 20.95 | 31563 |
| 4.16 | 21.35 | 90 |
| 4.12 | 21.53 | 31572 |
| 4.06 | 21.89 | 336777 |
| 4.01 | 22.15 | 94949 |

TABLE 6-continued

Crystalline form 1 of 5-Me-NiPT iodide

| d-spacing (Å) | °2θ + 0.2°2θ | Intensity |
|---|---|---|
| 3.90 | 22.78 | 8041 |
| 3.88 | 22.91 | 113233 |
| 3.81 | 23.32 | 997 |
| 3.70 | 24.03 | 18472 |
| 3.65 | 24.36 | 19471 |
| 3.63 | 24.53 | 147950 |
| 3.61 | 24.64 | 101120 |
| 3.56 | 24.97 | 34982 |
| 3.55 | 25.07 | 27407 |
| 3.47 | 25.63 | 209878 |
| 3.37 | 26.46 | 59361 |
| 3.34 | 26.63 | 77036 |
| 3.23 | 27.62 | 248 |
| 3.19 | 27.95 | 10532 |
| 3.16 | 28.23 | 16259 |
| 3.16 | 28.26 | 2021 |
| 3.14 | 28.43 | 630 |
| 3.14 | 28.44 | 28242 |
| 3.10 | 28.76 | 16768 |
| 3.07 | 29.04 | 39169 |
| 3.06 | 29.14 | 15537 |
| 3.03 | 29.45 | 25141 |
| 3.00 | 29.71 | 4165 |

TABLE 7

Crystalline form 1 of 2-Me-NiPT iodide

| d-spacing (Å) | °2θ + 0.2°2θ | Intensity |
|---|---|---|
| 9.58 | 9.23 | 64420 |
| 9.39 | 9.41 | 19274 |
| 7.16 | 12.35 | 28512 |
| 7.06 | 12.53 | 22948 |
| 6.21 | 14.26 | 3 |
| 5.95 | 14.88 | 3751 |
| 5.91 | 14.99 | 989 |
| 5.49 | 16.12 | 153 |
| 5.39 | 16.44 | 94304 |
| 5.21 | 17.01 | 10305 |
| 5.19 | 17.08 | 44014 |
| 4.89 | 18.14 | 89335 |
| 4.79 | 18.52 | 5748 |
| 4.70 | 18.88 | 28609 |
| 4.45 | 19.93 | 8853 |
| 4.39 | 20.19 | 6334 |
| 4.38 | 20.28 | 27704 |
| 4.28 | 20.72 | 65575 |
| 4.12 | 21.56 | 56520 |
| 4.05 | 21.93 | 645 |
| 3.99 | 22.24 | 16283 |
| 3.80 | 23.41 | 279368 |
| 3.79 | 23.45 | 321234 |
| 3.72 | 23.87 | 71486 |
| 3.62 | 24.57 | 159094 |
| 3.61 | 24.65 | 54048 |
| 3.58 | 24.84 | 19119 |
| 3.58 | 24.85 | 9094 |
| 3.53 | 25.20 | 47090 |
| 3.53 | 25.21 | 44961 |
| 3.52 | 25.28 | 90502 |
| 3.42 | 26.03 | 48892 |
| 3.36 | 26.48 | 36348 |
| 3.35 | 26.55 | 36750 |
| 3.26 | 27.31 | 135 |
| 3.26 | 27.34 | 15103 |
| 3.25 | 27.44 | 1571 |
| 3.24 | 27.53 | 4277 |
| 3.20 | 27.84 | 167438 |
| 3.19 | 27.93 | 38552 |
| 3.13 | 28.48 | 1377 |
| 3.12 | 28.56 | 2969 |
| 3.12 | 28.57 | 16050 |

TABLE 7-continued

Crystalline form 1 of 2-Me-NiPT iodide

| d-spacing (Å) | °2θ + 0.2°2θ | Intensity |
|---|---|---|
| 3.10 | 28.74 | 123876 |
| 3.08 | 29.01 | 86782 |
| 3.06 | 29.12 | 60377 |
| 3.06 | 29.15 | 21462 |

TABLE 8

Crystalline form 1 of 7-Me-NiPT iodide

| d-spacing (Å) | °2θ + 0.2°2θ | Intensity |
|---|---|---|
| 11.86 | 7.45 | 33661 |
| 7.57 | 11.68 | 5878 |
| 7.31 | 12.09 | 2788 |
| 7.04 | 12.56 | 14373 |
| 7.00 | 12.63 | 3065 |
| 6.80 | 13.01 | 11343 |
| 6.03 | 14.67 | 512 |
| 5.93 | 14.93 | 62765 |
| 5.70 | 15.52 | 34050 |
| 5.64 | 15.71 | 23553 |
| 5.35 | 16.55 | 2374 |
| 5.28 | 16.77 | 54289 |
| 5.00 | 17.74 | 5388 |
| 4.95 | 17.89 | 19155 |
| 4.89 | 18.11 | 84719 |
| 4.40 | 20.18 | 7117 |
| 4.38 | 20.26 | 17227 |
| 4.34 | 20.46 | 13269 |
| 4.33 | 20.50 | 115041 |
| 4.21 | 21.10 | 20996 |
| 4.14 | 21.47 | 4344 |
| 4.13 | 21.49 | 202758 |
| 4.08 | 21.76 | 36910 |
| 4.07 | 21.80 | 28344 |
| 4.02 | 22.11 | 10845 |
| 3.95 | 22.48 | 28926 |
| 3.92 | 22.65 | 62962 |
| 3.90 | 22.78 | 63934 |
| 3.79 | 23.48 | 191714 |
| 3.76 | 23.62 | 2010 |
| 3.75 | 23.70 | 110005 |
| 3.74 | 23.74 | 69526 |
| 3.71 | 23.98 | 20014 |
| 3.66 | 24.32 | 8786 |
| 3.65 | 24.37 | 248 |
| 3.63 | 24.47 | 20911 |
| 3.60 | 24.73 | 20786 |
| 3.52 | 25.27 | 239 |
| 3.50 | 25.42 | 198 |
| 3.48 | 25.60 | 56977 |
| 3.47 | 25.65 | 1189 |
| 3.44 | 25.85 | 384 |
| 3.41 | 26.11 | 51150 |
| 3.41 | 26.12 | 132664 |
| 3.40 | 26.20 | 46029 |
| 3.33 | 26.75 | 45659 |
| 3.30 | 27.02 | 95294 |
| 3.28 | 27.20 | 56240 |
| 3.23 | 27.62 | 12783 |
| 3.22 | 27.67 | 121928 |
| 3.19 | 27.95 | 128979 |
| 3.17 | 28.15 | 6771 |
| 3.16 | 28.18 | 23737 |
| 3.13 | 28.46 | 8828 |
| 3.11 | 28.70 | 30691 |
| 3.09 | 28.89 | 5448 |
| 3.08 | 28.99 | 1524 |
| 3.04 | 29.32 | 5305 |
| 3.02 | 29.59 | 50304 |
| 3.02 | 29.59 | 34640 |

TABLE 9

| Crystalline form 1 of 5-F-NiPT iodide | | |
|---|---|---|
| d-spacing (Å) | °2θ + 0.2°2θ | Intensity |
| 10.88 | 8.12 | 17367 |
| 10.13 | 8.72 | 6175 |
| 7.89 | 11.21 | 844 |
| 6.13 | 14.45 | 5953 |
| 5.74 | 15.43 | 36275 |
| 5.72 | 15.47 | 13237 |
| 5.53 | 16.00 | 3681 |
| 5.44 | 16.28 | 62150 |
| 5.28 | 16.78 | 7 |
| 5.22 | 16.97 | 11124 |
| 5.13 | 17.27 | 62110 |
| 5.07 | 17.49 | 16036 |
| 4.91 | 18.04 | 57819 |
| 4.75 | 18.67 | 2418 |
| 4.60 | 19.28 | 106632 |
| 4.49 | 19.74 | 168 |
| 4.27 | 20.79 | 38545 |
| 4.12 | 21.53 | 1220 |
| 4.07 | 21.83 | 6879 |
| 4.05 | 21.92 | 446105 |
| 4.01 | 22.12 | 2 |
| 3.94 | 22.53 | 195112 |
| 3.86 | 23.04 | 47688 |
| 3.79 | 23.46 | 4739 |
| 3.76 | 23.66 | 5450 |
| 3.63 | 24.53 | 11297 |
| 3.60 | 24.71 | 39069 |
| 3.59 | 24.81 | 255152 |
| 3.51 | 25.34 | 74660 |
| 3.46 | 25.69 | 22074 |
| 3.46 | 25.75 | 67006 |
| 3.38 | 26.37 | 3260 |
| 3.36 | 26.52 | 125084 |
| 3.29 | 27.11 | 42951 |
| 3.21 | 27.75 | 16155 |
| 3.18 | 28.06 | 14254 |
| 3.12 | 28.55 | 19723 |
| 3.10 | 28.81 | 19 |
| 3.08 | 28.96 | 9504 |
| 3.06 | 29.13 | 10373 |

TABLE 9-continued

| Crystalline form 1 of 5-F-NiPT iodide | | |
|---|---|---|
| d-spacing (Å) | °2θ + 0.2°2θ | Intensity |
| 3.00 | 29.76 | 4568 |
| 2.99 | 29.82 | 70410 |
| 2.99 | 29.87 | 3341 |

REFERENCES

Dolomanov, O. V., Bourhis, L. J., Gildea, R. J., Howard, J. A. K. & Puschmann, H. (2009). J. Appl. Cryst. 42, 339-341.

Sheldrick, G. M. (2015). Acta Cryst. C71, 3-8.

Xu Y C, Schaus J M, Walker C, Krushinski J, Adham N, Zgombick J M, Liang S X, Kohlman D T, Audia J E. N-Methyl-5-tert-butyltryptamine: A novel, highly potent 5-HT1D receptor agonist. J Med Chem. 1999 Feb. 11; 42(3):526-31. Doi: 10.1021/jm9805945. PMID: 9986723.

The claimed invention is:

1. Crystalline form 1 of [2-(5-chloro-1H-indol-3-yl)ethyl](propan-2-yl)azanium iodide (5-chloro-N-isopropyltryptammonium iodide).

2. Crystalline form 1 of 5-chloro-N-isopropyltryptammonium iodide according to claim/characterized by at least one of:

a orthorhombic crystal system at a temperature of about 297 K;

a $P2_12_12_1$ space group at a temperature of about 297 K; unit cell dimensions a=5.9905(3) Å, b=11.2975(5) Å, c=22.7295(12) Å, α=90°, β=90°, and γ=90°;

an X-ray powder diffraction pattern substantially similar to FIG. 13; or an X-ray powder diffraction pattern characterized by at least two peaks selected from 8.7, 18.9, and 20.5° 2θ±0.2° 2θ.

* * * * *